(12) United States Patent
Marzabadi et al.

(10) Patent No.: US 7,105,544 B2
(45) Date of Patent: Sep. 12, 2006

(54) SUBSTITUTED ALKYL AMIDO PIPERIDINES

(75) Inventors: Mohammad R. Marzabadi, Ridgewood, NJ (US); John M. Wetzel, Fair Lawn, NJ (US); Chien-An Chen, Flushing, NY (US); Yu Jiang, Jersey City, NJ (US); Kai Lu, Lake Hiawatha, NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 90 days.

(21) Appl. No.: 10/345,063

(22) Filed: Jan. 14, 2003

(65) Prior Publication Data

Related U.S. Application Data

(63) Continuation-in-part of application No. 10/188,434, filed on Jul. 3, 2002, now Pat. No. 6,727,264.

(60) Provisional application No. 60/346,997, filed on Jan. 9, 2002, provisional application No. 60/303,091, filed on Jul. 5, 2001.

(51) Int. Cl.
*A61K 31/445* (2006.01)
*C07D 211/26* (2006.01)

(52) U.S. Cl. ............... 514/331; 514/318; 546/200; 546/233; 546/234

(58) Field of Classification Search ............ 514/331, 514/318; 546/233, 234, 200
See application file for complete search history.

(56) References Cited

U.S. PATENT DOCUMENTS

| | | | |
|---|---|---|---|
| 5,459,151 A | 10/1995 | Lombardo | |
| 6,441,000 B1 | 8/2002 | Gibson et al. | |
| 6,720,324 B1* | 4/2004 | Marzabadi et al. | 514/252.14 |
| 6,727,264 B1 | 4/2004 | Marzabadi et al. | |
| 2003/0077701 A1 | 2/2003 | Salon et al. | |
| 2004/0038855 A1* | 2/2004 | Salon et al. | 514/1 |

FOREIGN PATENT DOCUMENTS

| | | |
|---|---|---|
| WO | WO 00/021934 | 4/2000 |
| WO | WO 02/02744 | 1/2002 |
| WO | WO-02/06245 A1 | 1/2002 |
| WO | WO 02/030927 | 4/2002 |
| WO | WO-02/094799 A1 | 11/2002 |
| WO | WO-03/004027 A1 | 1/2003 |
| WO | WO-04/004714 A1 | 1/2004 |
| WO | WO-04/005257 A1 | 1/2004 |
| WO | WO 04/058727 | 7/2004 |

OTHER PUBLICATIONS

S. Takekawa, et al., "T-226296: a novel, orally active and selective melanin-concentrating hormone receptor antagonist", Eur. J. Pharmacol. 438(3), (2002) pp. 129-135.
U.S. Appl. No. 10/719,358, Marzabadi et al., filed Nov. 21, 2003, not yet published.

* cited by examiner

*Primary Examiner*—Celia Chang
(74) *Attorney, Agent, or Firm*—Darby & Darby

(57) ABSTRACT

This invention is directed to compounds which are selective antagonists for melanin concentrating hormone-1 (MCH1) receptors. The invention provides a pharmaceutical composition comprising a therapeutically effective amount of the compound of the invention and a pharmaceutically acceptable carrier. This invention provides a pharmaceutical composition made by combining a therapeutically effective amount of the compound of this invention and a pharmaceutically acceptable carrier. This invention further provides a process for making a pharmaceutical composition comprising combining a therapeutically effective amount of the compound of the invention and a pharmaceutically acceptable carrier. This invention also provides a method of reducing the body mass of a subject which comprises administering to the subject an amount of a compound of the invention effective to reduce the body mass of the subject. This invention further provides a method of treating a subject suffering from depression and/or anxiety which comprises administering to the subject an amount of a compound of the invention effective to treat the subject's depression and/or anxiety.

27 Claims, No Drawings

SUBSTITUTED ALKYL AMIDO PIPERIDINES

This application is a continuation-in-part of U.S. Ser. No. 10/188,434, filed Jul. 3, 2002, now U.S. Pat. No. 6,727,264, issued Apr. 27, 2004, which claims the benefit of U.S. Provisional Application No. 60/346,997, filed Jan. 9, 2002 and U.S. Provisional Application No. 60/303,091, filed Jul. 5, 2001.

The contents of PCT International Application No. PCT/US02/21063 are hereby incorporated by reference into the subject application.

BACKGROUND OF THE INVENTION

Throughout this application, various publications are referenced in parentheses by author and year. Full citations for these references may be found at the end of the specification immediately preceding the sequence listings and the claims. The disclosure of these publications in their entireties are hereby incorporated by reference into this application to describe more fully the state of the art to which this invention pertains.

Melanin-concentrating hormone (MCH) is a cyclic peptide originally isolated from salmonid (teleost fish) pituitaries (Kawauchi et al., 1983). In fish the 17 amino acid peptide causes aggregation of melanin within the melanophores and inhibits the release of ACTH, acting as a functional antagonist of α-MSH. Mammalian MCH (19 amino acids) is highly conserved between rat, mouse, and human, exhibiting 100% amino acid identity, but its physiological roles are less clear. MCH has been reported to participate in a variety of processes including feeding, water balance, energy metabolism, general arousal/attention state, memory and cognitive functions, and psychiatric disorders (for reviews, see Baker, 1991; Baker, 1994; Nahon, 1994; Knigge et al., 1996). Its role in feeding or body weight regulation is supported by a recent *Nature* publication (Qu et al., 1996) demonstrating that MCH is overexpressed in the hypothalamus of ob/ob mice compared with ob/+ mice, and that fasting further increased MCH mRNA in both obese and normal mice during fasting. MCH also stimulated feeding in normal rats when injected into the lateral ventricles (Rossi et al., 1997). MCH also has been reported to functionally antagonize the behavioral effects of α-MSH (Miller et al., 1993; Gonzalez et al, 1996; Sanchez et al., 1997); in addition, stress has been shown to increase POMC mRNA levels while decreasing the MCH precursor preproMCH (ppMCH) mRNA levels (Presse et al., 1992). Thus MCH may serve as an integrative neuropeptide involved in the reaction to stress, as well as in the regulation of feeding and sexual activity (Baker, 1991; Knigge et al., 1996).

Although the biological effects of MCH are believed to be mediated by specific receptors, binding sites for MCH have not been well described. A tritiated ligand ([$^3$H]-MCH) was reported to exhibit specific binding to brain membranes but was unusable for saturation analyses, so neither affinity nor $B_{max}$ were determined (Drozdz and Eberle, 1995). Radioiodination of the tyrosine at position thirteen resulted in a ligand with dramatically reduced biological activity (see Drozdz and Eberle, 1995). In contrast, the radioiodination of the MCH analogue [Phe$^{13}$,Tyr$^{19}$]-MCH was successful (Drozdz et al., 1995); the ligand retained biological activity and exhibited specific binding to a variety of cell lines including mouse melanoma (B16-F1, G4F, and G4F-7), PC12, and COS cells. In G4F-7 cells, the $K_D$=0.118 nM and the $B_{max}$ ~1100 sites/cell. Importantly, the binding was not inhibited by α-MSH but was weakly inhibited by rat ANF (Ki=116 nM vs. 12 nM for native MCH) (Drozdz et al., 1995). More recently specific MCH binding was reported in transformed keratinocytes (Burgaud et al., 1997) and melanoma cells (Drozdz et al., 1998), where photo-crosslinking studies suggest that the receptor is a membrane protein with an apparent molecular weight of 45–50 kDaltons, compatible with the molecular weight range of the GPCR superfamily of receptors. No radioautoradiographic studies of MCH receptor localization using this ligand have been reported as yet.

The localization and biological activities of MCH peptide suggest that the modulation of MCH receptor activity may be useful in a number of therapeutic applications. The role of MCH in feeding is the best characterized of its potential clinical uses. MCH is expressed in the lateral hypothalamus, a brain area implicated in the regulation of thirst and hunger (Grillon et al., 1997); recently orexins A and B, which are potent orexigenic agents, have been shown to have very similar localization to MCH in the lateral hypothalamus (Sakurai et al., 1998). MCH mRNA levels in this brain region are increased in rats after 24 hours of food-deprivation (Hervé and Fellman, 1997); after insulin injection, a significant increase in the abundance and staining intensity of MCH immunoreactive perikarya and fibres was observed concurrent with a significant increase in the level of MCH mRNA (Bahjaoui-Bouhaddi et al., 1994). Consistent with the ability of MCH to stimulate feeding in rats (Rossi et al., 1997) is the observation that MCH mRNA levels are upregulated in the hypothalami of obese ob/ob mice (Qu et al., 1996), and decreased in the hypothalami of rats treated with leptin, whose food intake and body weight gains are also decreased (Sahu, 1998). MCH appears to act as a functional antagonist of the melanocortin system in its effects on food intake and on hormone secretion within the HPA (hypothalamopituitary/adrenal axis) (Ludwig et al., 1998). Together these data suggest a role for endogenous MCH in the regulation of energy balance and response to stress, and provide a rationale for the development of specific compounds acting at MCH receptors for use in the treatment of obesity and stress-related disorders.

In all species studied to date, a major portion of the neurons of the MCH cell group occupies a rather constant location in those areas of the lateral hypothalamus and subthalamus where they lie and may be a part of some of the so-called "extrapyramidal" motor circuits. These involve substantial striato- and pallidofugal pathways involving the thalamus and cerebral cortex, hypothalamic areas, and reciprocal connections to subthalamic nucleus, substantia nigra, and mid-brain centers (Bittencourt et al., 1992). In their location, the MCH cell group may offer a bridge or mechanism for expressing hypothalamic visceral activity with appropriate and coordinated motor activity. Clinically it may be of some value to consider the involvement of this MCH system in movement disorders, such as Parkinson's disease and Huntingdon's Chorea in which extrapyramidal circuits are known to be involved.

Human genetic linkage studies have located authentic hMCH loci on chromosome 12 (12q23-24) and the variant hMCH loci on chromosome 5 (5q12-13) (Pedeutour et al., 1994). Locus 12q23-24 coincides with a locus to which autosomal dominant cerebellar ataxia type II (SCA2) has been mapped (Auburger et al., 1992; Twells et al., 1992). This disease comprises neurodegenerative disorders, including an olivopontocerebellar atrophy. Furthermore, the gene for Darier's disease, has been mapped to locus 12q23-24 (Craddock et al., 1993). Dariers' disease is characterized by abnormalities I keratinocyte adhesion and mental illnesses in some families. In view of the functional and neuroanatomical patterns of the MCH neural system in the rat and human brains, the MCH gene may represent a good candidate for SCA2 or Darier's disease. Interestingly, diseases with high social impact have been mapped to this locus. Indeed, the gene responsible for chronic or acute forms of spinal muscular atrophies has been assigned to chromosome 5q12-13 using genetic linkage analysis (Melki et al., 1990; Westbrook et al., 1992). Furthermore, independent lines of evidence support the assignment of a major schizophrenia locus to chromosome 5q11.2-13.3 (Sherrington et al., 1988; Bassett et al., 1988; Gilliam et al., 1989). The above studies suggest that MCH may play a role in neurodegenerative diseases and disorders of emotion.

Additional therapeutic applications for MCH-related compounds are suggested by the observed effects of MCH in other biological systems. For example, MCH may regulate reproductive functions in male and female rats. MCH transcripts and MCH peptide were found within germ cells in testes of adult rats, suggesting that MCH may participate in stem cell renewal and/or differentiation of early spermatocytes (Hervieu et al., 1996). MCH injected directly into the medial preoptic area (MPOA) or ventromedial nucleus (VMN) stimulated sexual activity in female rats (Gonzalez et al., 1996). In ovariectomized rats primed with estradiol, MCH stimulated luteinizing hormone (LH) release while anti-MCH antiserum inhibited LH release (Gonzalez et al., 1997). The zona incerta, which contains a large population of MCH cell bodies, has previously been identified as a regulatory site for the pre-ovulatory LH surge (MacKenzie et al., 1984). MCH has been reported to influence release of pituitary hormones including ACTH and oxytocin. MCH analogues may also be useful in treating epilepsy. In the PTZ seizure model, injection of MCH prior to seizure induction prevented seizure activity in both rats and guinea pigs, suggesting that MCH-containing neurons may participate in the neural circuitry underlying PTZ-induced seizure (Knigge and Wagner, 1997). MCH has also been observed to affect behavioral correlates of cognitive functions. MCH treatment hastened extinction of the passive avoidance response in rats (McBride et al., 1994), raising the possibility that MCH receptor antagonists may be beneficial for memory storage and/or retention. A possible role for MCH in the modulation or perception of pain is supported by the dense innervation of the periaqueductal grey (PAG) by MCH-positive fibers. Finally, MCH may participate in the regulation of fluid intake. ICV infusion of MCH in conscious sheep produced diuretic, natriuretic, and kaliuretic changes in response to increased plasma volume (Parkes, 1996). Together with anatomical data reporting the presence of MCH in fluid regulatory areas of the brain, the results indicate that MCH may be an important peptide involved in the central control of fluid homeostasis in mammals.

The identification of a G-protein coupled receptor for MCH has recently been published (Chambers et al., 1999; Saito et al., 1999). These groups identified MCH as the endogenous ligand for the human orphan G-protein coupled receptor SLC-1 (Lakaye et al., 1998). The rat homologue of this receptor (now called MCH-1) was reported to be localized in regions of the rat brain associated with feeding behavior (e.g. dorsomedial and ventromedial hypothalamus). The link between MCH-1 and the effects of MCH on feeding has been strengthened by recent reports on the phenotype of MCH-1 knockout mice. Two groups have shown independently (Marsh et al, 2002; Chen et al, 2002) that the targeted disruption of the MCH-1 receptor gene (MCH-1 knockout) in mice results in animals that are hyperphagic but are lean and have decreased body mass relative to wild-type littermates. The decrease in body mass is attributed to an increase in metabolism. Each group demonstrated that the MCH-1 knockout mice are resistant to diet-induced obesity, and generally exhibit weights similar to littermates maintained on regular chow.

Finally, synthetic antagonist molecules for the MCH-1 receptor have now been described in the literature. Bednarek et al. (2002) have reported on the synthesis of high affinity peptide antagonists of MCH-1. In addition, a small molecule antagonist of MCH-1 has been described by Takekawa et al. (Takekawa et al., 2002). This compound, T-226296, exhibits high affinity for the MCH-1 receptor (~5–9 nM for rat and human MCH-1), and was shown to inhibit food intake induced by the intracerebroventricular application of MCH. These data validate the strategy of using an MCH-1 receptor antagonist to treat obesity.

Furthermore, in our own studies, we have tested MCH-1 antagonists in several animal models that are well known as predictive for the efficacy of compounds in humans, see Borowsky, et al. (2002). These experiments indicate that MCH1 antagonists are useful to treat obesity, depression, anxiety, as well as urinary disorders.

As used in this invention, the term "antagonist" refers to a compound which binds to, and decreases the activity of, a receptor in the presence of an agonist. In the case of a G-protein coupled receptor, activation may be measured using any appropriate second messenger system which is coupled to the receptor in a cell or tissue in which the receptor is expressed. Some specific, but by no means limiting, examples of well-known second messenger systems are adenylate cyclase, intracellular calcium mobilization, ion channel activation, guanylate cyclase and inositol phospholipid hydrolysis. Conversely, the term "agonist" refers to a compound which binds to, and increases activity of, a receptor as compared with the activity of the receptor in the absence of any agonist.

In one embodiment of this invention, the synthesis of novel compounds which bind selectively to the cloned human melanin-concentrating hormone-1 (MCH1) receptor, compared to other cloned G-protein coupled receptors, and inhibit the activation of the cloned receptors as measured in in vitro assays is disclosed. The in vitro receptor binding assays described hereinafter were performed using various cultured cell lines, each transfected with and expressing only a single cloned receptor.

Furthermore, the compounds of the present invention may also be used to treat abnormal conditions such as feeding disorders (obesity, bulimia and bulimia nervosa), sexual/reproductive disorders, depression, anxiety, depression and anxiety, epileptic seizure, hypertension, cerebral hemorrhage, congestive heart failure, sleep disturbances, or any condition in which antagonism of an MCH1 receptor may be beneficial. In addition, the compounds of the present invention may be used to reduce the body mass of a subject. Furthermore, the compounds of the present invention may be used to treat urinary disorders.

SUMMARY OF THE INVENTION

The present invention provides for a compound having the structure:

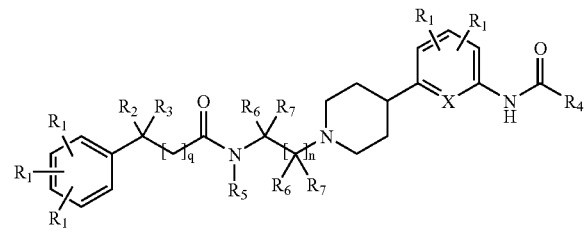

wherein each $R_1$ is independently hydrogen; —F; —Cl; —Br; —I; —CN; —NO$_2$; straight chained or branched $C_1$–$C_7$ alkyl, monofluoroalkyl or polyfluoroalkyl; straight chained or branched $C_2$–$C_7$ alkenyl; $C_3$–$C_7$ cycloalkyl or $C_5$–$C_7$ cycloalkenyl; aryl; heteroaryl; —N(R$_5$)$_2$; —(CH$_2$)$_m$OR$_5$; —COR$_5$; —CO$_2$R$_5$; —OCOR$_5$; —CON(R$_5$)$_2$; —N(R$_5$)COR$_5$; —N(R$_5$)CON(R$_5$)$_2$; —OCON(R$_5$)$_2$ or —N(R$_5$)CO$_2$R$_5$;

wherein $R_2$ and $R_3$ are independently hydrogen; —F; —Cl; —Br; —I; —CN; —(CH$_2$)$_m$OR$_5$; —(CH$_2$)$_m$SR$_5$; straight chained or branched $C_1$–$C_7$ alkyl, monofluoroalkyl, polyfluoroalkyl; aryl or heteroaryl, wherein the aryl or heteroaryl may be substituted with one or more $R_1$; or wherein $R_2$ and $R_3$ together can be —(CH$_2$)$_p$—;

wherein $R_4$ is straight chained or branched $C_1$–$C_7$ alkyl, monofluoroalkyl or polyfluoroalkyl, $C_3$–$C_6$ cycloalkyl, —N(R$_5$)$_2$ or —(CH$_2$)$_m$OR$_5$;

wherein each $R_5$ is independently hydrogen; aryl; heteroaryl or straight chained or branched $C_1$–$C_7$ alkyl, wherein the alkyl may be substituted with aryl or heteroaryl;

wherein each $R_6$ is independently hydrogen; straight chained or branched $C_1$–$C_7$ alkyl;

wherein each $R_7$ is independently hydrogen; phenyl or straight chained or branched $C_1$–$C_7$ alkyl, wherein the alkyl may be substituted with phenyl;

wherein each m is independently an integer from 0 to 5 inclusive;

wherein n is an integer from 1 to 5 inclusive;

wherein p is an integer from 2 to 7 inclusive;

wherein q is an integer from 0 to 2 inclusive;

wherein X is CH or N;

or a pharmaceutically acceptable salt thereof.

In a sub-class of the invention, are the compounds wherein each $R_1$ is independently hydrogen; straight chained or branched $C_1$–$C_7$ alkyl; —F; —Cl; —Br; —I; —CN; —NO$_2$; straight chained or branched $C_1$–$C_4$ alkyl or polyfluoroalkyl; —(CH$_2$)$_m$OR$_5$; —COR$_5$; —CO$_2$R$_5$; —OCOR$_5$; —CON(R$_5$)$_2$; —N(R$_5$)COR$_5$ or —N(R$_5$)CON(R$_5$)$_2$;

wherein $R_2$ and $R_3$ are independently hydrogen; —F; —Cl; —Br; —I; —CN; —(CH$_2$)$_m$SR$_5$; straight chained or branched $C_1$–$C_7$ alkyl; aryl or heteroaryl, wherein the aryl or heteroaryl may be substituted with one or more $R_1$; or wherein $R_2$ and $R_3$ together can be —(CH$_2$)$_p$—;

wherein $R_4$ is straight chained or branched $C_1$–$C_7$ alkyl; $C_3$–$C_6$ cycloalkyl; —N(R$_5$)$_2$ or —(CH$_2$)$_m$OR$_5$;

wherein each $R_5$ is independently hydrogen or straight chained or branched $C_1$–$C_3$ alkyl, wherein the alkyl may be substituted with phenyl;

wherein m is 0 to 3;

wherein n is 1 to 3;

wherein p is an integer from 2 to 5 inclusive;

wherein q is 0; and wherein X is CH.

In a subclass of the invention are the compounds of the formula:

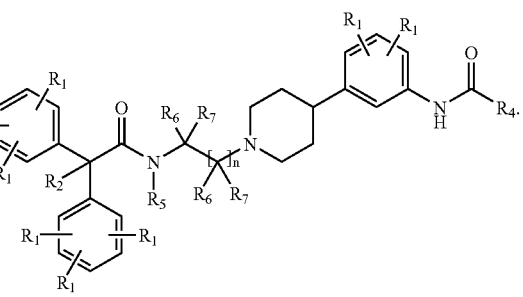

In one embodiment of the invention are the compounds having the following structure:

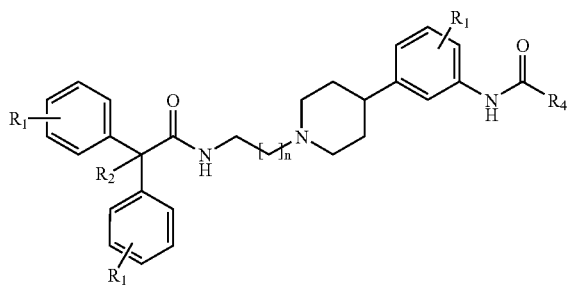

In one embodiment of the invention, $R_1$ is hydrogen; —F; —Cl; —Br; —I or straight chained or branched $C_1$–$C_7$ alkyl; and $R_2$ is hydrogen or straight chained or branched $C_1$–$C_7$ alkyl.

In one embodiment of the invention $R_4$ is straight chained or branched $C_1$–$C_7$ alkyl.

In one embodiment of the invention, the compound has the structure:

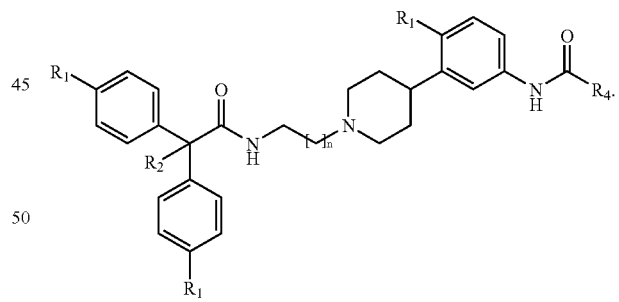

In one embodiment of the invention, the compound is selected from the group consisting of:

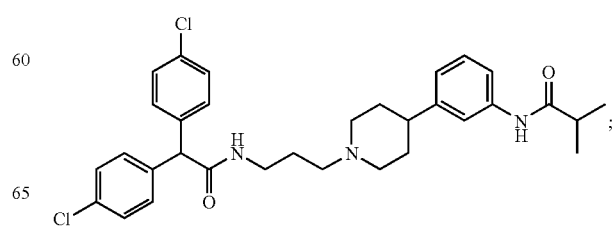

-continued

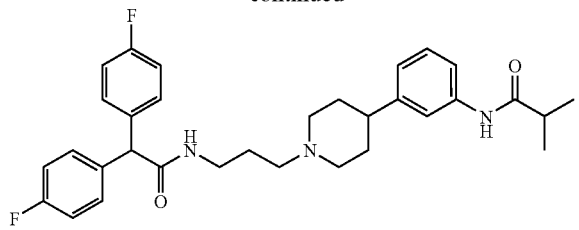

or

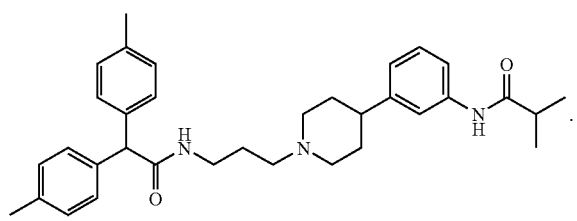

In one embodiment of the invention, the compound is selected from the group consisting of:

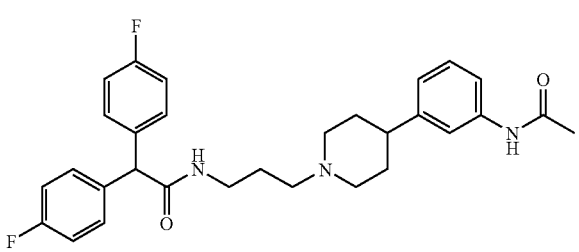

or

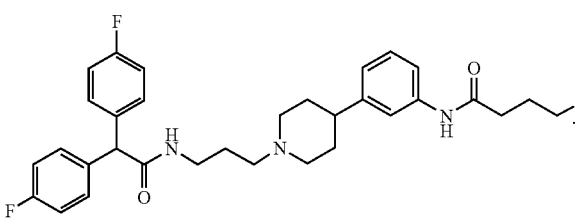

In one embodiment of the invention, the compound is selected from the group consisting of:

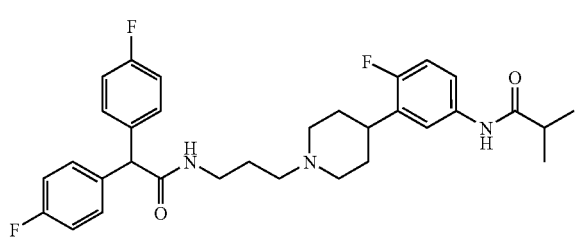

or

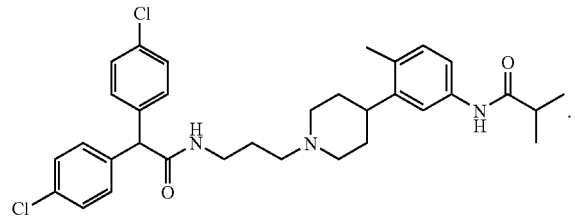

In one embodiment of the invention, $R_4$ is $C_3$–$C_6$ cycloalkyl.

In one embodiment of the invention, the compound is selected from the group consisting of:

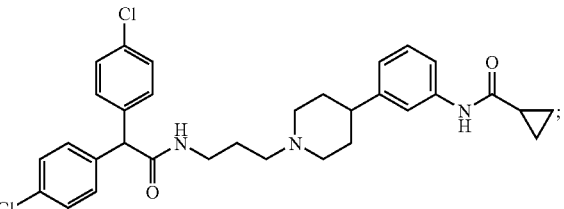

or

In one embodiment of the invention, $R_2$ and $R_3$ are independently hydrogen; —F; —Br or straight chained or branched $C_1$–$C_7$ alkyl.

In one embodiment of the invention, $R_2$ and $R_3$ are independently hydrogen or straight chained or branched $C_1$–$C_7$ alkyl.

In one embodiment of the invention, the compound is selected from the group consisting of:

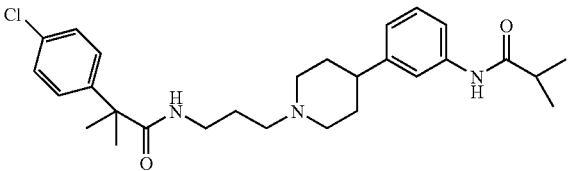

or

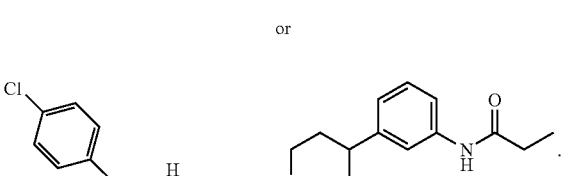

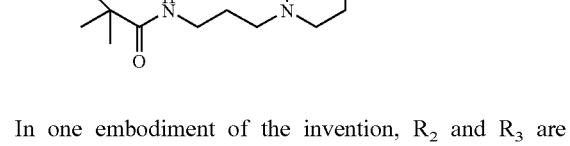

In one embodiment of the invention, $R_2$ and $R_3$ are independently hydrogen; —F or —Br.

In one embodiment of the invention, the compound has the structure:

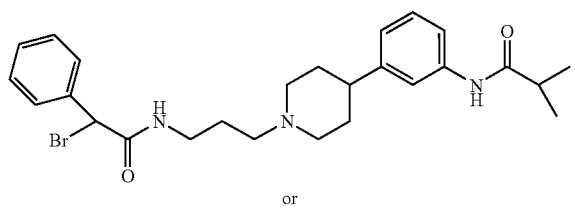

or

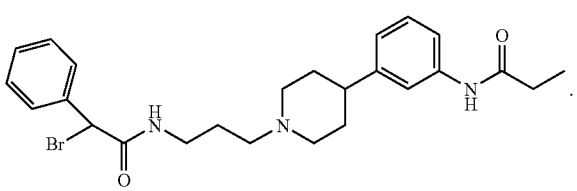

In one embodiment of the invention, $R_2$ and $R_3$ together are $-(CH_2)_p-$;

In one embodiment of the invention, the compound has the structure:

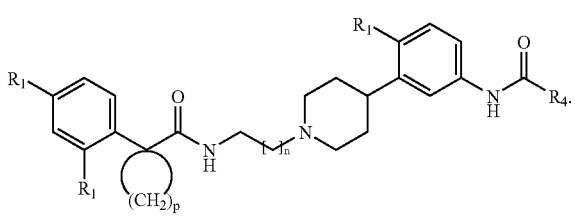

In one embodiment of the invention, $R_4$ is straight chained or branched $C_1$–$C_7$ alkyl.

In one embodiment of the invention, the compound is selected from the group consisting of:

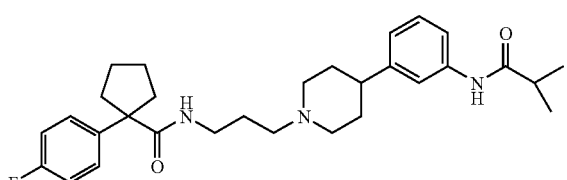

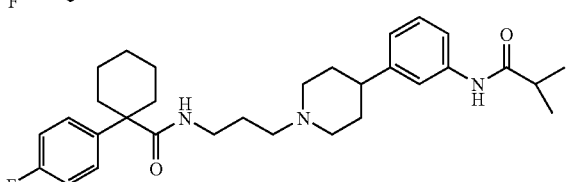

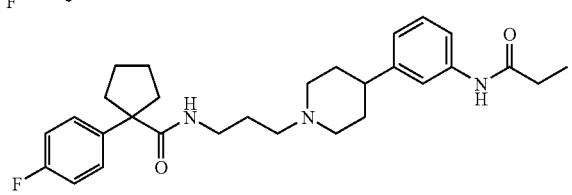

or

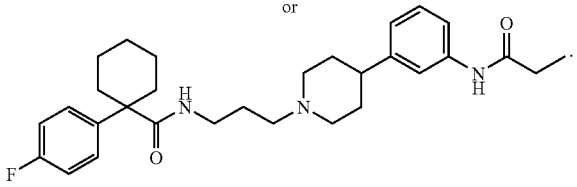

In one embodiment of the invention, the compound is selected from the group consisting of:

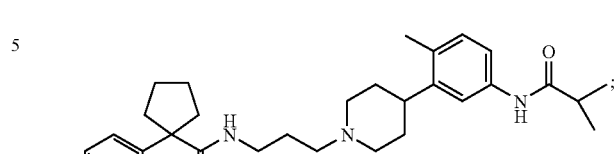

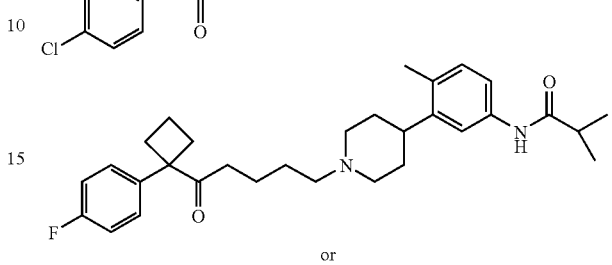

or

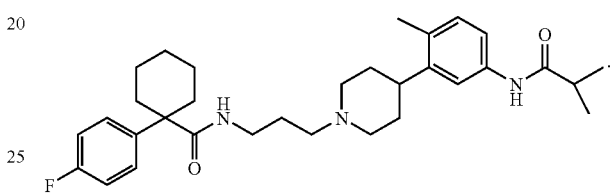

In one embodiment of the invention, the compound has the following structure:

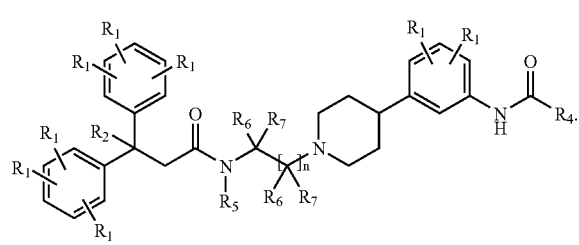

In one embodiment of the invention, the compound has the following structure:

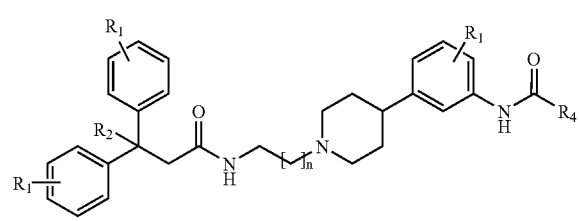

In one embodiment of the invention, the compound has the structure:

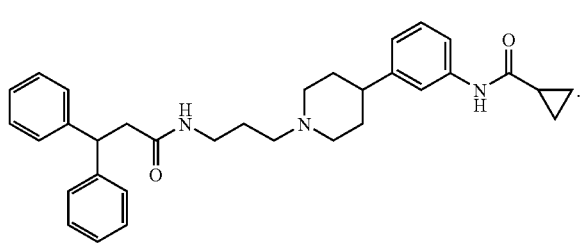

In one embodiment of the invention, the compound is enantiomerically pure.

In one embodiment of the invention, the compound is diastereomerically pure.

In one embodiment of the invention, the compound is enantiomerically and diastereomerically pure.

The present invention also provides a pharmaceutical composition that comprises a therapeutically effective amount of a compound of the present invention and a pharmaceutically acceptable carrier.

The present invention further provides a pharmaceutical composition made by admixing a compound of the present invention and a pharmaceutically acceptable carrier.

The present invention also provides a process for making a pharmaceutical composition comprising admixing a compound of the present invention and a pharmaceutically acceptable carrier.

The present invention also provides a method for treating a subject suffering from a disorder mediated by the MCH1 receptor comprising administering to the subject a therapeutically effective amount of a compound of the present invention.

In one embodiment, the therapeutically effective amount is between about 0.03 and about 300 mg.

In one embodiment, the disorder is depression, anxiety, obesity or urge incontinence.

The present invention also provides a method of treating a subject suffering from a disorder selected from the group consisting of depression, anxiety, urge incontinence or obesity comprising administering to the subject a therapeutically effective amount of a compound of the present invention.

DETAILED DESCRIPTION OF THE INVENTION

As used in the present invention, the term "heteroaryl" is used to include five and six membered unsaturated rings that may contain one or more oxygen, sulfur, or nitrogen atoms. Examples of heteroaryl groups include, but are not limited to, carbazole, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition, the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, CN, —NO$_2$, straight chained or branched $C_1$–$C_7$ alkyl, straight chained or branched $C_1$–$C_7$ monofluoroalkyl, straight chained or branched $C_1$–$C_7$ polyfluoroalkyl, straight chained or branched $C_2$–$C_7$ alkenyl, straight chained or branched $C_2$–$C_7$ alkynyl; $C_3$–$C_7$ cycloalkyl, $C_3$–$C_7$ monofluorocycloalkyl, $C_3$–$C_7$ polyfluorocycloalkyl, $C_5$–$C_7$ cycloalkenyl.

The term "heteroaryl" further includes the N-oxides of those chemical moieties recited above which include at least one nitrogen atom.

In the present invention, the term "aryl" is phenyl or naphthyl.

The invention provides for each pure stereoisomer of any of the compounds described herein. Such stereoisomers may include enantiomers, diastereomers, or E or Z alkene or imine isomers. The invention also provides for stereoisomeric mixtures, including racemic mixtures, diastereomeric mixtures, or E/Z isomeric mixtures. Stereoisomers can be synthesized in pure form (Nógrádi, M.; *Stereoselective Synthesis*, (1987) VCH Editor Ebel, H. and *Asymmetric Synthesis*, Volumes 3 B 5, (1983) Academic Press, Editor Morrison, J.) or they can be resolved by a variety of methods such as crystallization and chromatographic techniques (Jaques, J.; Collet, A.; Wilen, S.; *Enantiomer, Racemates, and Resolutions*, 1981, John Wiley and Sons and *Asymmetric Synthesis*, Vol. 2, 1983, Academic Press, Editor Morrison, J).

In addition the compounds of the present invention may be present as enantiomers, diasteriomers, isomers or two or more of the compounds may be present to form a racemic or diastereomeric mixture.

The compounds of the present invention are preferably 80% pure, more preferably 90% pure, and most preferably 95% pure. Included in this invention are pharmaceutically acceptable salts and complexes of all of the compounds described herein. The acids and bases from which these salts are prepared include but are not limited to the acids and bases listed herein. The acids include, but are not limited to, the following inorganic acids: hydrochloric acid, hydrobromic acid, hydroiodic acid, sulfuric acid and boric acid. The acids include, but are not limited to, the following organic acids: acetic acid, malonic acid, succinic acid, fumaric acid, tartaric acid, maleic acid, citric acid, methanesulfonic acid, benzoic acid, glycolic acid, lactic acid and mandelic acid. The bases include, but are not limited to ammonia, methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The present invention includes within its scope prodrugs of the compounds of the invention. In general, such prodrugs will be functional derivatives of the compounds of the invention which are readily convertible in vivo into the required compound. Thus, in the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

This invention further provides a pharmaceutical composition comprising a therapeutically effective amount of the compound of the invention and a pharmaceutically acceptable carrier. In one embodiment, the amount of the compound is from about 0.01 mg to about 800 mg. In another embodiment, the amount of the compound is from about 0.01 mg to about 500 mg. In yet another embodiment, the amount of the compound is from about 0.1 mg to about 250 mg. In another embodiment, the amount of the compound is from about 0.1 mg to about 60 mg. In yet another embodiment, the amount of the compound is from about 1 mg to about 20 mg. In a further embodiment, the carrier is a liquid and the composition is a solution. In another embodiment, the carrier is a solid and the composition is a tablet. In another embodiment, the carrier is a gel and the composition is a capsule, suppository or a cream. In a further embodiment the compound may be formulated as a part of a pharmaceutically acceptable transdermal patch. In yet a further embodiment, the compound may be delivered to the subject by means of a spray or inhalant.

This invention also provides a pharmaceutical composition made by combining a therapeutically effective amount of the compound of this invention and a pharmaceutically acceptable carrier.

This invention provides a process for making a pharmaceutical composition comprising combining a therapeutically effective amount of the compound of this invention and a pharmaceutically acceptable carrier.

A solid carrier can include one or more substances which may also act as endogenous carriers (e.g. nutrient or micronutrient carriers), flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, coloring agents, viscosity regulators, stabilizers or osmoregulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate or isopropyl myristate. Sterile liquid carriers are useful in sterile liquid form compositions for parenteral administration. The liquid carrier for pressurized compositions can be a halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings. The compound can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

In the subject application a "therapeutically effective amount" is any amount of a compound which, when administered to a subject suffering from a disease against which the compounds are effective, causes reduction, remission, or regression of the disease. In a subject application, a "subject" is a vertebrate, a mammal or a human.

This invention provides a method of treating a subject suffering from an abnormality wherein the abnormality is alleviated by decreasing the activity of an MCH1 receptor which comprises administering to the subject an amount of a compound of the invention which is an MCH1 receptor antagonist effective to treat the subject=s abnormality.

In separate embodiments, the abnormality is a regulation of a steroid or pituitary hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder such as Alzheimer=s disease, a sensory modulation and transmission disorder, a motor coordination disorder, a sensory integration disorder, a motor integration disorder, a dopaminergic function disorder such as Parkinson=s disease, a sensory transmission disorder, an olfaction disorder, a sympathetic innervation disorder, an affective disorder such as depression and anxiety, a stress-related disorder, a fluid-balance disorder, a seizure disorder, pain, psychotic behavior such as schizophrenia, morphine tolerance, opiate addiction, migraine or a urinary disorder such as urinary incontinence.

The following description of depressive and anxiety disorders is for the purpose of illustrating the utility of the compounds of this invention. The definitions of depressive and anxiety disorders given below are those listed in Diagnostic and Statistical Manual of Mental Disorders. 4th ed. (DSM-IV; American Psychiatric Association, 1994a) or Diagnostic and Statistical Manual of Mental Disorders. 3rd ed. Revised (DSM-III-R; American Psychiatric Association, 1987). Additional information regarding these disorders can be found in this reference, as well as the others cited below, all of which are incorporated herein by reference.

Depressive disorders include major depressive disorder and dysthymic disorder (American Psychiatric Association, 1994a; American Psychiatric Association, 1994b). Major depressive disorder is characterized by the occurrence of one or more major depressive episodes without manic or hypomanic episodes. A major depressive episode is defined as a prominent and relatively persistent depressed or dysphoric mood that usually interferes with daily functioning (nearly every day for at least 2 weeks); it should include at least 4 of the following 8 symptoms: change in appetite, change in sleep, psychomotor agitation or retardation, loss of interest in usual activities or decrease in sexual drive, increased fatigue, feelings of guilt or worthlessness, slowed thinking or impaired concentration, and a suicide attempt or suicidal ideation (Medical Economics Company, 2002). Dysthymic disorder involves a type of depression that is not severe enough to be called a major depressive episode, but that lasts much longer than major depressive disorder, without high phases.

It is contemplated that the compounds of this invention will be effective in treating depression in patients who have been diagnosed with depression by administration of any of the following tests: Hamilton Depression Rating Scale (HDRS), Hamilton depressed mood item, Clinical Global Impressions (CGI)-Severity of Illness. It is further contemplated that the compounds of the invention will be effective in inducing improvements in certain of the factors measured in these tests, such as the HDRS subfactor scores, including the depressed mood item, sleep disturbance factor and anxiety factor, and the CGI-Severity of Illness rating. It is also contemplated that the compounds of this invention will be effective in preventing relapse of major depressive episodes.

Anxiety disorders include panic disorder, agoraphobia with or without history of panic disorder, specific phobia, social phobia, obsessive-compulsive disorder, post-traumatic stress disorder, acute stress disorder and generalized anxiety disorder. It is contemplated that the compounds of this invention will be effective in treating any of all of these disorders in patients who have been diagnosed with these disorders.

Obsessive compulsive disorder is characterized by recurrent and persistent ideas, thoughts, impulses or images (obsessions) that are ego-dystonic and/or repetitive, purposeful and intentional behaviors (compulsions) that are recognized by the person as excessive or unreasonable (American Psychiatric Association, 1994a). The obsessions or compulsions cause marked distress, are time-consuming, or significantly interfere with social or occupational functioning.

It is contemplated that the compounds of this invention will be effective in treating obsessions and compulsions in patients who have been diagnosed with obsessive compulsive disorder by administration of appropriate tests, which may include, but are not limited to any of the following: Yale Brown Obsessive Compulsive Scale (YBOCS) (Goodman, 1989) (for adults), National Institute of Mental Health Global OCD Scale (NIMH GOCS), CGI-Severity of Illness scale. It is further contemplated that the compounds of the invention will be effective in inducing improvements in certain of the factors measured in these tests, such as a reduction of several points in the YBOCS total score. It is also contemplated that the compounds of this invention will be effective in preventing relapse of obsessive compulsive disorder.

Panic disorder is characterized by recurrent unexpected panic attacks and associated concern about having additional attacks, worry about the implications or consequences of the attacks, and/or a significant change in behavior related to the attacks (American Psychiatric Association, 1994a). A panic attack is defined as a discrete period of intense fear or discomfort in which four (or more) of the following symptoms develop abruptly and reach a peak within 10 minutes: (1) palpitations, pounding heart, or accelerated heart rate; (2) sweating; (3) trembling or shaking; (4) sensations of shortness of breath or smothering; (5) feeling of choking; (6) chest pain or discomfort; (7) nausea or abdominal distress; (8) feeling dizzy, unsteady, lightheaded, or faint; (9) derealization (feelings of unreality) or depersonalization (being detached from oneself); fear of losing control; (11) fear of dying; (12) paresthesias (numbness or tingling sensations); (13) chills or hot flushes. Panic disorder may or may not be associated with agoraphobia, or an irrational and often disabling fear of being out in public.

It is contemplated that the compounds of this invention will be effective in treating panic disorder in patients who have been diagnosed with panic disorder on the basis of frequency of occurrence of panic attacks, or by means of the CGI-Severity of Illness scale. It is further contemplated that the compounds of the invention will be effective in inducing improvements in certain of the factors measured in these evaluations, such as a reduction in frequency or elimination of panic attacks, an improvement in the CGI-Severity of Illness scale or a CGI-Global Improvement score of 1 (very much improved), 2 (much improved) or 3 (minimally improved). It is also contemplated that the compounds of this invention will be effective in preventing relapse of panic disorder.

Social anxiety disorder, also known as social phobia, is characterized by a marked and persistent fear of one or more social or performance situations in which the person is exposed to unfamiliar people or to possible scrutiny by others (American Psychiatric Association, 1994a). Exposure to the feared situation almost invariably provokes anxiety, which may approach the intensity of a panic attack. The feared situations are avoided or endured with intense anxiety or distress. The avoidance, anxious anticipation, or distress in the feared situation(s) interferes significantly with the person's normal routine, occupational or academic functioning, or social activities or relationships, or there is marked distress about having the phobias Lesser degrees of performance anxiety or shyness generally do not require psychopharmacological treatment.

It is contemplated that the compounds of this invention will be effective in treating social anxiety disorder in patients who have been diagnosed with social anxiety disorder by administration of any of the following tests: the Liebowitz Social Anxiety Scale (LSAS), the CGI-Severity of Illness scale, the Hamilton Rating Scale for Anxiety (HAM-A), the Hamilton Rating Scale for Depression (HAM-D), the axis V Social and Occupational Functioning Assessment Scale of DSM-IV, the axis II (ICD-10) World Health Organization Disability Assessment, Schedule 2 (DAS-2), the Sheehan Disability Scales, the Schneier Disability Profile, the World Health Organization Quality of Life-100 (WHOQOL-100), or other tests as described in Bobes, 1998, which is incorporated herein by reference. It is further contemplated that the compounds of the invention will be effective in inducing improvements as measured by these tests, such as the a change from baseline in the Liebowitz Social Anxiety Scale (LSAS), or a CGI-Global Improvement score of 1 (very much improved), 2 (much improved) or 3 (minimally improved). It is also contemplated that the compounds of this invention will be effective in preventing relapse of social anxiety disorder.

Generalized anxiety disorder is characterized by excessive anxiety and worry (apprehensive expectation) that is persistent for at least 6 months and which the person finds difficult to control (American Psychiatric Association, 1994a). It must be associated with at least 3 of the following 6 symptoms: restlessness or feeling keyed up or on edge, being easily fatigued, difficulty concentrating or mind going blank, irritability, muscle tension, sleep disturbance. The diagnostic criteria for this disorder are described in further detail in DSM-IV, which is incorporated herein by reference (American Psychiatric Association, 1994a).

It is contemplated that the compounds of this invention will be effective in treating generalized anxiety disorder in patients who have been diagnosed with this disorder according to the diagnostic criteria described in DSM-IV. It is further contemplated that the compounds of the invention will be effective in reducing symptoms of this disorder, such as the following: excessive worry and anxiety, difficulty controlling worry, restlessness or feeling keyed up or on edge, being easily fatigued, difficulty concentrating or mind going blank, irritability, muscle tension, or sleep disturbance. It is also contemplated that the compounds of this invention will be effective in preventing relapse of general anxiety disorder.

Post-traumatic stress disorder (PTSD), as defined by DSM-III-R/IV (American Psychiatric Association, 1987, American Psychiatric Association, 1994a), requires exposure to a traumatic event that involved actual or threatened death or serious injury, or threat to the physical integrity of self or others, and a response which involves intense fear, helplessness, or horror. Symptoms that occur as a result of exposure to the traumatic event include re-experiencing of the event in the form of intrusive thoughts, flashbacks or dreams, and intense psychological distress and physiological reactivity on exposure to cues to the event; avoidance of situations reminiscent of the traumatic event, inability to recall details of the event, and/or numbing of general responsiveness manifested as diminished interest in significant activities, estrangement from others, restricted range of affect, or sense of foreshortened future; and symptoms of autonomic arousal including hypervigilance, exaggerated startle response, sleep disturbance, impaired concentration, and irritability or outbursts of anger. A PTSD diagnosis requires that the symptoms are present for at least a month and that they cause clinically significant distress or impairment in social, occupational, or other important areas of functioning.

It is contemplated that the compounds of this invention will be effective in treating PTSD in patients who have been diagnosed with PTSD by administration of any of the following tests: Clinician-Administered PTSD Scale Part 2 (CAPS), the patient-rated Impact of Event Scale (IES) (Medical Economics Company, 2002, p. 2752). It is further contemplated that the compounds of the invention will be effective in inducing improvements in the scores of the CAPS, IES, CGI-Severity of Illness or CGI-Global Improvement tests. It is also contemplated that the compounds of this invention will be effective in preventing relapse of PTSD.

In a preferred embodiment, the subject invention provides a method of treatment or management of the following indications: depressive disorders, anxiety disorders, eating/body weight disorders, and urinary disorders. Examples of depressive disorders are major depressive disorder or dysthymic disorder. Examples of anxiety disorders are panic disorder, agoraphobia without history of panic disorder, specific phobia, social phobia, obsessive-compulsive disorder, post-traumatic stress disorder, acute stress disorder or generalized anxiety disorder. Examples of eating/body weight disorders are obesity, weight gain, bulimia, bulimia nervosa or anorexia nervosa. Examples of urinary disorders include, but are not limited to urinary incontinence overactive bladder, urge incontinence, urinary frequency, urinary urgency, nocturia or enuresis. Overactive bladder and urinary urgency may or may not be associated with benign prostatic hyperplasia.

This invention provides a method of modifying the feeding behavior of a subject, which comprises administering to the subject an amount of a compound of the invention effective to decrease the consumption of food by the subject. This invention also provides a method of treating an eating disorder in a subject, which comprises administering to the subject an amount of a compound of the invention effective to treat the eating disorder. In an embodiment of the present invention, the eating disorder is obesity, bulimia, bulimia nervosa or anorexia nervosa.

The present invention further provides a method of reducing the body mass of a subject, which comprises administering to the subject an amount of a compound of the invention effective to reduce the body mass of the subject. This invention also provides a method of managing obesity in a subject in need of weight loss, which comprises administering to the subject an amount of a compound of the invention effective to induce weight loss in the subject. This invention also provides a method of managing obesity in a subject who has experienced weight loss, which comprises administering to the subject an amount of a compound of the invention effective to maintain such weight loss in the subject.

The present invention also provides a method of treating depression in a subject, which comprises administering to the subject an amount of a compound of the invention effective to treat the subject's depression. This invention also provides a method of treating anxiety in a subject, which comprises administering to the subject an amount of a compound of the invention effective to treat the subject's anxiety. This invention also provides a method of treating depression and anxiety in a subject, which comprises administering to the subject an amount of a compound of the invention effective to treat the subject's depression and anxiety. This invention also provides a method of treating major depressive disorder in a subject, which comprises administering to the subject an amount of a compound of the invention effective to treat the subject's major depressive disorder. This invention also provides a method of treating dysthymic disorder in a subject, which comprises administering to the subject an amount of a compound of the invention effective to treat the subject's dysthymic disorder. This invention also provides a method of treating obsessions and compulsions in a subject with obsessive compulsive disorder, which comprises administering to the subject an amount of a compound of the invention effective to treat the subject's obsessions and compulsions. This invention also provides a method of treating panic disorder, with or without agoraphobia, in a subject, which comprises administering to the subject an amount of a compound of the invention effective to treat the subject's panic disorder. This invention also provides a method of treating social anxiety disorder in a subject, which comprises administering to the subject an amount of a compound of the invention effective to treat the subject's social anxiety disorder. This invention also provides a method of treating generalized anxiety disorder in a subject, which comprises administering to the subject an amount of a compound of the invention effective to treat the subject's generalized anxiety disorder. This invention also provides a method of treating post-traumatic stress disorder in a subject, which comprises administering to the subject an amount of a compound of the invention effective to treat the subject's post-traumatic stress disorder.

It is contemplated that the compounds of this invention will be effective in treating obesity, including weight loss and maintenance of weight loss in patients, who have been diagnosed with obesity by the one or more of the following measurements: an increased body mass index, increased waist circumference (an indicator of intra-adominal fat), Dual Energy X-Ray Absorptiometry (DEXA) and trucal (android) fat mass. It is further contemplated that the compounds of the invention will be effective in inducing improvements in certain factors measured in these tests.

It is contemplated that the compounds of this invention will be effective in treating urinary disorders in patients who have urge or mixed (with a predominance of urge) incontinence as evidenced by the number of unnecessary episodes per week, the number of unnecessary micturitions per day and a low volume voided per micturition. It is further contemplated that the compounds of the invention will be effective in inducing improvements in certain factors measured in these tests.

The present invention also provides a method of treating a subject suffering from bipolar I or II disorder, schizoaffective disorder, a cognitive disorder with depressed mood, a personality disorder, insomnia, hypersomnia, narcolepsy, circadian rhythm sleep disorder, nightmare disorder, sleep terror disorder or sleepwalking disorder.

The present invention provides a method of treating overactive bladder with symptoms of urge urinary incontinence, urgency and/or frequency in a subject, which comprises administering to the subject an amount of a compound of the invention effective to treat the subject's overactive bladder. This invention also provides a method of alleviating urge urinary incontinence in a subject suffering from overactive bladder, which comprises administering to the subject an amount of a compound of the invention effective to alleviate the subject's urge urinary incontinence. This invention further provides a method of alleviating urinary urgency in a subject suffering from overactive bladder, which comprises administering to the subject an amount of a compound of the invention effective to alleviate the subject's urinary urgency. Additionally, this invention provides a method of alleviating urinary frequency in a subject suffering from overactive bladder, which comprises administering to the subject an amount of a compound of the invention effective to alleviate the subject's urinary frequency.

The present invention also provides a method of treating a subject suffering from a urinary disorder, which comprises administering to the subject an amount of a compound of the invention effective to treat the subject's urinary disorder. In some embodiments the urinary disorder is urinary incontinence, overactive bladder, urge incontinence, urinary frequency, urinary urgency, nocturia or enuresis.

The present invention provides a method of alleviating the symptoms of a disorder in a subject, which comprises administering to the subject an amount of an MCH1 antagonist effective to alleviate the symptoms, wherein the MCH1 antagonist is any of the compounds of the invention.

In an embodiment of the invention, the subject is a vertebrate, a mammal, a human or a canine. In another embodiment, the compound is administered orally. In yet another embodiment, the compound is administered in combination with food.

This invention will be better understood from the Experimental Details In a preferred embodiment, the subject invention provides a method of treatment for the following indications: depression, anxiety, eating/body weight disorders, and urinary disorders. Examples of eating/body weight disorders are obesity, bulimia, or bulimia nervosa. Examples of urinary disorders include, but are not limited to, urinary incontinence, overactive bladder, urge incontinence, urinary frequency, urinary urgency, nocturia, or enuresis. Overactive bladder and urinary urgency may or may not be associated with benign prostatic hyperplasia.

This invention provides a method of modifying the feeding behavior of a subject which comprises administering to the subject an amount of a compound of the invention effective to decrease the consumption of food by the subject.

This invention also provides a method of treating an eating disorder in a subject which comprises administering to the subject an amount of a compound of this invention effective to decrease the consumption of food by the subject. In an embodiment of the present invention, the eating disorder is bulimia, obesity or bulimia nervosa. In an embodiment of the present invention, the subject is a vertebrate, a mammal, a human or a canine. In a further embodiment, the compound is administered in combination with food.

The present invention further provides a method of reducing the body mass of a subject which comprises administering to the subject an amount of a compound of the invention effective to reduce the body mass of the subject.

The present invention also provides a method of treating a subject suffering from depression which comprises administering to the subject an amount of a compound of this invention effective to treat the subject's depression. The present invention further provides a method of treating a subject suffering from anxiety which comprises administering to the subject an amount of a compound of this invention effective to treat the subject's anxiety. The present invention also provides a method of treating a subject suffering from depression and anxiety which comprises administering to the subject an amount of a compound of this invention effective to treat the subject's depression and anxiety.

The present invention also provides a method of treating a subject suffering from major depressive disorder, dysthymic disorder, bipolar I and II disorders, schizoaffective disorder, cognitive disorders with depressed mood, personality disorders, insomnia, hypersomnia, narcolepsy, circadian rhythm sleep disorder, nightmare disorder, sleep terror disorder, sleepwalking disorder, obsessive-compulsive disorder, panic disorder, with or without agoraphobia, posttraumatic stress disorder, social anxiety disorder, social phobia and generalized anxiety disorder.

The present invention also provides a method of treating a subject suffering from a urinary disorder which comprises administering to the subject an amount of a compound of this invention effective to treat the subject's a urinary disorder. In some embodiments, the urinary disorder is urinary incontinence, overactive bladder, urge incontinence, urinary frequency, urinary urgency, nocturia, or enuresis.

This invention will be better understood from the Experimental Details which follow. However, one skilled in the art will readily appreciate that the specific methods and results discussed are merely illustrative of the invention as described more fully in the claims which follow thereafter.

The present invention further provides for a compound having the structure:

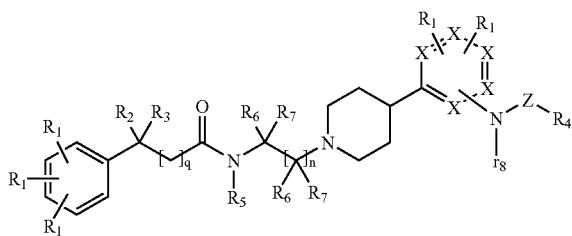

wherein each $R_1$ is independently hydrogen; —F; —Cl; —Br; —I; —CN; —NO$_2$; straight chained or branched $C_1$–$C_7$ alkyl, monofluoroalkyl or polyfluoroalkyl; straight chained or branched $C_2$–$C_7$ alkenyl; $C_3$–$C_7$ cycloalkyl or $C_5$–$C_7$ cycloalkenyl; aryl; heteroaryl; —N(R$_5$)$_2$; —(CH$_2$)$_m$OR$_5$; —COR$_5$; —CO$_2$R$_5$; —OCOR$_5$; —CON(R$_5$)$_2$; —N(R$_5$)COR$_5$; —N(R$_5$)CON(R$_5$)$_2$; —OCON(R$_5$)$_2$ or —N(R$_5$)CO$_2$R$_5$;

wherein $R_2$ and $R_3$ are independently hydrogen; —F; —Cl; —Br; —I; —CN; —(CH$_2$)$_m$OR$_5$; —(CH$_2$)$_m$SR$_5$; straight chained or branched $C_1$–$C_7$ alkyl, monofluoroalkyl, polyfluoroalkyl; aryl or heteroaryl, wherein the aryl or heteroaryl may be substituted with one or more $R_1$; or wherein $R_2$ and $R_3$ together can be —(CH$_2$)$_p$—;

wherein $R_4$ is hydrogen; straight chained or branched $C_1$–$C_7$ alkyl, monofluoroalkyl or polyfluoroalkyl; $C_3$–$C_6$ cycloalkyl; —N(R$_5$)$_2$ or —(CH$_2$)$_m$OR$_5$;

wherein each $R_5$ is independently hydrogen; aryl; heteroaryl or straight chained or branched $C_1$–$C_7$ alkyl, wherein the alkyl may be substituted with aryl or heteroaryl;

wherein each $R_6$ is independently hydrogen; straight chained or branched $C_1$–$C_7$ alkyl;

wherein each $R_7$ is independently hydrogen; phenyl or straight chained or branched $C_1$–$C_7$ alkyl, wherein the alkyl may be substituted with phenyl;

wherein $R_8$ is hydrogen or straight chained $C_1$–$C_7$ alkyl;

wherein $R_4$ and $R_8$ together can be —(CH$_2$)$_r$—;

wherein each m is independently an integer from 0 to 5 inclusive;

wherein n is an integer from 1 to 5 inclusive;

wherein p is an integer from 2 to 7 inclusive;

wherein q is an integer from 0 to 2 inclusive;

wherein each X is independently CH or N;

wherein Z is CO; SO2 or may be absent or a pharmaceutically acceptable salt thereof.

The present invention provides for a compound having the structure:

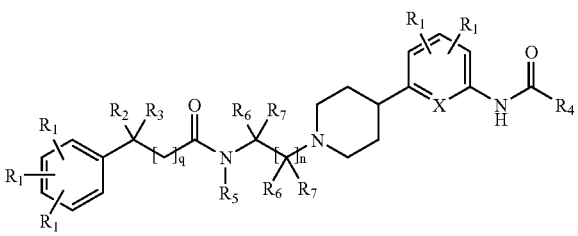

wherein each $R_1$ is independently hydrogen; —F; —Cl; —Br; —I; —CN; —NO$_2$; straight chained or branched $C_1$–$C_7$ alkyl, monofluoroalkyl or polyfluoroalkyl; straight chained or branched $C_2$–$C_7$ alkenyl; $C_3$–$C_7$ cycloalkyl or $C_5$–$C_7$ cycloalkenyl; aryl; heteroaryl; —N(R$_5$)$_2$; —(CH$_2$)$_m$OR$_5$; —COR$_5$; —CO$_2$R$_5$; —OCOR$_5$; —CON(R$_5$)$_2$; —N(R$_5$)COR$_5$; —N(R$_5$)CON(R$_5$)$_2$; —OCON(R$_5$)$_2$ or —N(R$_5$)CO$_2$R$_5$;

wherein $R_2$ and $R_3$ are independently hydrogen; —F; —Cl; —Br; —I; —CN; —(CH$_2$)$_m$OR$_5$; —(CH$_2$)$_m$SR$_5$; straight chained or branched $C_1$–$C_7$ alkyl, monofluoroalkyl, polyfluoroalkyl; aryl or heteroaryl, wherein the aryl or heteroaryl may be substituted with one or more $R_1$; or wherein $R_2$ and $R_3$ together can be —(CH$_2$)$_p$—;

wherein $R_4$ is straight chained or branched $C_1$–$C_7$ alkyl, monofluoroalkyl or polyfluoroalkyl, $C_3$–$C_6$ cycloalkyl, —N(R$_5$)$_2$ or —(CH$_2$)$_m$OR$_5$;

wherein each $R_5$ is independently hydrogen; aryl; heteroaryl or straight chained or branched $C_1$–$C_7$ alkyl, wherein the alkyl may be substituted with aryl or heteroaryl;

wherein each $R_6$ is independently hydrogen; straight chained or branched $C_1$–$C_7$ alkyl;

wherein each $R_7$ is independently hydrogen; phenyl or straight chained or branched $C_1$–$C_7$ alkyl, wherein the alkyl may be substituted with phenyl;

wherein each m is independently an integer from 0 to 5 inclusive;

wherein n is an integer from 1 to 5 inclusive;

wherein p is an integer from 2 to 7 inclusive;

wherein q is an integer from 0 to 2 inclusive;

wherein X is CH or N;

or a pharmaceutically acceptable salt thereof.

In a sub-class of the invention, are the compounds wherein each $R_1$ is independently hydrogen; straight chained or branched $C_1$–$C_7$ alkyl; —F; —Cl; —Br; —I; —CN; —NO$_2$; straight chained or branched $C_1$–$C_4$ alkyl or polyfluoroalkyl; —(CH$_2$)$_m$OR$_5$; —COR$_5$; —CO$_2$R$_5$; —OCOR$_5$; —CON(R$_5$)$_2$; —N(R$_5$)COR$_5$ or —N(R$_5$)CON(R$_5$)$_2$;

wherein $R_2$ and $R_3$ are independently hydrogen; —F; —Cl; —Br; —I; —CN; —(CH$_2$)$_m$SR$_5$; straight chained or branched $C_1$–$C_7$ alkyl; aryl or heteroaryl, wherein the aryl or heteroaryl may be substituted with one or more $R_1$; or wherein $R_2$ and $R_3$ together can be —(CH$_2$)$_p$—;

wherein $R_4$ is straight chained or branched $C_1$–$C_7$ alkyl; $C_3$–$C_6$ cycloalkyl; —N(R$_5$)$_2$ or —(CH$_2$)$_m$OR$_5$;

wherein each $R_5$ is independently hydrogen or straight chained or branched $C_1$–$C_3$ alkyl, wherein the alkyl may be substituted with phenyl;

wherein m is 0 to 3;

wherein n is 1 to 3;

wherein p is an integer from 2 to 5 inclusive;

wherein q is 0; and wherein X is CH.

In a subclass of the invention are the compounds of the formula:

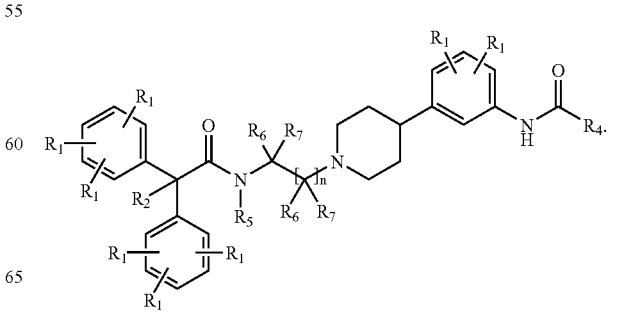

In one embodiment of the invention are the compounds having the following structure:

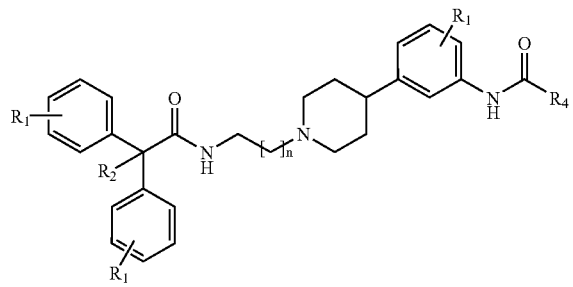

In one embodiment of the invention, $R_1$ is hydrogen; —F; —Cl; —Br; —I or straight chained or branched $C_1$–$C_7$ alkyl; and $R_2$ is hydrogen or straight chained or branched $C_1$–$C_7$ alkyl.

In one embodiment of the invention $R_4$ is straight chained or branched $C_1$–$C_7$ alkyl.

In one embodiment of the invention, the compound has the structure:

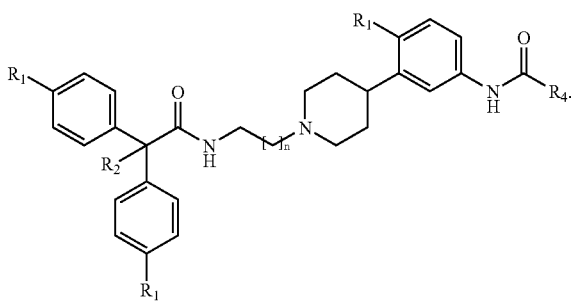

In one embodiment of the invention, the compound is selected from the group consisting of:

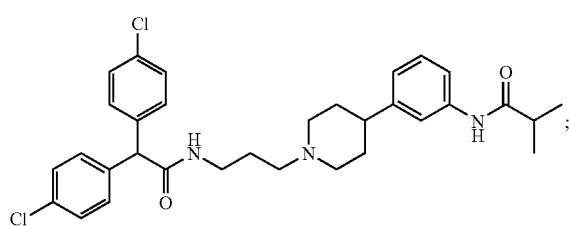

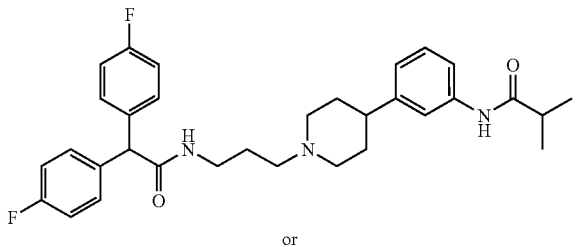

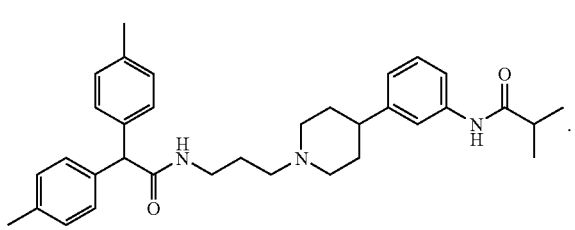

In one embodiment of the invention, the compound is selected from the group consisting of:

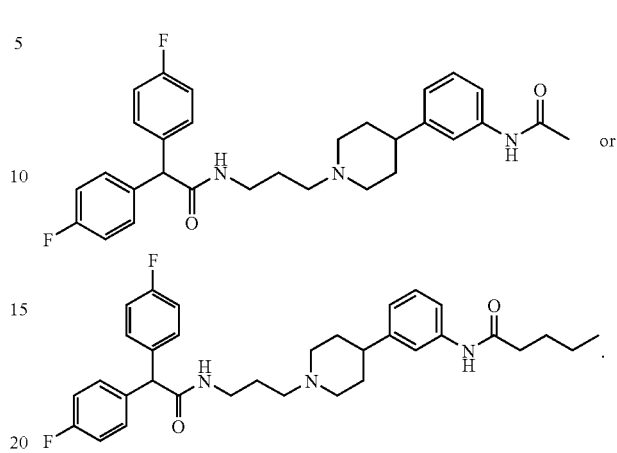

In one embodiment of the invention, the compound is selected from the group consisting of:

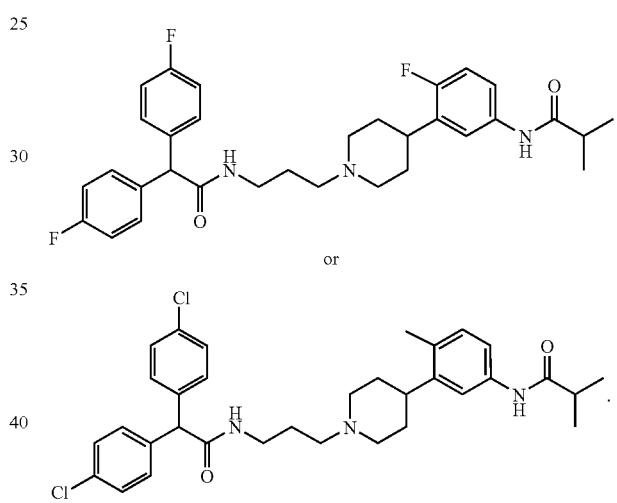

In one embodiment of the invention, $R_4$ is $C_3$–$C_6$ cycloalkyl.

In one embodiment of the invention, the compound is selected from the group consisting of:

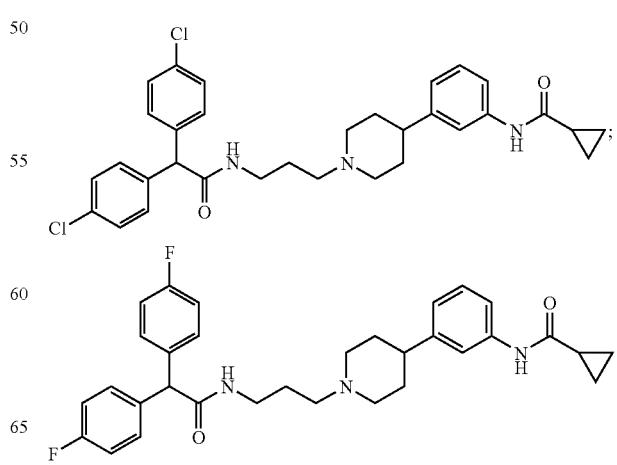

or

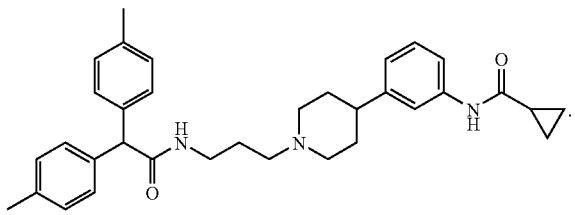

In one embodiment of the invention, $R_2$ and $R_3$ are independently hydrogen; —F; —Br or straight chained or branched $C_1$–$C_7$ alkyl.

In one embodiment of the invention, $R_2$ and $R_3$ are independently hydrogen or straight chained or branched $C_1$–$C_7$ alkyl.

In one embodiment of the invention, the compound is selected from the group consisting of:

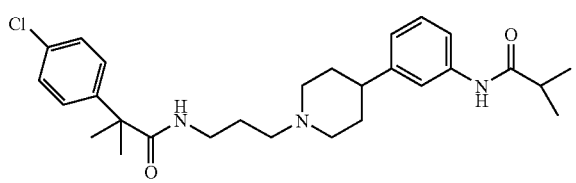

or

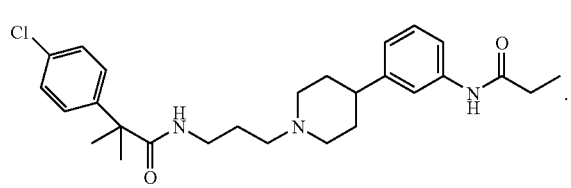

In one embodiment of the invention, $R_2$ and $R_3$ are independently hydrogen; —F or —Br.

In one embodiment of the invention, the compound has the structure:

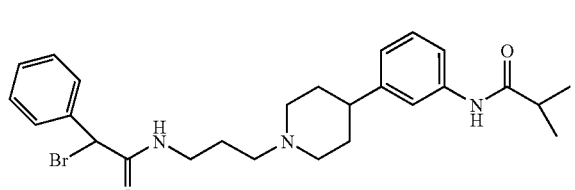

or

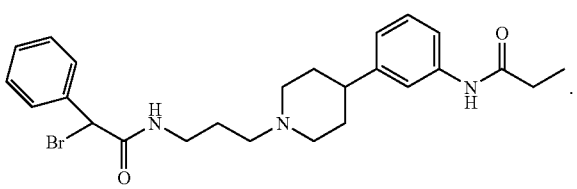

In one embodiment of the invention, $R_2$ and $R_3$ together are —$(CH_2)_p$—;

In one embodiment of the invention, the compound has the structure:

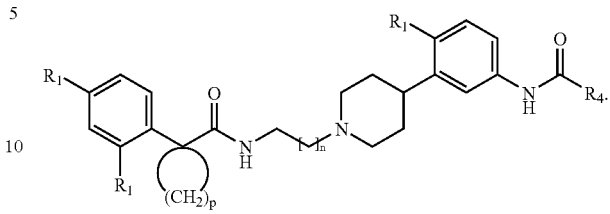

In one embodiment of the invention, $R_4$ is straight chained or branched $C_1$–$C_7$ alkyl.

In one embodiment of the invention, the compound is selected from the group consisting of:

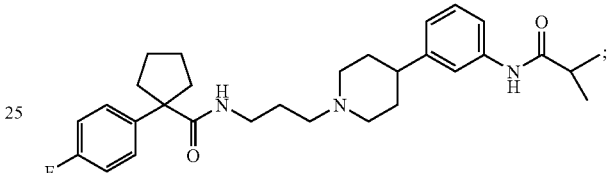

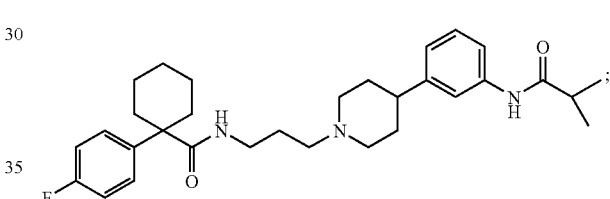

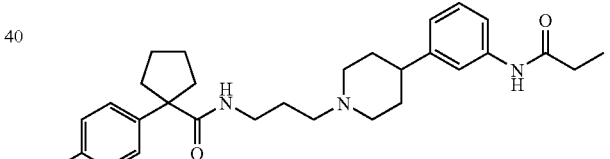

or

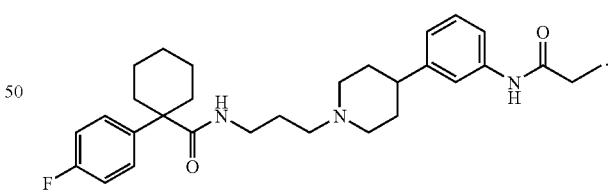

In one embodiment of the invention, the compound is selected from the group consisting of:

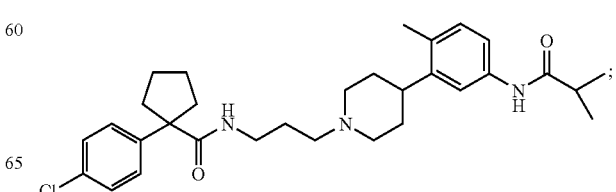

-continued

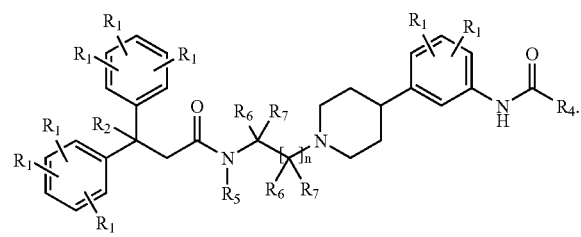

or

In one embodiment of the invention, the compound has the following structure:

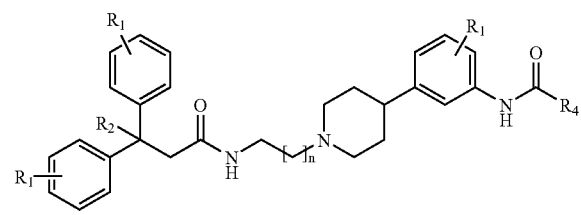

In one embodiment of the invention, the compound has the following structure:

In one embodiment of the invention, the compound has the structure:

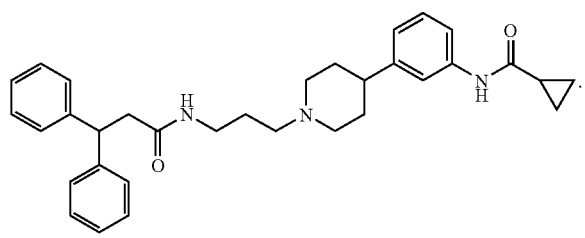

In one embodiment of the invention, the compound is enantiomerically pure.

In one embodiment of the invention, the compound is diastereomerically pure.

In one embodiment of the invention, the compound is enantiomerically and diastereomerically pure.

The present invention also provides a pharmaceutical composition that comprises a therapeutically effective amount of a compound of the present invention and a pharmaceutically acceptable carrier.

The present invention further provides a pharmaceutical composition made by admixing a compound of the present invention and a pharmaceutically acceptable carrier.

The present invention also provides a process for making a pharmaceutical composition comprising admixing a compound of the present invention and a pharmaceutically acceptable carrier.

The present invention also provides a method for treating a subject suffering from a disorder mediated by the MCH1 receptor comprising administering to the subject a therapeutically effective amount of a compound of the present invention.

In one embodiment, the therapeutically effective amount is between about 0.03 and about 300 mg.

In one embodiment, the disorder is depression, anxiety, obesity or urge incontinence.

The present invention also provides a method of treating a subject suffering from a disorder selected from the group consisting of depression, anxiety, urge incontinence or obesity comprising administering to the subject a therapeutically effective amount of a compound of the present invention.

EXPERIMENTAL SECTION

I. Synthetic Methods for Examples

General Methods: All reactions (except for those done by parallel synthesis reaction arrays) were performed under an Argon atmosphere and the reagents, neat or in appropriate solvents, were transferred to the reaction vessel via syringe and cannula techniques. The parallel synthesis reaction arrays were performed in vials (without an inert atmosphere) using J-KEM heating shakers (Saint Louis, Mo.). Anhydrous solvents were purchased from Aldrich Chemical Company and used as received. The compounds described herein were named using ACD/Name program (version 4.0, Advanced Chemistry Development Inc., Toronto, Ontario, M5H2L3, Canada). The $^1$H NMR spectra were recorded at 400 MHz using a Brüker Avance spectrometer with tetramethylsilane as internal standard. Splitting patterns were designated as follows: s=singlet; d=doublet; t=triplet; q=quartet; quintet; sextet; septet; br=broad; m=multiplet. Elemental analyses were performed by Robertson Microlit Laboratories, Inc. Mass spectra were obtained on a Platform II (Fisons) or Quattro Micro (Micromass) spectrometer with electrospray (ESMS) ionization and MH$^+$ is reported. Thin-layer chromatography (TLC) was carried out on glass plates precoated with silica gel 60 F$_{254}$ (0.25 mm, EM Separations Tech.). Preparative thin-layer chromatography was carried out on glass sheets precoated with silica gel GF (2 mm, Analtech). Flash column chromatography was performed on Merck silica gel 60 (230–400 mesh) Melting points (mp) were determined in open capillary tubes on a Mel-Temp apparatus and are uncorrected.

The examples described in the experimental section are merely illustrative of the methods used to synthesize MCH1 antagonists. Additional compounds of the invention can be obtained by the general synthetic procedures described herein or by incorporating variations into these methods that would be obvious to someone skilled in the art.

Scheme 1
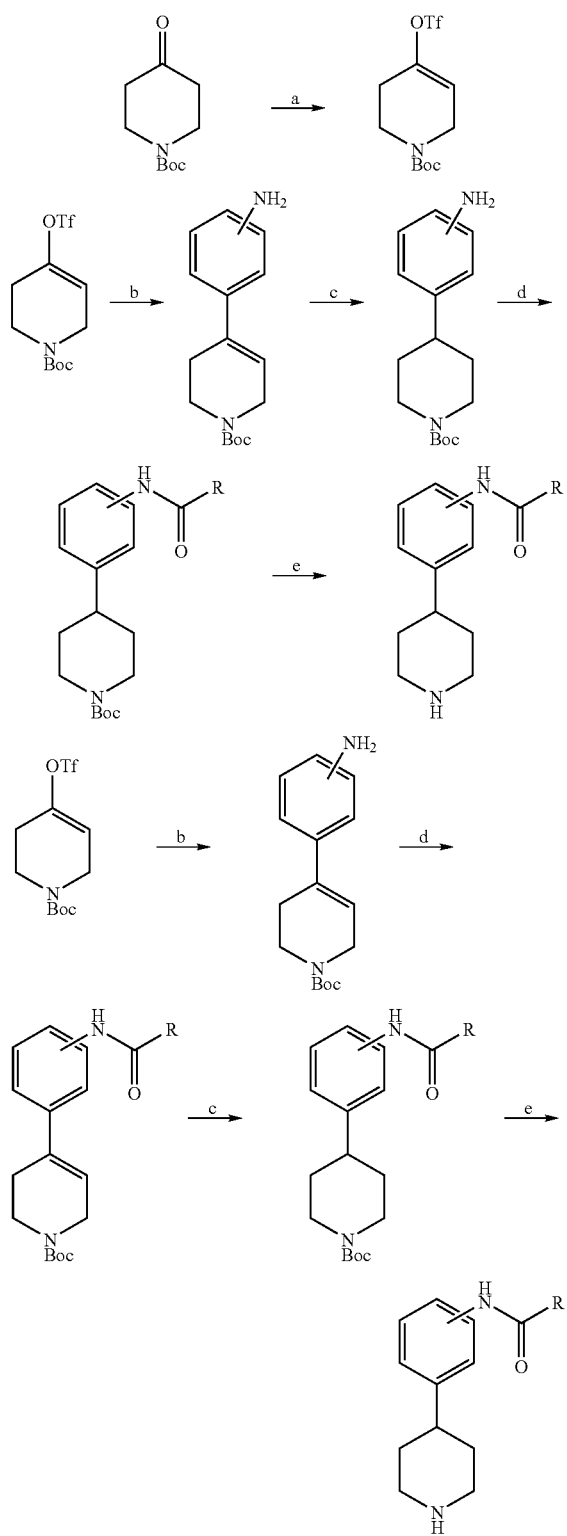
(a) LDA/PhNTf$_2$/THF/-78° C. then 0° C. overnight.
(b) Aminophenylboronic acid/Pd(PPh)$_4$/LiCl/Na$_2$CO$_3$/DME-H$_2$O/reflux 3 h.
(c) 10% Pd/C/H$_2$/EtOH/rt 24–48 h.
(d) Acid chloride or carbamoyl chloride or chloroformate/base/THF/0° C. then rt 2–3 h.
(e) 4M HCl in 1,4-dioxane/rt 1 h or TFA/CH$_2$Cl$_2$/rt 1–2 h.
Scheme 2
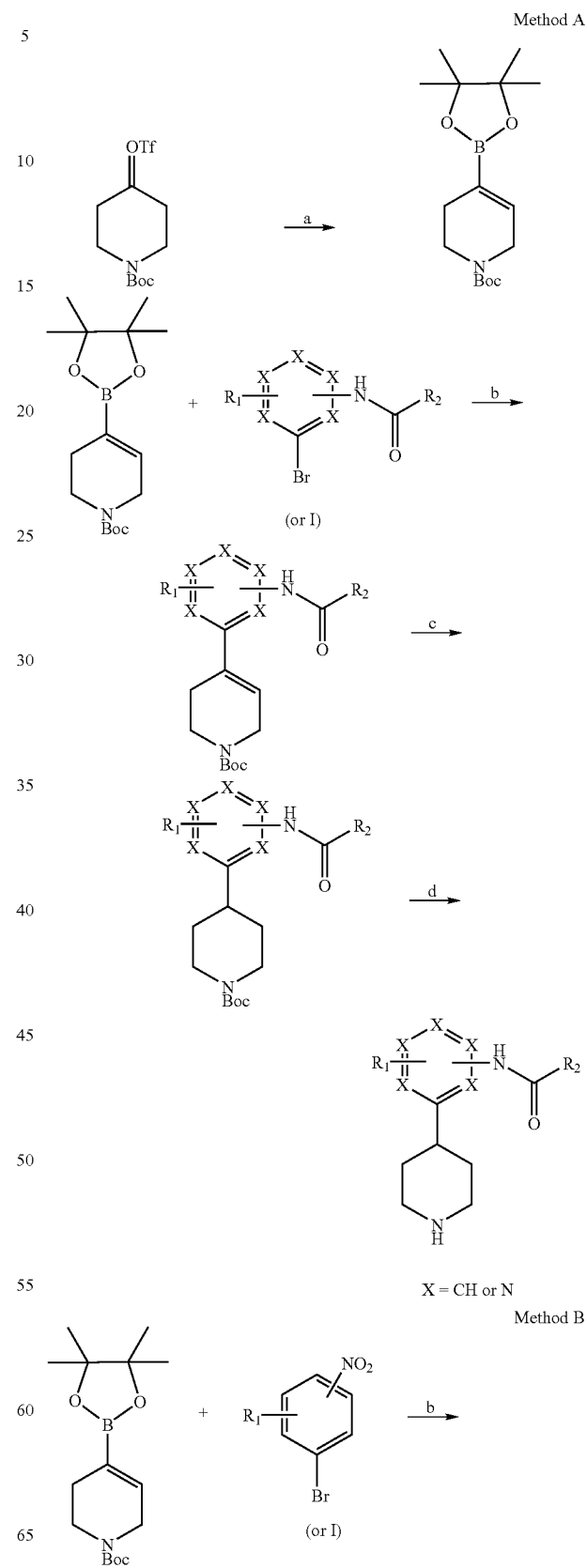
X = CH or N (a) Bis(pinacolato)diboron/KOAc/PdCl₂dppf/dppf/80° C. overnight.
(b) K₂CO₃/PdCl₂dppf/DMF/80° C. overnight.
(c) 10% Pd/C/H₂/EtOH/rt 24h–72 h.
(d) 4M HCl in 1,4-dioxane/rt 1 h or TFA/CH₂Cl₂/rt 1–2 h.
(e) Acid chloride/Et₃N/THF/0° C. then rt 2–3 h.

Scheme 3

Method A

Method B

X = CH or N (a) Di-tert-butyl dicarbonate/K₂CO₃/EtOH/rt overnight.
(b) tert-Butyl N-(3-bromopropyl) carbamate/K₂CO₃/NaI/DMF/80–100° C. overnight.
(c) 4M HCl in 1,4-dioxane/0° C. 1 h or TFA/CH₂Cl₂/rt 1–2 h.
(d) N-(n-bromoalkyl) phthalimide/K₂CO₃/NaI/DMF/90° C. 5h.
(e) N-(n-bromoalkyl) phthalimide/diisopropylethylamine/Bu₄NI/dioxane/100° C. 24 h.
(f) hydrazine hydrate/EtOH/reflux 4 h.

Scheme 4

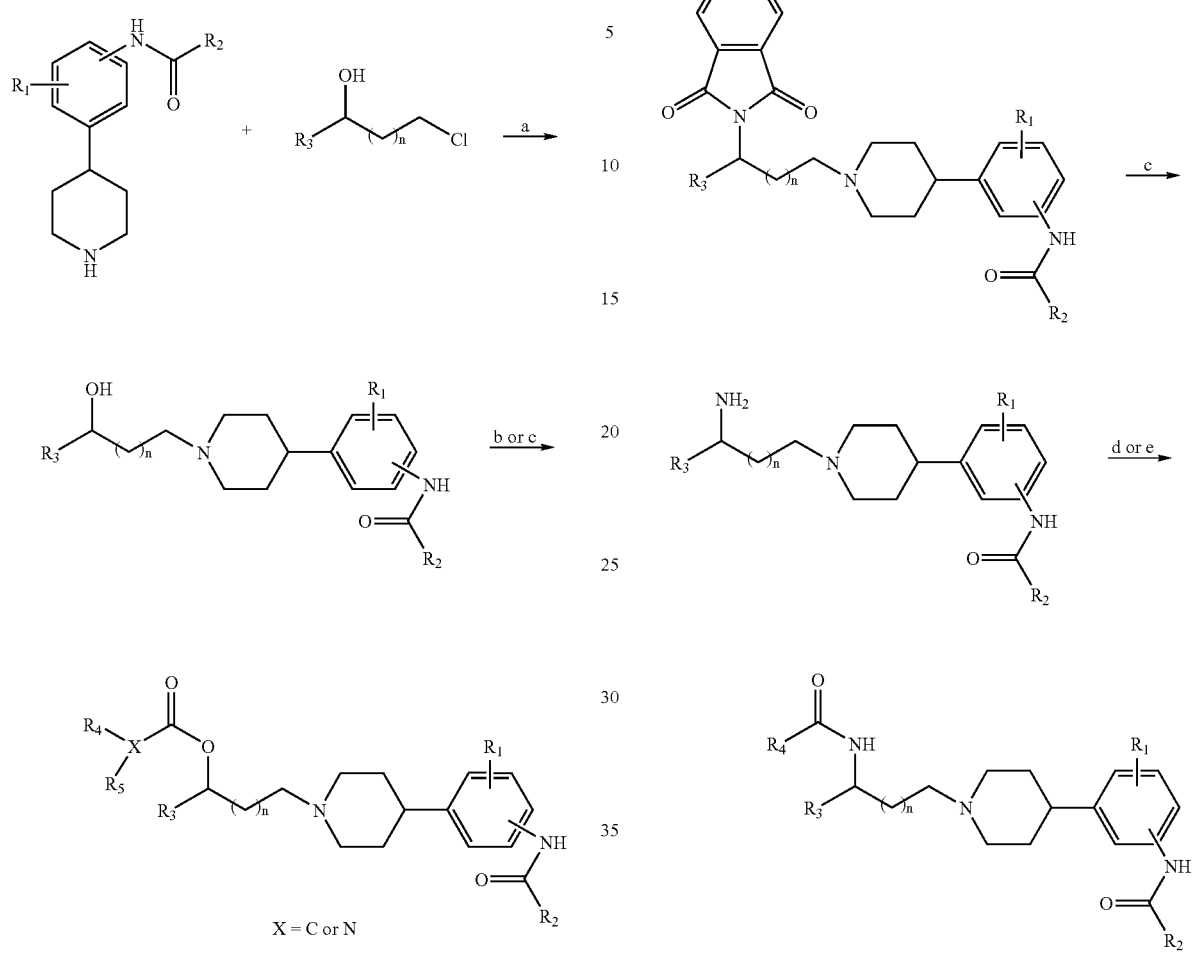

(a) NaI/K$_2$CO$_3$/DMF/80–100° C. overnight or diisopropylethylamine/Bu$_4$NI/dioxane/ 100° C. 3h.
(b) acid chloride/base/CH$_2$Cl$_2$/rt 2h.
(c) acid/coupling reagent/DMF/CH$_2$Cl$_2$/rt overnight.

(a) phthalimide/DEAD/PPh$_3$/THF/rt overnight.
(b) NaI/K$_2$CO$_3$/DMF/80–100° C. overnight or diisopropylethylamine/Bu$_4$NI/dioxane/ reflux overnight.
(c) hydrazine hydrate/EtOH/reflux 4 h.
(d) Acid chloride or carbamoyl chloride or chloroformate/base/THF/0° C. then rt 2–3 h.
(e) acid/coupling reagent/DMF/CH$_2$Cl$_2$/rt overnight.

Scheme 5

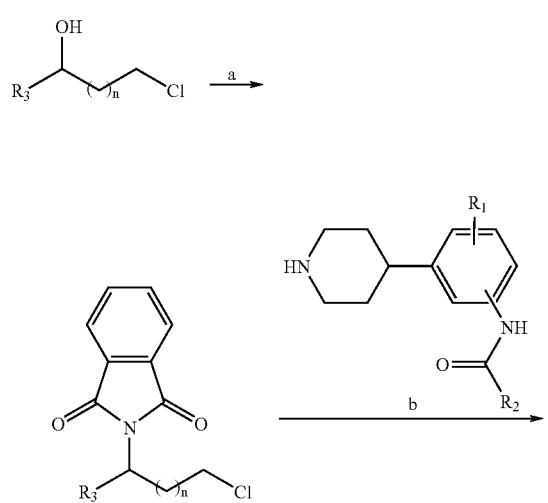

Scheme 6

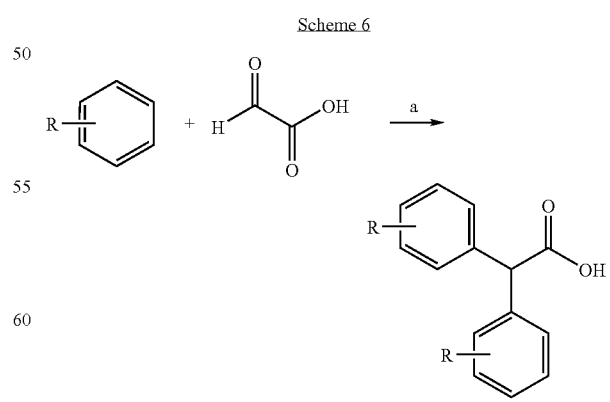

(a) HOAc/H$_2$SO$_4$/80° C. overnight.

Reference for the procedure: Clarke, L.F.; Hegarty, A.F.; O'Neill, P.J. Org. Chem. 1992, 57, 362–366.

Scheme 7
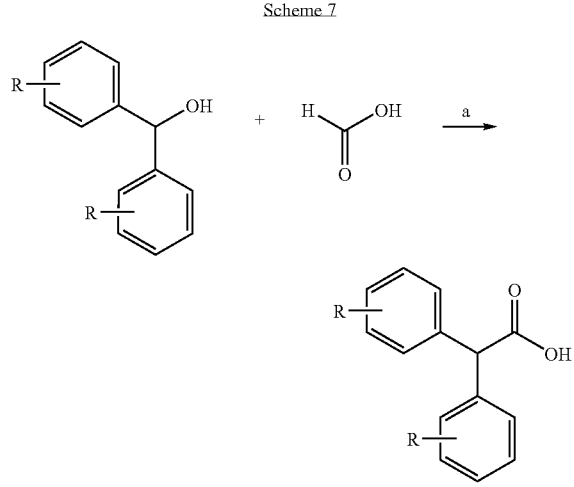
(a) H₂SO₄/15° C./2h.
Reference for the procedure: Takahashi, Y.; Yoneda, N.; Nagai, H. Chem. Lett. 1985, 1733–1734.
Scheme 8
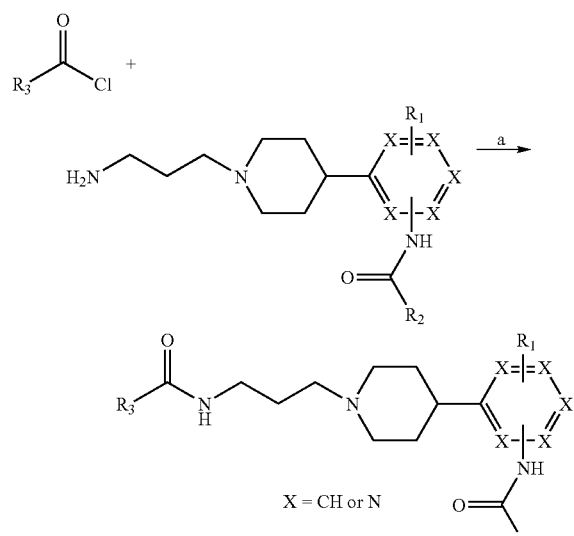
(a) Acid chloride or carbamoyl chloride or chloroformate/base/CH₂Cl₂ or THF/ 0° C. then rt 12 h.
Scheme 9
R₃COOH +
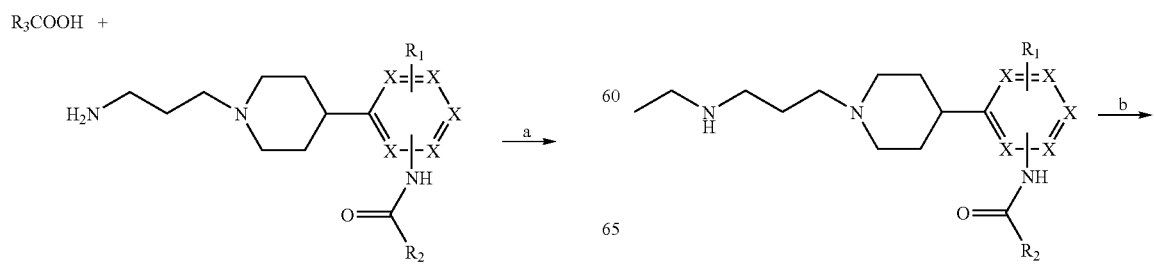
-continued
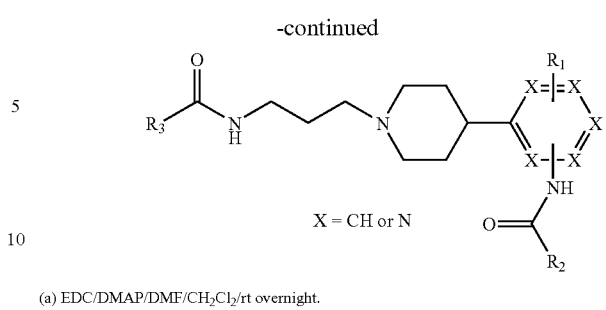
(a) EDC/DMAP/DMF/CH₂Cl₂/rt overnight.
Scheme 10
R₃COOH +
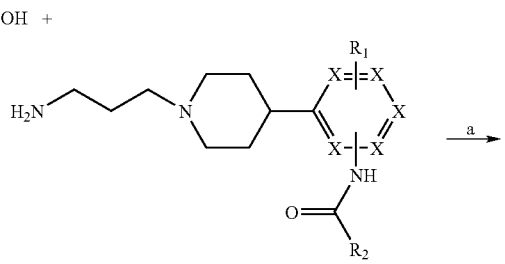
(a) PS-carbodimide/DMF/CH₂Cl₂/rt overnight.
Scheme 13

-continued

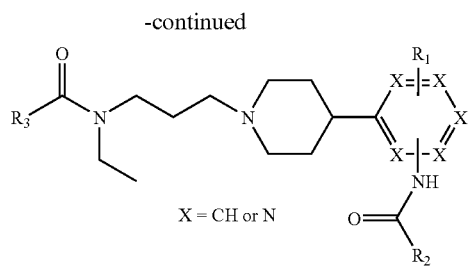

X = CH or N (a) EtI/t-BuONa/THF/rt overnight.
(b) R₃COOH/EDC/DMAP/CH₂Cl₂/DMF.

Scheme 15

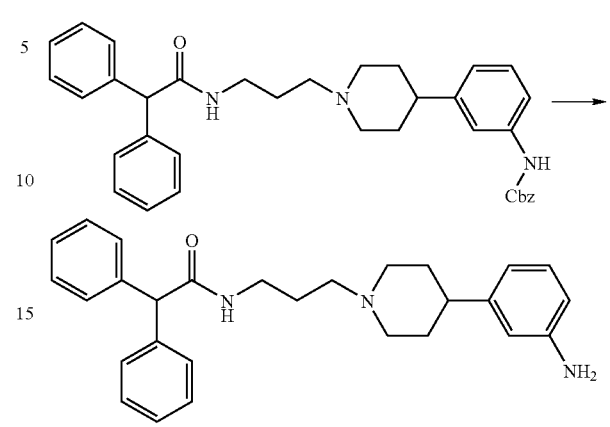

(a) H₂, Pd/C, EtOH, rt 12 h.

Scheme 14

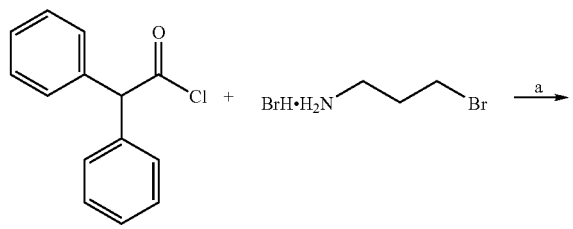

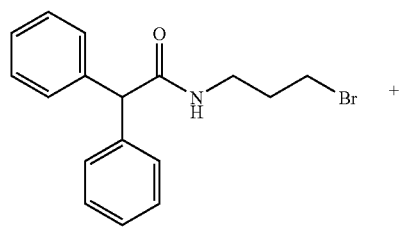

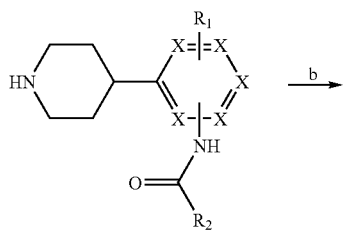

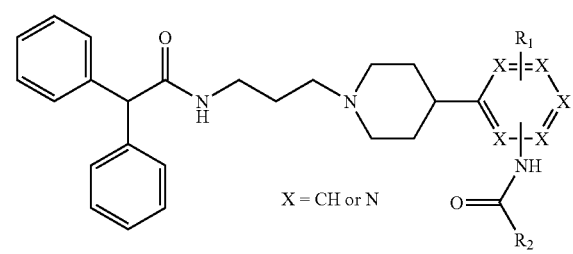

X = CH or N (a) Et₃N/CH₂Cl₂/rt 40 min.
(b) K₂CO₃/NaI/DMF/80–100° C. overnight.

EXAMPLE 1

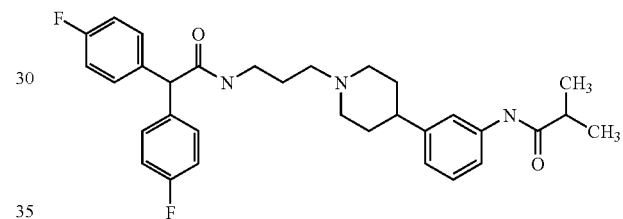

N-{3-[1-(3-{[BIS(4-FLUOROPHENYL)ACETYL]AMINO}PROPYL)-4-PIPERIDINYL]PHENYL}-2-METHYLPROPANAMIDE

Example 1 was prepared from bis(4-fluorophenyl)acetic acid and N-{3-[1-(3-aminopropyl)-4-piperidinyl]phenyl}-2-methylpropanamide according to the procedures described in Scheme 9: $^1$H NMR (400 MHz, CDCl₃) δ 7.63 (s, 1H), 7.39–7.31 (m, 3H), 7.29–7.21 (m, 5H), 7.02–6.96 (m, 4H), 4.80 (s, 1H), 3.40 (q, 2H, J=4.5 Hz), 2.94 (d, 2H, J=10.2 Hz), 2.51–2.38 (m, 4H), 1.97 (dt, 2H, J=1.8, 10.4 Hz), 1.81 (m, 2H), 1.68 (quintet, 2H, J=6.8 Hz,), 1.59 (m, 3H), 1.23 (d, 6H, J=6.9 Hz); ESMS m/e: 534.3 (M+H)⁺; Anal. Calc. For (HCl salt) C₃₂H₃₇F₂N₃O₂.HCl.0.20 CHCl₃: C, 65.11; H, 6.48; N, 7.07. Found: C, 65.30; H, 6.50; N, 6.96.

EXAMPLE 2

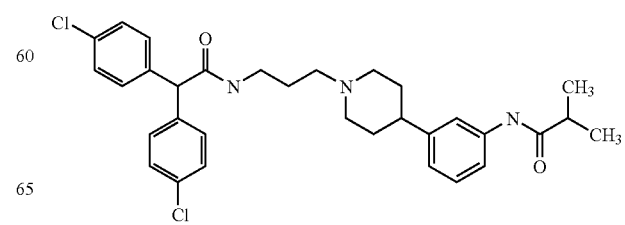

N-{3-[1-(3-{[BIS(4-CHLOROPHENYL)ACETYL]AMINO}PROPYL)-4-PIPERIDINYL]PHENYL}-2-METHYLPROPANAMIDE

Example 2 was prepared from bis(4-chlorophenyl)acetic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.64 (s, 1H), 7.34–7.13 (m, 12H), 4.75 (s, 1H), 3.41 (q, 2H, J=4.5 Hz), 2.94 (d, 2H, J=10.2 Hz), 2.51–2.40 (m, 4H), 1.97 (m, 2H), 1.82 (m, 2H), 1.68 (quintet, 2H, J=6.8 Hz), 1.59 (m, 3H), 1.25 (d, 6H, J=6.8 Hz); ESMS m/e: 566.2 (M+H)$^+$.

EXAMPLE 3

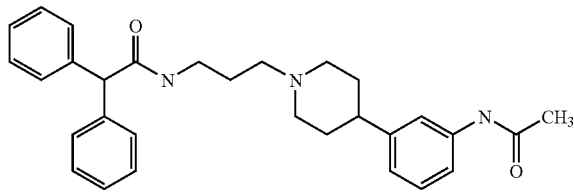

N-(3-{4-[3-(acetylamino)phenyl]-1-piperidinyl}propyl)-2,2-diphenylacetamide

Example 3 was prepared from diphenylacetyl chloride and N-{3-[1-(3-aminopropyl)-4-piperidinyl]phenyl}acetamide according to the procedures described in Scheme 8: $^1$H NMR (400 MHz, CDCl$_3$) δ 7.70 (s, 1H), 7.40 (s, 1H), 7.32–7.20 (m, 12H), 6.96 (t, 1H, J=4.8 Hz), 6.91 (d, 1H, J=7.6 Hz), 4.87 (s, 1H), 3.39 (dd, 2H, J=6.0, 12.4 Hz), 2.90 (d, 2H, J=11.6 Hz), 2.43 (m, 1H), 2.36 (t, 2H, J=6.4 Hz), 2.11 (s, 3H), 1.94 (m, 2H), 1.76 (d, 2H, J=12.4 Hz), 1.68 (t, 2H, J=6.8 Hz), 1.60 (dd, 2H, J=1.2, 8.4 Hz); ESMS m/e: 470.3 (M+H)$^+$.

EXAMPLE 4

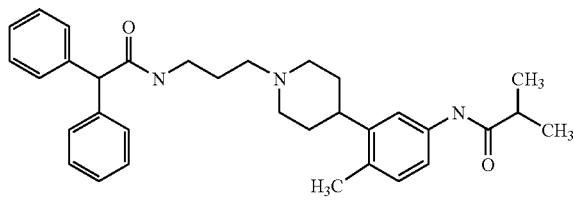

N-[3-(1-{3-[(DIPHENYLACETYL)AMINO]PROPYL}-4-PIPERIDINYL)-4-METHYLPHENYL]-2-METHYLPROPANAMIDE

Example 4 was prepared from diphenylacetyl chloride and N-{3-[1-(3-aminopropyl)-4-piperidinyl]-4-methylphenyl}-2-methylpropanamide according to the procedures described in Scheme 8: $^1$H NMR (400 MHz, CDCl$_3$) δ 7.39–7.23 (m, 12H), 7.14 (br, 1H), 7.08 (d, 1H, J=8.4 Hz), 6.90 (br, 1H), 4.91 (s, 1H), 3.41 (dd, 2H, J=6.4, 12.4 Hz), 2.95 (d, 2H, J=12.4 Hz), 2.66 (m, 1H), 2.47 (m, 1H), 2.40 (t, 2H, J=6.4 Hz), 2.28 (s, 3H), 2.03–1.97 (m, 2H), 1.74–1.62 (m, 6H), 1.22 (d, 6H, J=7.2 Hz); ESMS m/e: 512.3 (M+H)$^+$.

EXAMPLE 5

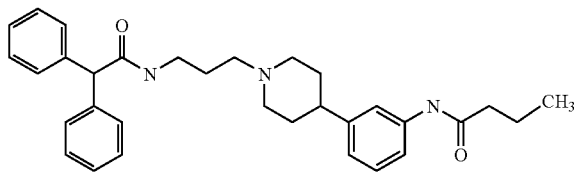

N-[3-(1-{3-[(2,2-DIPHENYLACETYL)AMINO]PROPYL}-4-PIPERIDINYL)PHENYL]BUTANAMIDE

Example 5 was prepared from diphenylacetyl chloride and N-{3-[1-(3-aminopropyl)-4-piperidinyl]phenyl}butanamide according to the procedures described in Scheme 8: $^1$H NMR (400 MHz, CDCl$_3$) δ 7.49 (s, 1H), 7.35–7.23 (m, 12H), 7.20 (s, 1H), 6.95 (d, 2H, J=7.6 Hz), 4.90 (s, 1H), 3.41 (dd, 2H, J=5.6, 11.6 Hz), 2.94 (d, 2H, J=11.6 Hz), 2.48 (m, 1H), 2.40 (t, 2H, J=6.4 Hz), 2.34 (t, 2H, J=7.2 Hz), 1.98 (t, 2H, J=11.2 Hz), 1.82–1.60 (m, 8H), 1.02 (t, 3H, J=7.2 Hz); ESMS m/e: 498.3 (M+H)$^+$.

EXAMPLE 6

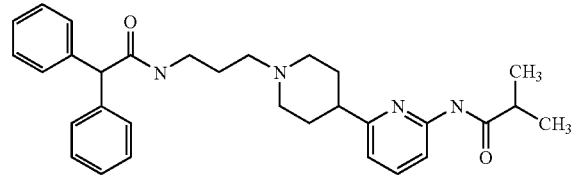

N-[6-(1-{3-[(DIPHENYLACETYL)AMINO]PROPYL}-4-PIPERIDINYL)-2-PYRIDINYL]-2-METHYLPROPANAMIDE

Example 6 was prepared from diphenylacetyl chloride and N-{6-[1-(3-aminopropyl)-4-piperidinyl]-2-pyridinyl}-2-methylpropanamide according to the procedures described in Scheme 8: $^1$H NMR (400 MHz, CDCl$_3$) δ 8.07 (d, 1H, J=8.0 Hz), 7.71–7.63 (m, 3H), 7.42–7.23 (m, 10H), 6.89 (d, 1H, J=7.6 Hz), 4.96 (s, 1H), 3.41 (dd, 2H, J=5.6, 7.6 Hz), 3.00 (d, 2H, J=11.6 Hz), 2.60 (m, 1H), 2.47 (t, 2H, J=6.4 Hz), 2.45 (m, 1H), 2.06–2.01 (m, 2H), 1.89–1.64 (m, 6H), 1.13 (d, 6H, J=6.8 Hz); ESMS m/e: 499.3 (M+H)$^+$.

EXAMPLE 7

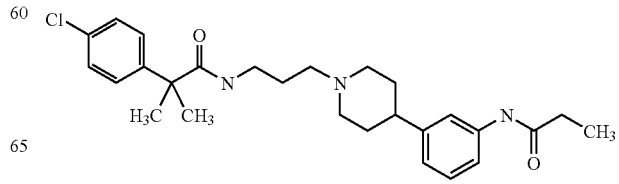

2-(4-CHLOROPHENYL)-2-METHYL-N-(3-{4-[3-(PROPIONYLAMINO)PHENYL]-1-PIPERIDINYL}PROPYL)PROPANAMIDE

Example 7 was prepared from 2-(4-chlorophenyl)-2-methylpropanoic acid and N-{3-[1-(3-aminopropyl)-4-piperidinyl]phenyl}propanamide according to the procedures described in Scheme 10: $^1$H NMR (400 MHz, CDCl$_3$) δ 7.86 (s, 1H), 7.50 (s, 1H), 7.34–7.19 (m, 6H), 6.96 (d, 1H, J=7.8 Hz), 6.72–6.67 (m, 1H), 3.42 (q, 2H, J=7.1 Hz), 3.31 (q, 3H, J=5.4 Hz), 2.49–2.35 (m, 5H), 2.08–1.95 (m, 2H), 1.82–1.74 (m, 2H), 1.71–1.62 (m, 3H), 1.56 (s, 6H), 1.24 (t, 3H, J=7.8 Hz); ESMS m/e: 470.3 (M+H)$^+$.

EXAMPLE 8

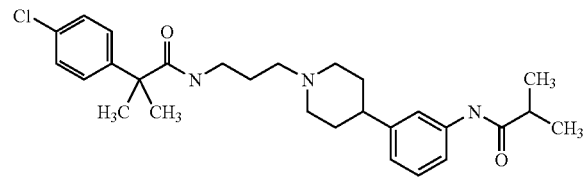

2-(4-CHLOROPHENYL)-N-(3-{4-[3-(ISOBUTYRYLAMINO)PHENYL]-1-PIPERIDINYL}PROPYL)-2-METHYLPROPANAMIDE

Example 8 was prepared from 2-(4-chlorophenyl)-2-methylpropanoic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.53 (s, 1H), 7.32–7.24 (m, 7H), 6.91 (d, 1H, J=7.2 Hz), 6.67 (m, 1H), 3.31 (q, 2H, J=5.5 Hz), 2.92–2.85 (m, 2H), 2.53 (septet, 1H, J=6.7 Hz), 2.43 (tt, 1H, J=11.6, 3.0 Hz), 2.33 (t, 2H, J=6.7 Hz), 1.91 (dt, 2H, J=11.7, 1.8 Hz), 1.78–1.72 (m, 2H), 1.65–1.59 (m, 2H), 1.56 (s, 6H), 1.52–1.45 (m, 2H), 1.25 (d, 6H, J=6.7 Hz); ESMS m/e: 484.3 (M+H)$^+$; Anal. Calc. for (HCl salt) C$_{28}$H$_{38}$ClN$_3$O$_2$·HCl·0.30 CHCl$_3$: C, 61.10; H, 7.12; N, 7.55. Found: C, 60.90; H, 7.20; N, 7.64.

EXAMPLE 9

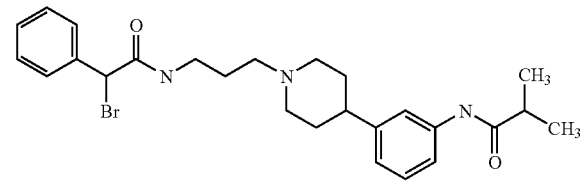

N-{3-[1-(3-{[BROMO(PHENYL)ACETYL]AMINO}PROPYL)-4-PIPERIDINYL]PHENYL}-2-METHYLPROPANAMIDE

Example 9 was prepared from bromo(phenyl)acetic acid and N-{3-[1-(3-aminopropyl)-4-piperidinyl]phenyl}-2-methylpropanamide according to the procedures described in Scheme 9: ESMS m/e: 500.0 (M+H)$^+$.

EXAMPLE 10

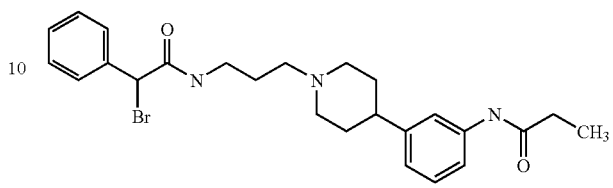

N-[3-(1-{3-[(2-BROMO-2-PHENYLACETYL)AMINO]PROPYL}-4-PIPERIDINYL)PHENYL]PROPANAMIDE

Example 10 was prepared from bromo(phenyl)acetic acid and N-{3-[1-(3-aminopropyl)-4-piperidinyl]phenyl}propanamide according to the procedures described in Scheme 10: ESMS m/e: 486.1 (M+H)$^+$.

EXAMPLE 11

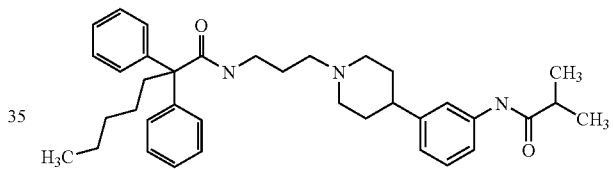

N-(3-{4-[3-(ISOBUTYRYLAMINO)PHENYL]-1-PIPERIDINYL}PROPYL)-2,2-DIPHENYLHEPTANAMIDE

Example 11 was prepared from 2,2-diphenylheptanoic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.65 (s, 1H), 7.45 (s, 1H), 7.40 (m, 1H), 7.37–7.19 (m, 11H), 6.88 (d, 1H, J=7.3 Hz), 6.34 (t, 1H, J=4.5 Hz), 3.34–3.27 (m, 3H), 2.94–2.87 (m, 2H), 2.52 (septet, 1H, J=6.9 Hz), 2.46–2.34 (m, 4H), 2.27 (t, 2H, J=6.9 Hz), 2.00–1.91 (m, 2H), 1.77–1.69 (m, 2H), 1.69–1.52, (m, 5H), 1.30–1.20 (m, 12H); ESMS m/e: 568.4 (M+H)$^+$.

EXAMPLE 12

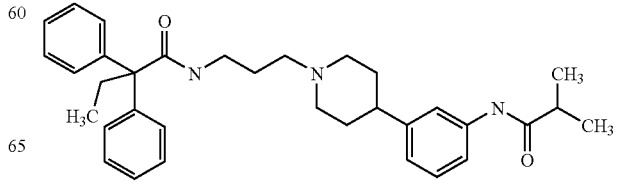

N-(3-{4-[3-(ISOBUTYRYLAMINO)PHENYL]-1-PIPERIDINYL}PROPYL)-2,2-DIPHENYLBUTANAMIDE

Example 12 was prepared from 2,2-diphenylbutanoic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.45 (s, 1H), 7.44–7.39 (m, 2H), 7.37–7.28 (m, 8H), 7.27–7.20 (m, 3H), 6.89 (d, 1H, J=7.4 Hz), 6.43 (t, 1H, J=4.5 Hz), 3.35–3.27 (m, 2H), 2.90–2.82 (m, 2H), 2.51 (septet, 1H, J=6.8 Hz), 2.49–2.35 (m, 4H), 2.24 (t, 2H, J=6.3 Hz), 1.89 (t, 2H, J=10.2 Hz), 1.75–1.68 (m, 2H), 1.66–1.58 (m, 2H), 1.57–1.45 (m, 2H), 1.24 (d, 6H, J=6.7 Hz), 1.27–1.23 (m, 2H); ESMS m/e: 526.3 (M+H)$^+$.

EXAMPLE 13

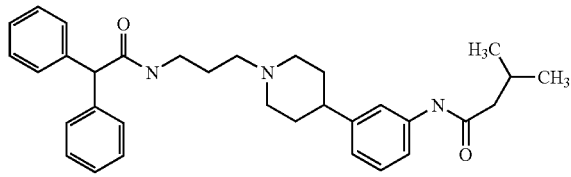

N-[3-(1-{3-[(DIPHENYLACETYL)AMINO]PROPYL}-4-PIPERIDINYL)PHENYL]-3-METHYLBUTANAMIDE

Example 13 was prepared from diphenylacetyl chloride and N-{3-[1-(3-aminopropyl)-4-piperidinyl]phenyl}-3-methylbutanamide according to the procedures described in Scheme 8: $^1$H NMR (400 MHz, CDCl$_3$) δ 10.79–10.51 (br, 1H), 8.85–8.67 (m, 1H), 8.01–7.81 (br, 1H), 7.70 (d, 1H, J=7.2 Hz), 7.47–7.14 (m, 11H), 6.89 (d, 1H, J=7.2 Hz), 5.03 (s, 1H), 3.53–3.26 (m, 4H), 2.96–2.80 (m, 2H), 2.78–2.52 (m, 3H), 2.44–2.14 (m, 2H), 2.26 (d, 2H, J=6.0 Hz), 2.14–1.94 (m, 3H), 1.94–1.76 (m, 2H), 1.10 (d, 6H, J=6.4 Hz); ESMS m/e: 512.3 (M+H)$^+$; Anal. Calc. (HCl salt) C$_{33}$H$_{42}$ClN$_3$O$_2$.0.60CH$_2$Cl$_2$: C, 67.36; H, 7.27; N, 7.01. Found: C, 67.08; H, 7.57; N, 7.36.

EXAMPLE 14

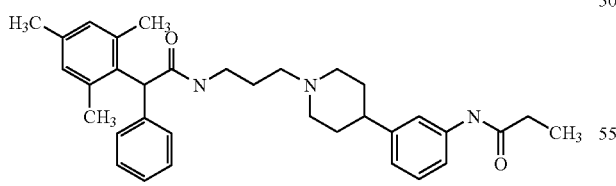

N-[3-(1-{3-[(2-MESITYL-2-PHENYLACETYL)AMINO]PROPYL}-4-PIPERIDINYL)PHENYL]PROPANAMIDE

Example 14 was prepared from mesityl(phenyl)acetic acid and N-{3-[1-(3-aminopropyl)-4-piperidinyl]phenyl}-propanamide according to the procedures described in Scheme 9: ESMS m/e: 526.3 (M+H)$^+$.

EXAMPLE 15

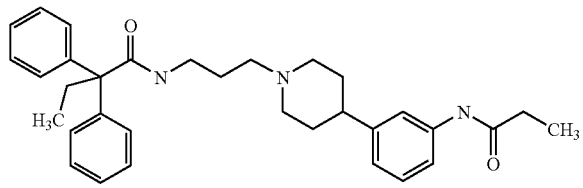

2,2-DIPHENYL-N-(3-{4-[3-(PROPIONYLAMINO)PHENYL]-1-PIPERIDINYL}PROPYL)BUTANAMIDE

Example 15 was prepared from 2,2-diphenylbutanoic acid and N-{3-[1-(3-aminopropyl)-4-piperidinyl]phenyl}propanamide according to the procedures described in Scheme 10: $^1$H NMR (400 MHz, CDCl$_3$) δ 7.43–7.38 (m, 1H), 7.37–7.29 (m, 9H), 7.28–7.21 (m, 4H), 6.90 (d, 1H, J=8.2 Hz), 6.43 (t, 1H, J=4.1), 3.32 (q, 2H, J=6.5 Hz), 2.95–2.89 (m, 2H), 2.45 (q, 2H, J=7.9 Hz), 2.43–2.35 (m, 3H), 2.27 (t, 2H, J=6.5 Hz), 2.01–1.92 (m, 2H), 1.78–1.59 (m, 6H), 1.24 (t, 3H, J=7.9 Hz), 0.79 (t, 3H, J=6.5 Hz); ESMS m/e: 512.3 (M+H)$^+$.

EXAMPLE 16

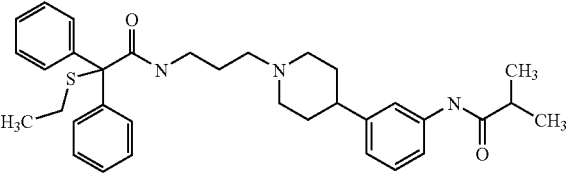

N-{3-[1-(3-{[(ETHYLSULFANYL)(DIPHENYL)ACETYL]AMINO}PROPYL)-4-PIPERIDINYL]PHENYL}-2-METHYLPROPANAMIDE

Example 16 was prepared from (ethylsulfanyl)(diphenyl)acetic acid and N-{3-[1-(3-aminopropyl)-4-piperidinyl]phenyl}-2-methylpropanamide according to the procedures described in Scheme 9: ESMS m/e: 658.6 (M+H)$^+$.

EXAMPLE 17

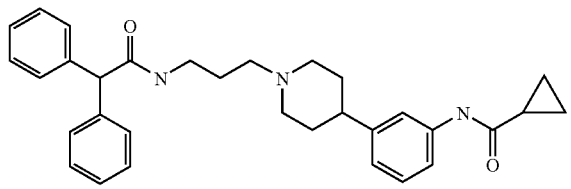

N-[3-(1-{3-[(2,2-DIPHENYLACETYL)AMINO]PROPYL}-4-PIPERIDINYL)PHENYL]CYCLOPROPANECARBOXAMIDE

Example 17 was prepared from diphenylacetyl chloride and N-{3-[1-(3-aminopropyl)-4-piperidinyl]phenyl}cyclopropanecarboxamide according to the procedures described in Scheme 8: $^1$H NMR (400 MHz, CDCl$_3$) δ 9.26–9.09 (br, 1H), 8.12–7.91 (br, 1H), 7.69 (d, 1H, J=7.2 Hz), 7.63–7.42 (br, 1H), 7.43–7.12 (m, 11H), 6.88 (d, 1H, J=7.2 Hz), 5.03 (s, 1H), 3.53–3.27 (m, 4H), 2.99–2.84 (m, 2H), 2.84–2.58 (m, 3H), 2.40–2.16 (m, 2H), 2.16–1.98 (m, 2H), 1.98–1.83 (m, 2H), 1.78–1.64 (m, 1H), 1.10–0.97 (m, 2H), 0.90–0.76 (m, 2H); ESMS m/e: 496.3 (M+H)$^+$.

EXAMPLE 18

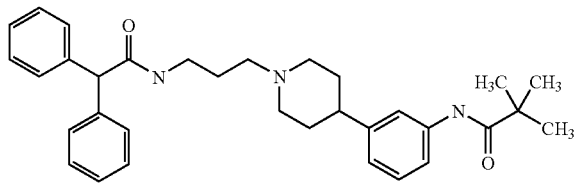

N-[3-(1-{3-[(DIPHENYLACETYL)AMINO]PROPYL}-4-PIPERIDINYL)PHENYL]-2,2-DIMETHYLPROPANAMIDE

Example 18 was prepared from diphenylacetyl chloride and N-{3-[1-(3-aminopropyl)-4-piperidinyl]phenyl}-2,2-dimethylpropanamide according to the procedures described in Scheme 8: $^1$H NMR (400 MHz, CDCl$_3$) δ 7.51–7.41 (s, 1H), 7.34–7.10 (m, 13H), 6.99–6.80 (m, 2H), 4.81 (s, 1H), 3.40–3.26 (m, 2H), 2.96–2.78 (m, 2H), 2.50–2.25 (m, 3H), 1.98–1.82 (m, 2H), 1.79–1.68 (m, 2H), 1.68–1.45 (m, 4H), 1.23 (s, 9H); ESMS m/e: 512.3 (M+H)$^+$.

EXAMPLE 19

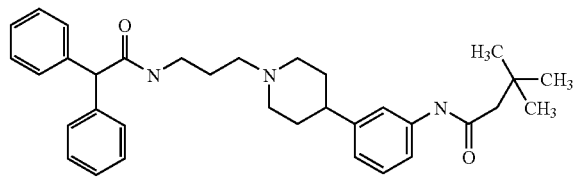

N-[3-(1-{3-[(DIPHENYLACETYL)AMINO]PROPYL}-4-PIPERIDINYL)PHENYL]-3,3-DIMETHYLBUTANAMIDE

Example 19 was prepared from diphenylacetyl chloride and N-{3-[1-(3-aminopropyl)-4-piperidinyl]phenyl}-3,3-dimethylbutanamide according procedures described in Scheme 8: $^1$H NMR (400 MHz, CDCl$_3$) δ 10.73–10.50 (br, 1H), 8.63–8.48 (m, 1H), 7.97–7.77 (br, 1H), 7.70 (d, 1H, J=7.2 Hz), 7.45–7.11 (m, 11H), 6.89 (d, 1H, J=7.2 Hz), 5.01 (s, 1H), 3.46–3.26 (m, 4H), 2.97–2.77 (m, 2H), 2.77–2.50 (m, 3H), 2.42–2.17 (m, 2H), 2.25 (s, 2H), 2.14–1.94 (m, 2H), 1.93–1.78 (m, 2H), 1.00 (s, 9H); ESMS m/e: 526.4 (M+H)$^+$; Anal. Calc. (HCl salt) C$_{34}$H$_{44}$ClN$_3$O$_2$.0.31CHCl$_3$: C, 68.77; H, 7.45; N, 7.01. Found: C, 68.51; H, 7.40; N, 7.39.

EXAMPLE 20

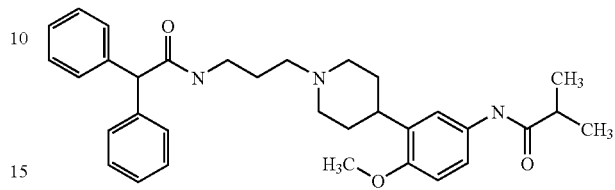

N-[3-(1-{3-[(DIPHENYLACETYL)AMINO]PROPYL}-4-PIPERIDINYL)-4-METHOXYPHENYL]-2-METHYLPROPANAMIDE

Example 20 was prepared from diphenylacetyl chloride and N-{3-[1-(3-aminopropyl)-4-piperidinyl]-4-methoxyphenyl}-2-methylpropanamide according to the procedures described in Scheme 8: ESMS m/e: 528.3 (M+H)$^+$.

EXAMPLE 21

98597

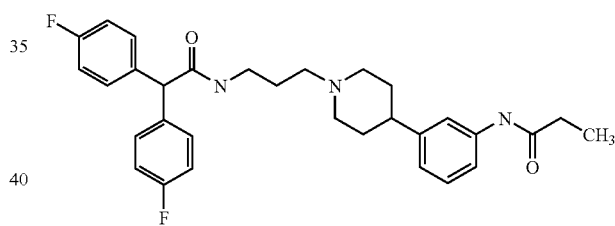

N-{3-[1-(3-{[2,2-BIS(4-FLUOROPHENYL)ACETYL]AMINO}PROPYL)-4-PIPERIDINYL]PHENYL}PROPYLANAMIDE

Example 21 was prepared from bis(4-fluorophenyl)acetic acid and N-{3-[1-(3-aminopropyl)-4-piperidinyl]phenyl}propanamide according to the procedures described in Scheme 10: ESMS m/e: 520.3 (M+H)$^+$.

EXAMPLE 22

98600

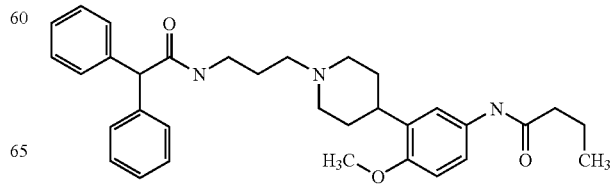

N-[3-(1-{3-[(DIPHENYLACETYL)AMINO]PROPYL}-4-PIPERIDINYL)-4-METHOXYPHENYL]BUTANAMIDE

Example 22 was prepared from diphenylacetyl chloride and N-{3-[1-(3-aminopropyl)-4-piperidinyl]-4-methoxyphenyl}butanamide according to the procedures described in Scheme 8: ESMS m/e: 528.4 (M+H)+.

EXAMPLE 23

98607

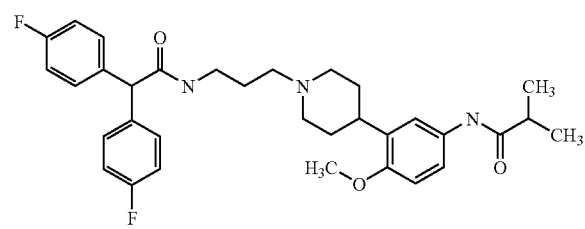

N-{3-[1-(3-{[BIS(4-FLUOROPHENYL)ACETYL]AMINO}PROPYL)-4-PIPERIDINYL]-4-METHOXYPHENYL}-2-METHYLPROPANAMIDE

Example 23 was prepared from bis(4-fluorophenyl)acetic acid and N-{3-[1-(3-aminopropyl)-4-piperidinyl]-4-methoxyphenyl}-2-methylpropanamide according to the procedures described in Scheme 9: ESMS m/e: 564.4 (M+H)+.

EXAMPLE 24

98616

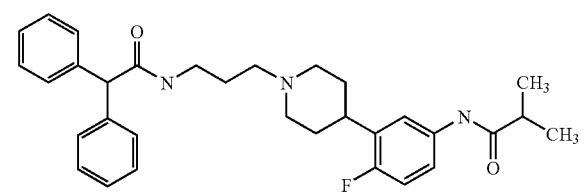

N-[3-(1-{3-[(DIPHENYLACETYL)AMINO]PROPYL}-4-PIPERIDINYL)-4-FLUOROPHENYL]-2-METHYLPROPANAMIDE

Example 24 was prepared from diphenylacetyl chloride and N-{3-[1-(3-aminopropyl)-4-piperidinyl]-4-fluorophenyl}-2-methylpropanamide according to the procedures described in Scheme 8: $^1$H NMR (400 MHz, CDCl$_3$) δ 7.95 (s, 1H), 7.47 (dd, 1H, J=2.4, 6.4 Hz), 7.34–7.21 (m, 11H), 7.06 (t, 1H, J=4.8 Hz), 6.91 (t, 1H, J=10.0 Hz), 4.90 (s, 1H), 3.38 (dd, 2H, J=6.0, 11.6 Hz), 2.90–2.87 (m, 2H), 2.74 (m, 1H), 2.50 (m, 1H), 2.36 (t, 2H, J=6.8 Hz), 1.96 (dt, 2H, J=2.8, 12.0 Hz), 1.73–1.62 (m, 6H), 1.20 (d, 6H, J=6.8 Hz); ESMS m/e: 516.3 (M+H)+.

EXAMPLE 25

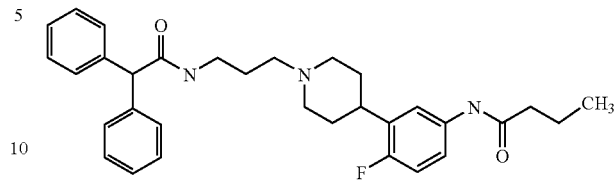

N-[3-(1-{3-[(DIPHENYLACETYL)AMINO]PROPYL}-4-PIPERIDINYL)-4-FLUOROPHENYL]BUTANAMIDE

Example 25 was prepared from diphenylacetyl chloride and N-{3-[1-(3-aminopropyl)-4-piperidinyl]-4-fluorophenyl}butanamide according to the procedures described in Scheme 8: $^1$H NMR (400 MHz, CDCl$_3$) δ 7.71 (s, 1H), 7.39 (dd, 1H, J=2.8, 6.8 Hz), 7.33–7.21 (m, 11H), 7.00 (t, 1H, J=5.6 Hz), 6.92 (t, 1H, J=9.2 Hz), 4.89 (s, 1H), 3.38 (dd, 2H, J=6.4, 12.0 Hz), 2.91–2.88 (m, 2H), 2.74 (m, 1H), 2.36 (t, 2H, J=6.4 Hz), 2.29 (t, 2H, J=7.6 Hz), 1.97 (dt, 2H, J=2.4, 11.6 Hz), 1.77–1.62 (m, 8H), 0.97 (t, 3H, J=7.2 Hz); ESMS m/e: 516.3 (M+H)+.

EXAMPLE 26

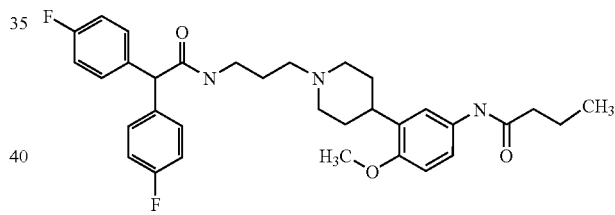

N-{3-[1-(3-{[BIS(4-FLUOROPHENYL)ACETYL]AMINO}PROPYL)-4-PIPERIDINYL]-4-METHOXYPHENYL}BUTANAMIDE

Example 26 was prepared from bis(4-fluorophenyl)acetic acid and N-{3-[1-(3-aminopropyl)-4-piperidinyl]-4-methoxyphenyl}butanamide according to the procedures described in Scheme 9: ESMS m/e: 564.4 (M+H)+.

EXAMPLE 27

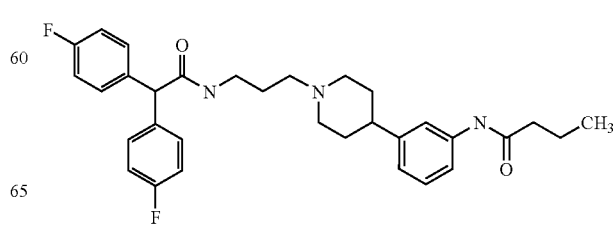

N-{3-[1-(3-{[2,2-BIS(4-FLUOROPHENYL) ACETYL]AMINO}PROPYL)-4-PIPERIDINYL] PHENYL}BUTANAMIDE

Example 27 was prepared from bis(4-fluorophenyl)acetic acid and N-{3-[1-(3-aminopropyl)-4-piperidinyl] phenyl}butanamide according to the procedures described in Scheme 10: $^1$H NMR (400 MHz, CDCl$_3$) δ 8.14 (s, 1H), 7.69 (t, 1H, J=5.2 Hz), 7.52 (s, 1H), 7.38 (d, 1H, J=8.0 Hz), 7.30–7.27 (m, 4H), 7.20 (t, 1H, J=8.0 Hz), 7.00–6.95 (m, 4H), 6.89 (d, 1H, J=8.0 Hz), 4.90 (s, 1H), 3.37 (dd, 2H, J=6.0, 11.6 Hz), 3.05 (d, 2H, J=11.2 Hz), 2.55 (t, 2H, J=6.8 Hz), 2.49 (m, 1H), 2.33 (t, 2H, J=7.2 Hz), 2.17 (m, 2H), 1.79–1.69 (m, 8H), 0.97 (t, 3H, J=7.6 Hz); ESMS m/e: 534.4 (M+H)$^+$.

EXAMPLE 28

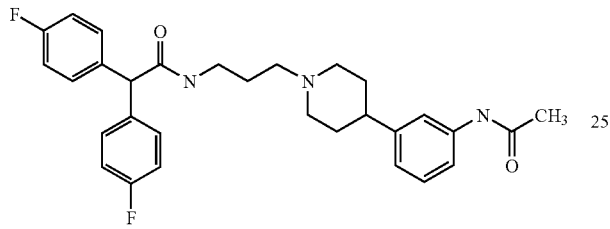

N-(3-{4-[3-(acetylamino)phenyl]-1-piperidinyl}propyl)-2,2-bis(4-fluorophenyl)acetamide Example 28 was prepared from bis(4-fluorophenyl)acetic acid and N-{3-[1-(3-aminopropyl)-4-piperidinyl] phenyl}acetamide according to the procedures described in Scheme 10: $^1$H NMR (400 MHz, CDCl$_3$) δ 8.25 (s, 1H), 7.83 (br s, 1H), 7.41–7.85 (m, 12H), 4.90 (s, 1H), 3.36 (dd, 2H, J=5.6, 12.0 Hz), 3.18 (d, 2H, J=11.6 Hz), 2.69 (t, 2H, J=6.4 Hz), 2.53 (m, 1H), 2.34 (m, 2H), 2.15 (s, 3H), 1.96–1.79 (m, 6H); ESMS m/e: 506.4 (M+H)$^+$.

EXAMPLE 29

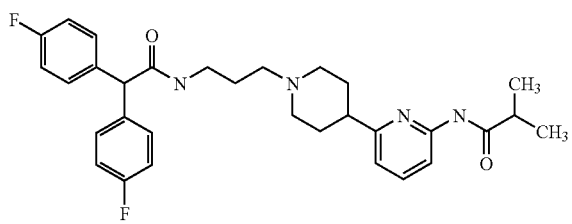

N-{6-[1-(3-{[BIS(4-FLUOROPHENYL)ACETYL] AMINO}PROPYL)-4-PIPERIDINYL]-2-PYRIDINYL}-2-METHYLPROPANAMIDE

Example 29 was prepared from bis(4-fluorophenyl)acetic acid and N-{6-[1-(3-aminopropyl)-4-piperidinyl]-2-pyridinyl}-2-methylpropanamide according to the procedures described in Scheme 10: $^1$H NMR (400 MHz, CDCl$_3$) δ 8.06 (d, 1H, J=8.4 Hz), 7.99 (m, 1H), 7.84 (s, 1H), 7.63 (t, 1H, J=8.0 Hz), 7.39–7.32 (m, 4H), 7.03–6.97 (m, 4H), 6.87 (d, 1H, J=7.6 Hz), 4.91 (s, 1H), 3.39 (dd, 2H, J=5.2, 11.2 Hz), 3.07 (d, 2H, J=11.6 Hz), 2.62 (m, 1H), 2.55 (t, 2H, J=6.4 Hz), 2.34 (m, 1H), 2.16 (t, 2H, J=11.2 Hz), 1.93–1.73 (m, 6H), 1.16 (d, 6H, J=6.8 Hz); ESMS m/e: 535.4 (M+H)$^+$.

EXAMPLE 30

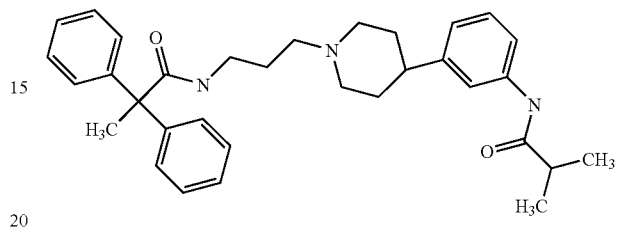

N-(3-{4-[3-(ISOBUTYRYLAMINO)PHENYL]-1-PIPERIDINYL}PROPYL)-2,2-DIPHENYLPROPANAMIDE

Example 30 was prepared from 2,2-diphenylpropanoic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.46 (s, 1H), 7.42 (s, 1H), 7.39–7.18 (m, 12H), 6.89 (d, 1H, J=7.7 Hz), 6.23 (m, 1H), 3.35 (q, 2H, J=6.4), 2.85 (d, 2H, J=10.8 Hz), 2.5 (quintet, 1H, J=7.4 Hz), 2.45–2.36 (m, 1H), 2.28 (t, 2H, J=6.4 Hz), 1.99 (s, 3H), 1.91–1.82 (m, 2H), 1.75–1.68 (m, 2H), 1.65 (t, 2H, J=6.4 Hz), 1.60–1.47 (m, 2H), 1.23 (d, 6H, J=7.0 Hz); ESMS m/e: 512.4 (M+H)$^+$.

EXAMPLE 31

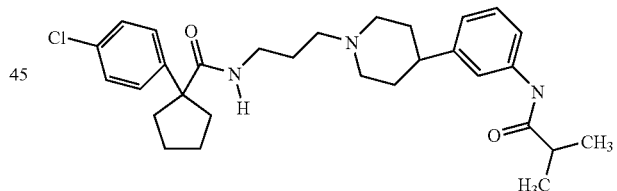

1-(4-CHLOROPHENYL)-N-(3-{4-[3-(ISOBUTYRYLAMINO)PHENYL]-1-PIPERIDINYL}PROPYL)CYCLOPENTANECARBOXAMIDE

Example 31 was prepared from 1-(4-chlorophenyl)cyclopentanecarboxylic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.45–7.42 (m, 1H), 7.33–7.24 (m, 7H), 6.94 (d, 1H, J=7.1 Hz), 6.58–6.52 (m, 1H), 3.26 (q, 2H, J=6.1 Hz), 2.90 (d, 2H, J=10.8 Hz), 2.56–2.40 (m, 4H), 2.29 (t, 2H, J=6.3 Hz), 2.03–1.87 (m, 6H), 1.83–1.76 (m, 4H), 1.60 (dd, 4H, J=6.8, 4.6 Hz), 1.25 (d, 6H, J=6.8 Hz); ESMS m/e: 510.4 (M+H)$^+$.

EXAMPLE 32

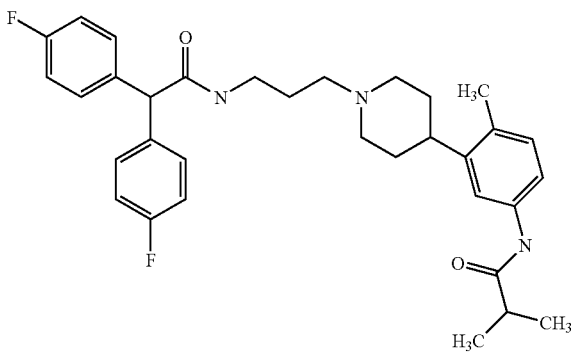

N-{3-[1-(3-{[BIS(4-FLUOROPHENYL)ACETYL]AMINO}PROPYL)-4-PIPERIDINYL]-4-METHYLPHENYL}-2-METHYLPROPANAMIDE

Example 32 was prepared from bis(4-fluorophenyl)acetic acid and N-{3-[1-(3-aminopropyl)-4-piperidinyl]-4-methylphenyl}-2-methylpropanamide according to the procedures described in Scheme 9: $^1$H NMR (400 MHz, CDCl$_3$) δ 8.09 (s, 1H), 7.98 (s, 1H), 7.59 (d, 1H, J=1.8 Hz), 7.54–7.51 (m, 1H), 7.32 (m, 3H), 7.21–7.18 (m, 1H), 6.99–6.94 (m, 5H), 4.87 (s, 1H), 3.36 (q, 2H, J=5.8 Hz), 2.92–2.97 (m, 2H), 2.68–2.58 (m, 1H), 2.5 (quintet, 1H, J=7.2 Hz), 2.37 (t, 2H, J=5.7 Hz), 2.25 (s, 3H), 2.01–1.92 (m, 2H), 1.71–1.52 (m, 6H), 1.16 (d, 6H, J=7.2 Hz); ESMS m/e: 548.4 (M+H)$^+$.

EXAMPLE 33

![structure]

N-[3-(1-{3-[(DIPHENYLACETYL)AMINO]PROPYL}-4-PIPERIDINYL)-2-METHYLPHENYL]-2-METHYLPROPANAMIDE

Example 33 was prepared from diphenylacetyl chloride and N-{3-[1-(3-aminopropyl)-4-piperidinyl]-2-methylphenyl}-2-methylpropanamide according to the procedures described in Scheme 8: $^1$H NMR (400 MHz, CDCl$_3$) δ 7.49 (d, 1H, J=8.0 Hz), 7.35–7.19 (m, 11H), 7.09–7.02 (m, 3H), 4.90 (s, 1H), 3.41 (dd, 2H, J=5.6, 11.6 Hz), 2.99 (d, 2H, J=12.8 Hz), 2.72 (m, 1H), 2.59 (m, 1H), 2.43 (t, 2H, J=6.4 Hz), 2.19 (s, 3H), 2.06–2.00 (m, 2H), 1.75–1.60 (m, 6H), 1.30 (d, 6H, J=6.8 Hz); ESMS m/e: 512.5 (M+H)$^+$.

EXAMPLE 34

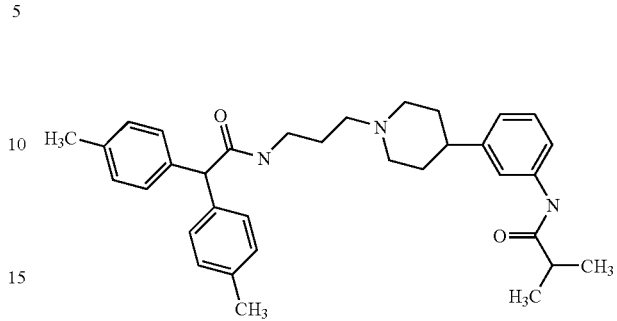

N-{3-[1-(3-{[BIS(4-METHYLPHENYL)ACETYL]AMINO}PROPYL)-4-PIPERIDINYL]PHENYL}-2-METHYLPROPANAMIDE

Example 34 was prepared from bis(4-methylphenyl)acetic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.50 (s, 1H), 7.29 (d, 2H, J=6.1 Hz), 7.13 (m, 8H), 6.93 (d, 1H, J=7.5 Hz), 6.83–6.78 (m, 1H), 7.27–7.21 (m, 1H), 4.81 (s, 1H), 3.40–3.34 (m, 2H), 2.91 (d, 2H, J=11.6 Hz), 2.53–2.41 (m, 2H), 2.36 (t, 2H, J=6.6 Hz), 2.29 (s, 6H), 1.99–1.88 (m, 2H), 1.78 (d, 3H, J=12.9 Hz), 1.67 (t, 2H, J=6.6 Hz), 1.62–1.56 (m, 1H), 1.24 (d, 6H, J=6.8 Hz); ESMS m/e: 526.4 (M+H)$^+$.

EXAMPLE 35

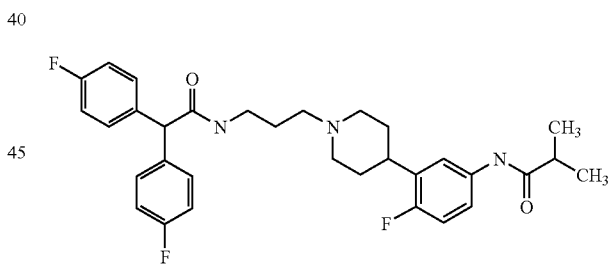

N-{3-[1-(3-{[bis(4-fluorophenyl)acetyl]amino}propyl)-4-piperidinyl]-4-fluorophenyl}-2-methylpropanamide Example 35 was prepared from bis(4-fluorophenyl)acetic acid and N-{3-[1-(3-aminopropyl)-4-piperidinyl]-4-fluorophenyl}-2-methylpropanamide according to the procedures described in Scheme 10: $^1$H NMR (400 MHz, CDCl$_3$) δ 7.58 (dd, 1H, J=2.8, 6.4 Hz), 7.53 (s, 1H), 7.49 (br s, 1H), 7.31–6.92 (m, 10H), 4.81 (s, 1H), 3.40 (dd, 2H, J=5.6, 11.2 Hz), 2.93 (d, 2H, J=11.6 Hz), 2.76 (m, 1H), 2.49 (m, 1H), 2.42 (t, 2H, J=6.0 Hz), 2.02–1.96 (m, 2H), 1.77 (d, 2H, J=11.6 Hz), 1.69–1.62 (m, 4H), 1.22 (d, 6H, J=6.8 Hz); ESMS m/e: 552.3 (M+H)$^+$.

EXAMPLE 36

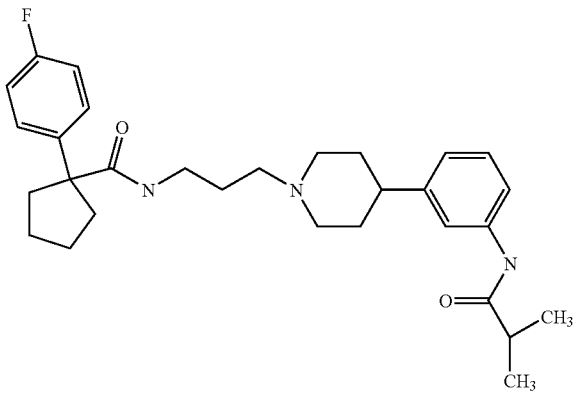

1-(4-FLUOROPHENYL)-N-(3-{4-[3-(ISOBU-TYRYLAMINO)PHENYL]-1-PIPERIDINYL}PROPYL)CYCLOPENTANECAR-BOXAMIDE

Example 36 was prepared from 1-(4-fluorophenyl)cyclopentanecarboxylic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.53 (s, 1H), 7.33 (dd, 2H, J=5.8, 3.6 Hz,), 7.29–7.26 (m, 2H), 7.25–7.20 (m, 1H), 7.02–6.95 (m, 2H), 6.93 (d, 1H, J=7.1 Hz), 6.54–6.49 (m, 1H), 3.26 (q, 2H, J=6.5 Hz), 3.22–3.14 (m, 1H), 2.90 (d, 1H, J=12.0 Hz), 2.55–2.37 (m, 4H), 2.29 (t, 2H, J=6.5 Hz), 2.06 (s, 4H), 2.00–1.90 (m, 3H), 1.82–1.75 (m, 4H), 1.73–1.66 (m, 3H), 1.65–1.57 (m, 4H), 1.25 (d, 6H, J=6.7 Hz); ESMS m/e: 494.3 (M+H)$^+$; Anal. Calc. for C$_{30}$H$_{40}$FN$_3$O$_2$.0.10 CHCl$_3$.0.650 DMF: C, 70.92; H, 8.27; N, 8.64. Found: C, 70.83; H, 8.11; N, 8.93.

EXAMPLE 37

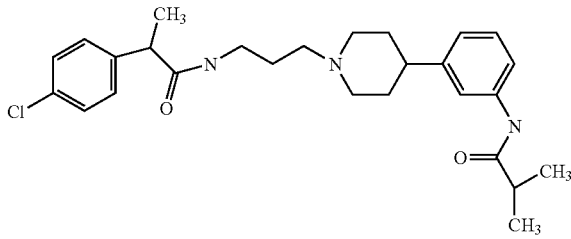

2-(4-CHLOROPHENYL)-N-(3-{4-[3-(ISOBU-TYRYLAMINO)PHENYL]-1-PIPERIDINYL}PROPYL)PROPANAMIDE

Example 37 was prepared from 2-(4-chlorophenyl)propanoic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.61 (d, 2H, J=6.5 Hz), 7.26 (s, 6H), 7.05–6.99 (m, 1H), 6.94 (d, 1H, J=7.1 Hz), 3.37–3.25 (m, 2H), 2.89 (d, 1H, J=9.6 Hz), 2.57–2.43 (m, 2H), 2.37 (t, 2H, J=6.1 Hz), 2.22–2.16 (m, 2H), 2.00–1.91 (m, 2H), 1.89–1.77 (m, 2H), 1.69–1.58 (m, 4H), 1.48 (d, 3H, J=7.0 Hz), 1.24 (d, 6H, J=7.0 Hz); ESMS m/e: 470.3 (M+H)$^+$.

EXAMPLE 38

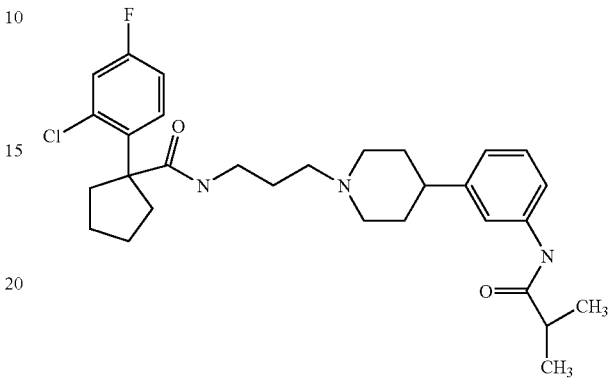

1-(2-CHLORO-4-FLUOROPHENYL)-N-(3-{4-[3-(ISOBUTYRYLAMINO)PHENYL]-1-PIPERIDINYL}PROPYL)CYCLOPENTANECAR-BOXAMIDE

Example 38 was prepared from 1-(2-chloro-4-fluorophenyl)cyclopentanecarboxylic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.58 (s, 1H), 7.52 (s, 1H), 7.45–7.36 (m, 1H), 7.34–7.29 (m, 1H), 7.23 (t, 1H, J=8.0 Hz), 7.17–7.13 (m, 1H), 6.95–6.90 (m, 2H), 6.00–5.94 (m, 1H), 3.30 (q, 2H, J=6.4 Hz), 2.92–2.84 (m, 2H), 2.57–2.38 (m, 3H), 2.47–2.39 (m, 1H), 2.31 (t, 1H, J=7.2 Hz), 1.95–1.73 (m, 7H), 1.68–1.48 (m, 8H), 1.24 (d, 6H, J=7.2 Hz); ESMS m/e: 528.3 (M+H)$^+$.

EXAMPLE 39

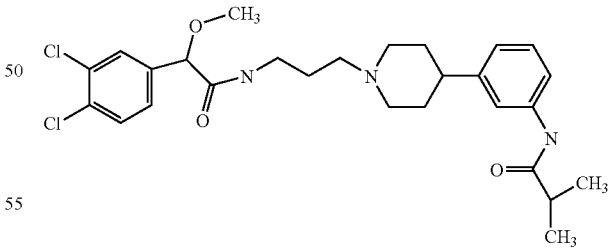

N-{3-[1-(3-{[(3,4-DICHLOROPHENYL)(METH-OXY)ACETYL]AMINO}PROPYL)-4-PIPERIDI-NYL]PHENYL}-2-METHYLPROPANAMIDE

Example 39 was prepared from (3,4-dichlorophenyl)(methoxy)acetic acid and N-{3-[1-(3-aminopropyl)-4-piperidinyl]phenyl}-2-methylpropanamide according to the procedures described in Scheme 9: $^1$H NMR (400 MHz, CDCl₃) δ 8.02–7.94 (m, 1H), 7.54 (d, 2H, J=10.1 Hz), 7.41 (d, 1H, J=8.5 Hz), 7.34–7.19 (m, 4H), 6.97 (d, 1H, J=7.0 Hz), 4.56 (s, 1H), 3.83 (s, 3H), 3.09–3.01 (m, 2H), 2.55–2.39 (m, 4H), 2.17 (s, 1H), 2.08–1.95 (m, 3H), 1.91–1.77 (m, 4H), 1.74–1.65 (m, 2H), 1.22 (d, 6H, J=6.6 Hz); ESMS m/e: 520.2 (M+H)⁺.

EXAMPLE 40

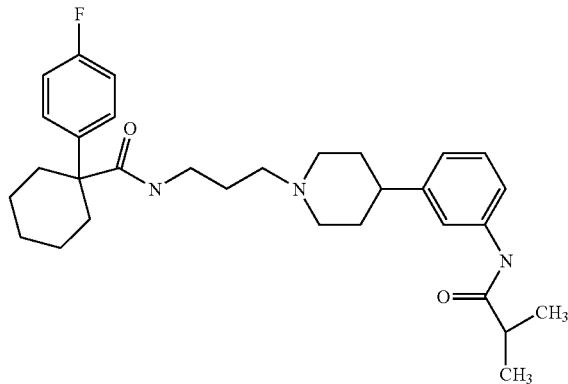

1-(4-FLUOROPHENYL)-N-(3-{4-[3-(ISOBU-TYRYLAMINO)PHENYL]-1-PIPERIDINYL}PROPYL)CYCLOHEXANECAR-BOXAMIDE

Example 40 was prepared from 1-(4-fluorophenyl)cyclohexanecarboxylic acid and N-{3-[1-(3-aminopropyl)-4-piperidinyl]phenyl}-2-methylpropanamide according to the procedures described in Scheme 9: ¹H NMR (400 MHz, CDCl₃) δ 7.56 (s, 2H), 7.42–7.36 (m, 2H), 7.30–7.20 (m, 2H), 7.05–6.96 (m, 3H), 6.85–6.79 (m, 1H), 3.28 (q, 2H, J=6.3 Hz), 2.95–2.87 (m, 2H), 2.57–2.41 (m, 2H), 2.36–2.28 (m, 4H), 2.06 (s, 1H), 1.96–1.84 (m, 4H), 1.83–1.75 (m, 2H), 1.71–1.54 (m, 9H), 1.24 (d, 6H, J=7.1 Hz); ESMS m/e: 508.3 (M+H)⁺.

EXAMPLE 41

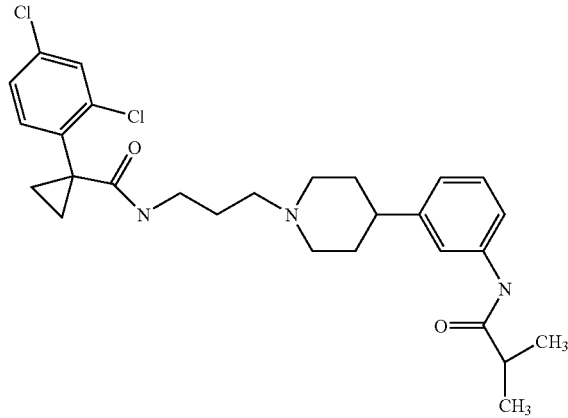

1-(2,4-DICHLOROPHENYL)-N-(3-{4-[3-(ISOBU-TYRYLAMINO)PHENYL]-1-PIPERIDINYL}PROPYL)CYCLOPROPANECAR-BOXAMIDE

Example 41 was prepared from 1-(2,4-dichlorophenyl)cyclopropanecarboxylic acid and N-{3-[1-(3-aminopropyl)-4-piperidinyl]phenyl}-2-methylpropanamide according to the procedures described in Scheme 9: ¹H NMR (400 MHz, CDCl₃) δ 7.67 (s, 1H), 7.49 (s, 1H), 7.44 (d, 1H, J=2.0 Hz), 7.35 (s, 1H), 7.28–7.19 (m, 3H), 6.92 (d, 1H, J=7.6 Hz), 5.69–5.62 (m, 1H), 3.26 (q, 2H, J=6.7 Hz), 2.89–2.82 (m, 2H), 2.54 (quintet, 1H, J=6.7 Hz), 2.47–2.37 (m, 1H), 2.32–2.26 (m, 3H), 1.97–1.88 (m, 2H), 1.79–1.69 (m, 4H), 1.66–1.56 (m, 4H), 1.24 (d, 6H, J=6.7 Hz), 1.05–1.01 (m, 1H); ESMS m/e: 516.2 (M+H)⁺; Anal. Calc. for C₂₈H₃₅Cl₂N₃O₂.0.048 CHCl₃: C, 64.51; H, 6.76; N, 8.05. Found: C, 64.51; H, 6.60; N, 8.15.

EXAMPLE 42

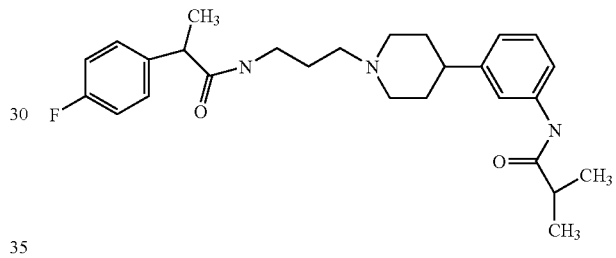

2-(4-FLUOROPHENYL)-N-(3-{4-[3-(ISOBU-TYRYLAMINO)PHENYL]-1-PIPERIDINYL}PROPYL)PROPYLANAMIDE

Example 42 was prepared from 2-(4-fluorophenyl)propanoic acid and N-{3-[1-(3-aminopropyl)-4-piperidinyl]phenyl}-2-methylpropanamide according to the procedures described in Scheme 9: ¹H NMR (400 MHz, CDCl₃) δ 7.58 (s, 2H), 7.32–7.22 (m, 4H), 7.01–6.92 (m, 3H), 6.90–6.83 (m, 1H), 3.50 (q, 1H, J=7.1 Hz), 3.39–3.26 (m, 2H), 2.93–2.86 (m, 1H), 2.55–2.42 (m, 2H), 2.40–2.34 (m, 2H), 2.16 (s, 1H), 2.01–1.91 (m, 2H), 1.89–1.77 (m, 2H), 1.72–1.54 (m, 4H), 1.49 (d, 3H, J=7.0 Hz), 1.24 (d, 6H, J=7.0 Hz); ESMS m/e: 454.3 (M+H)⁺; Anal. Calc. for C₂₇H₃₆FN₃O₂.1.1 CH₃OH: C, 69.04; H, 8.33; N, 8.60. Found: C, 69.06; H, 8.61; N, 8.79.

EXAMPLE 43

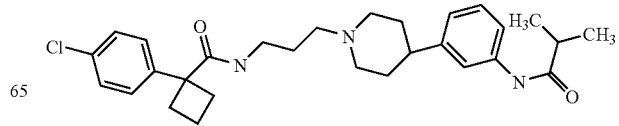

1-(4-CHLOROPHENYL)-N-(3-{4-[3-(ISOBU-TYRYLAMINO)PHENYL]-1-PIPERIDINYL}PROPYL)CYCLOBUTANECAR-BOXAMIDE

Example 43 was prepared from 1-(4-chlorophenyl)cyclobutanecarboxylic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.56 (s, 1H), 7.41 (s, 1H), 7.34–7.21 (m, 6H), 6.93 (s, 1H), 6.48 (s, 1H), 3.31–3.24 (m, 2H), 2.94–2.86 (m, 2H), 2.86–2.76 (m, 2H), 2.57–2.37 (m, 4H), 2.33–2.26 (m, 2H), 2.12–2.02 (m, 1H), 1.97–1.87 (m, 3H), 1.82 (s, 1H), 1.79 (s, 1H), 1.70–1.56 (m, 4H), 1.24 (d, 6H, J=7.2 Hz); ESMS m/e: 496.3 (M+H)$^+$; Anal. Calc. for C$_{29}$H$_{38}$ClN$_3$O$_2$.0.550 CHCl$_3$: C, 63.18; H, 6.92; N, 7.48. Found: C, 63.22; H, 6.90; N, 7.48.

EXAMPLE 44

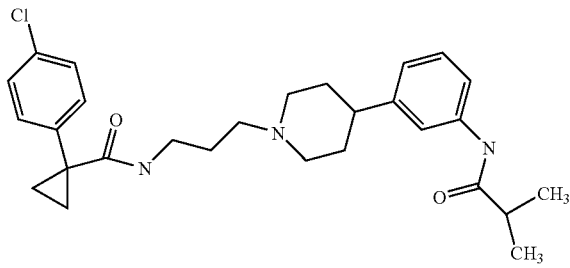

1-(4-CHLOROPHENYL)-N-(3-{4-[3-(ISOBU-TYRYLAMINO)PHENYL]-1-PIPERIDINYL}PROPYL)CYCLOPROPANECAR-BOXAMIDE

Example 44 was prepared from 1-(4-chlorophenyl)cyclopropanecarboxylic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.47 (s, 1H), 7.40 (s, 1H), 7.36–7.30 (m, 5H), 7.27–7.20 (m, 1H), 6.93 (d, 1H, J=7.6 Hz), 5.70–5.63 (m, 1H), 3.24 (q, 2H, J=6.6 Hz), 2.84 (d, 2H, J=11.4 Hz), 2.52 (quintet, 1H, J=7.2 Hz), 2.47–2.37 (m, 1H), 2.26 (t, 2H, J=7.2 Hz), 1.92 (t, 2H, J=11.6 Hz), 1.75 (d, 2H, J=12.5 Hz), 1.65–1.53 (m, 6H), 1.25 (d, 6H, J=7.2 Hz), 1.00 (q, 2H, J=2.9 Hz); ESMS m/e: 482.3 (M+H)$^+$; Anal. Calc. for C$_{28}$H$_{36}$ClN$_3$O$_2$.0.540 CH$_2$Cl$_2$: C, 64.93; H, 7.08; N, 7.96. Found: C, 65.00; H, 7.22; N, 7.81.

EXAMPLE 45

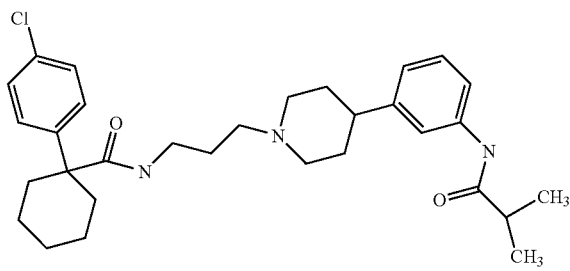

1-(4-CHLOROPHENYL)-N-(3-{4-[3-(ISOBU-TYRYLAMINO)PHENYL]-1-PIPERIDINYL}PROPYL)CYCLOHEXANECAR-BOXAMIDE

Example 45 was prepared from 1-(4-chlorophenyl)cyclohexanecarboxylic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.57 (s, 1H), 7.52 (s, 1H), 7.38–7.35 (m, 2H), 7.30–7.21 (m, 4H), 6.93 (d, 1H, J=7.2 Hz), 6.88–6.83 (m, 1H), 3.28 (q, 2H, J=5.6 Hz), 2.95–2.88 (m, 2H), 2.56–2.41 (m, 2H), 2.35–2.26 (m, 3H), 2.07 (s, 1H), 1.96–1.84 (m, 4H), 1.83–1.76 (m, 2H), 1.70–1.53 (m, 10H), 1.24 (d, 6H, J=7.1 Hz); ESMS m/e: 524.3 (M+H)$^+$.

EXAMPLE 46

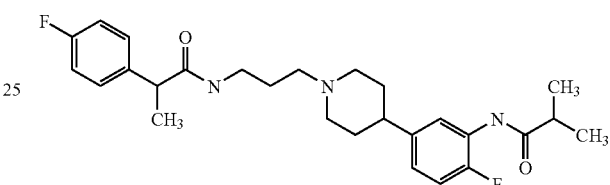

N-(3-{4-[4-FLUORO-3-(ISOBUTYRYLAMINO)PHENYL]-1-PIPERIDINYL}PROPYL)-2-(4-FLUOROPHENYL)PROPYLANAMIDE

Example 46 was prepared from 2-(4-fluorophenyl)propanoic acid and N-{5-[1-(3-aminopropyl)-4-piperidinyl]-2-fluorophenyl}-2-methylpropanamide according to the procedures described in Scheme 9: $^1$H NMR (400 MHz, CDCl$_3$) δ 8.38–8.23 (m, 1H), 7.48–7.27 (m, 3H), 7.13–6.94 (m, 4H), 6.94–6.82 (m, 1H), 3.62–3.46 (m, 1H), 3.41–3.26 (m, 2H), 3.17–3.03 (m, 1H), 3.02–2.91 (m, 1H), 2.67–2.35 (m, 4H), 2.24–1.97 (m, 2H), 1.95–1.62 (m, 6H), 1.49 (d, 3H, J=7.2 Hz), 1.27 (d, 6H, J=6.8 Hz); ESMS m/e: 472.4 (M+H)$^+$.

EXAMPLE 47

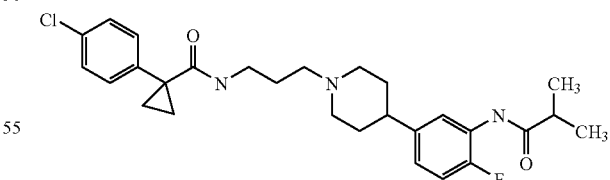

1-(4-CHLOROPHENYL)-N-(3-{4-[4-FLUORO-3-(ISOBUTYRYLAMINO)PHENYL]-1-PIPERIDINYL}PROPYL)CYCLOPROPANECAR-BOXAMIDE

Example 47 was prepared from 1-(4-chlorophenyl)cyclopropanecarboxylic acid and N-{5-[1-(3-aminopropyl)-4-piperidinyl]-2-fluorophenyl}-2-methylpropanamide according to the procedures described in Scheme 9: $^1$H NMR (400 MHz, CDCl$_3$) δ 8.32–8.18 (m, 1H), 7.43–7.25 (m, 5H), 7.08–6.93 (m, 1H), 6.93–6.79 (br, 1H), 5.74–5.59 (br, 1H), 3.35–3.15 (m, 2H), 3.93–2.75 (m, 2H), 2.65–2.49 (m, 1H), 2.49–2.34 (m, 1H), 2.34–2.19 (m, 2H), 2.00–1.83 (m, 2H), 1.82–1.68 (m, 2H), 1.68–1.48 (m, 4H), 1.36–1.17 (m, 2H), 1.27 (d, 6H, J=6.8 Hz), 1.0 (s, 2H); ESMS m/e: 500.3 (M+H)$^+$; Anal. Calc. for (HCl salt) C$_{28}$H$_{36}$Cl$_2$FN$_3$O$_2$.0.45CHCl$_3$: C, 57.85; H, 6.22; N, 7.11. Found: C, 57.61; H, 6.37; N, 7.30.

EXAMPLE 48

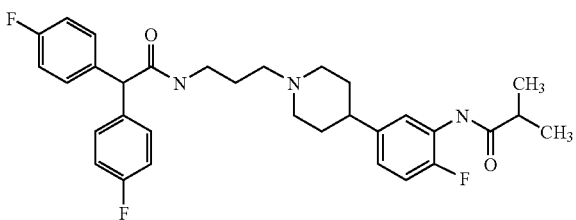

N-{5-[1-(3-{[BIS(4-FLUOROPHENYL)ACETYL] AMINO}PROPYL)-4-PIPERIDINYL]-2-FLUOROPHENYL}-2-METHYLPROPANAMIDE

Example 48 was prepared from bis(4-fluorophenyl)acetic acid and N-{5-[1-(3-aminopropyl)-4-piperidinyl]-2-fluorophenyl}-2-methylpropanamide according to the procedures described in Scheme 9: ESMS m/e: 552.3 (M+H)$^+$.

EXAMPLE 49

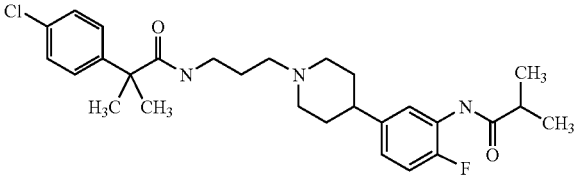

2-(4-CHLOROPHENYL)-N-(3-{4-[4-FLUORO-3-(ISOBUTYRYLAMINO)PHENYL]-1-PIPERIDINYL}PROPYL)-2-METHYLPROPANAMIDE

Example 49 was prepared from 2-(4-chlorophenyl)-2-methylpropanoic acid and N-{5-[1-(3-aminopropyl)-4-piperidinyl]-2-fluorophenyl}-2-methylpropanamide according to the procedures described in Scheme 9: $^1$H NMR (400 MHz, CDCl$_3$) δ 8.34–8.20 (m, 1H), 7.46–7.14 (m, 5H), 7.10–6.95 (m, 1H), 6.92–6.77 (br, 1H), 6.74–6.59 (br, 1H), 3.39–3.25 (m, 2H), 3.00–2.82 (m, 2H), 2.67–2.51 (m, 1H), 2.51–2.40 (m, 1H), 2.40–2.27 (m, 2H), 2.03–1.86 (m, 2H), 1.85–1.71 (m, 2H), 1.71–1.57 (m, 4H), 1.56 (s, 6H), 1.27 (d, 6H, J=6.8 Hz); ESMS m/e: 502.3 (M+H)$^+$.

EXAMPLE 50

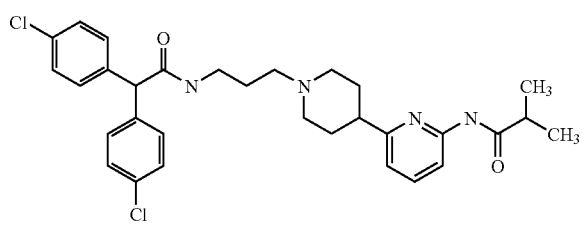

N-{6-[1-(3-{[BIS(4-CHLOROPHENYL)ACETYL] AMINO}PROPYL)-4-PIPERIDINYL]-2-PYRIDINYL}-2-METHYLPROPANAMIDE

Example 50 was prepared from bis(4-chlorophenyl)acetic acid and N-{6-[1-(3-aminopropyl)-4-piperidinyl]-2-pyridinyl}-2-methylpropanamide according to the procedures described in Scheme 10: $^1$H NMR (400 MHz, CDCl$_3$) δ 8.06 (d, 1H, J=8.0 Hz), 7.96 (br s, 1H), 7.77 (s, 1H), 7.64 (t, 1H, J=8.4 Hz), 7.31–7.26 (m, 8H), 6.88 (dd, 1H, J=0.8, 7.6 Hz), 4.84 (s, 1H), 3.39 (dd, 2H, J=5.6, 11.6 Hz), 2.99 (d, 2H, J=11.6 Hz), 2.59 (m, 1H), 2.47 (t, 2H, J=6.0 Hz), 2.28 (m, 1H), 2.07–2.00 (m, 2H), 1.89 (dd, 2H, J=2.0, 12.4 Hz), 1.76–1.67 (m, 4H), 1.14 (d, 6H, J=6.8 Hz); ESMS m/e: 567.3 (M+H)$^+$.

EXAMPLE 51

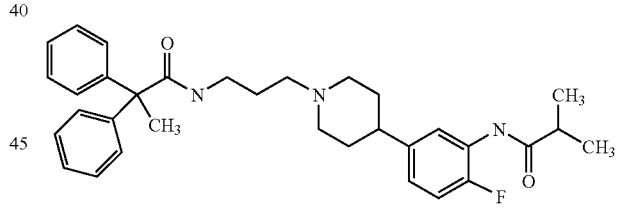

N-(3-{4-[4-FLUORO-3-(ISOBUTYRYLAMINO) PHENYL]-1-PIPERIDINYL}PROPYL)-2,2-DIPHENYLPROPANAMIDE

Example 51 was prepared from 2,2-diphenylpropanoic acid and N-{5-[1-(3-aminopropyl)-4-piperidinyl]-2-fluorophenyl}-2-methylpropanamide according to the procedures described in Scheme 9: $^1$H NMR (400 MHz, CDCl$_3$) δ 8.27–8.13 (m, 1H), 8.04 (s, 1H), 7.62 (s, 1H), 7.50–7.39 (m, 1H), 7.39–7.16 (m, 7H), 7.12–6.90 (m, 2H), 6.79–6.60 (br, 1H), 4.94–4.61 (br, 1H), 3.60–3.22 (m, 4H), 2.89–2.76 (m, 2H), 2.76–2.55 (m, 4H), 2.55–2.34 (m, 3H), 2.14–1.82 (m, 3H), 2.00 (s, 3H), 1.26 (d, 6H, J=6.4 Hz); ESMS m/e: 530.4 (M+H)$^+$; Anal. Calc. for (HCl salt) C$_{33}$H$_{41}$ClFN$_3$O$_2$.0.24CHCl$_3$.0.96H$_2$O: C, 65.23; H, 7.11; N, 6.86. Found: C, 64.96; H, 7.36; N. 6.87.

EXAMPLE 52

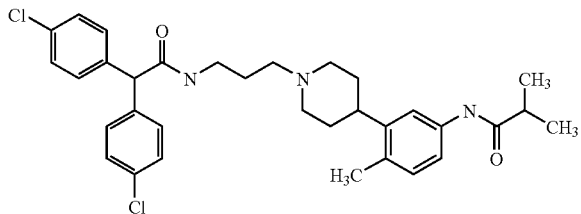

N-{3-[1-(3-{[BIS(4-CHLOROPHENYL)ACETYL] AMINO}PROPYL)-4-PIPERIDINYL]-4-METH-YLPHENYL}-2-METHYLPROPANAMIDE

Example 52 was prepared from bis(4-chlorophenyl)acetic acid and N-{3-[1-(3-aminopropyl)-4-piperidinyl]-4-methylphenyl}-2-methylpropanamide according to the procedures described in Scheme 9: $^1$H NMR (400 MHz, CDCl$_3$) δ 7.65 (s, 1H), 7.62 (d, 1H, J=2.4 Hz), 7.53 (t, 1H, J=4.8 Hz), 7.28–7.22 (m, 8H), 7.12 (dd, 1H, J=2.0, 8.4 Hz), 7.03 (d, 1H, J=8.0 Hz), 4.80 (s, 1H), 3.36 (dd, 2H, J=6.0, 11.6 Hz), 2.91 (d, 2H, J=14.0 Hz), 2.64 (m, 1H), 2.47 (m, 1H), 2.38 (t, 2H, J=5.6 Hz), 2.24 (s, 3H), 2.00–1.93 (m, 2H), 1.70–1.56 (m, 6H), 1.16 (d, 6H, J=7.2 Hz); ESMS m/e: 580.3 (M+H)$^+$.

EXAMPLE 53

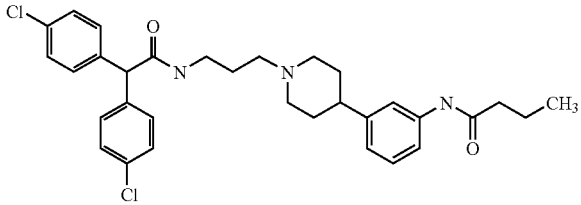

N-{3-[1-(3-{[2,2-BIS(4-CHLOROPHENYL) ACETYL]AMINO}PROPYL)-4-PIPERIDINYL] PHENYL}BUTANAMIDE

Example 53 was prepared from bis(4-chlorophenyl)acetic acid and N-{3-[1-(3-aminopropyl)-4-piperidinyl]phenyl}-butanamide according to the procedures described in Scheme 10: $^1$H NMR (400 MHz, CDCl$_3$) δ 7.67 (s, 1H), 7.58 (s, 1H), 7.49 (br s, 1H), 7.28–7.21 (m, 10H), 6.91 (m, 1H), 4.77 (s, 1H), 3.38 (dd, 2H, J=6.0, 11.6 Hz), 2.93 (d, 2H, J=11.6 Hz), 2.46 (m, 1H), 2.41 (t, 2H, J=6.0 Hz), 2.31 (t, 2H, J=7.2 Hz), 1.96 (dt, 2H, J=1.6, 12.0 Hz), 1.82–1.66 (m, 6H), 1.58–1.54 (m, 2H), 0.98 (t, 3H, J=7.6 Hz); ESMS m/e: 566.3 (M+H)$^+$.

EXAMPLE 54

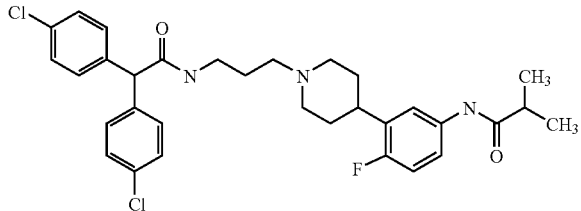

N-{3-[1-(3-{[BIS(4-CHLOROPHENYL)ACETYL] AMINO}PROPYL)-4-PIPERIDINYL]-4-FLUO-ROPHENYL}-2-METHYLPROPANAMIDE

Example 54 was prepared from bis(4-chlorophenyl)acetic acid and N-{3-[1-(3-aminopropyl)-4-piperidinyl]-4-fluorophenyl}-2-methylpropanamide according to the procedures described in Scheme 10: $^1$H NMR (400 MHz, CDCl$_3$) δ 7.62–7.57 (m, 3H), 7.27 (s, 8H), 7.23–7.19 (m, 1H), 6.94 (dd, 1H, J=8.8, 10.0 Hz), 4.78 (s, 1H), 3.39 (dd, 2H, J=6.0, 11.6 Hz), 2.93 (d, 2H, J=11.6 Hz), 2.77 (m, 1H), 2.48 (m, 1H), 2.42 (t, 2H, J=6.0 Hz), 1.99 (dt, 2H, J=1.6, 11.6 Hz), 1.77 (d, 2H, J=11.2 Hz), 1.69–1.61 (m, 4H), 1.22 (d, 6H, J=6.8 Hz); ESMS m/e: 584.2 (M+H)$^+$.

EXAMPLE 55

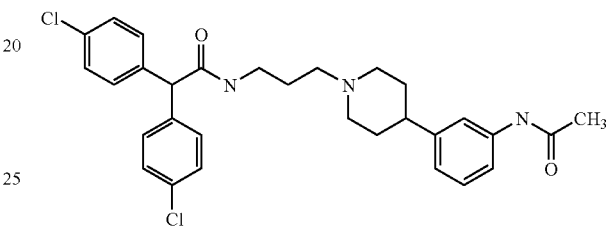

N-(3-{4-[3-(ACETYLAMINO)PHENYL]-1-PIPERIDINYL}PROPYL)-2,2-BIS(4-CHLO-ROPHENYL)ACETAMIDE

Example 55 was prepared from bis(4-chlorophenyl)acetic acid and N-{3-[1-(3-aminopropyl)-4-piperidinyl] phenyl}acetamide according procedures described in Scheme 10: $^1$H NMR (400 MHz, CDCl$_3$) δ 7.48 (s, 1H), 7.39 (br s, 1H), 7.31–7.22 (m, 11H), 6.94–6.92 (m, 1H), 4.76 (s, 1H), 3.39 (dd, 2H, J=6.4, 12.0 Hz), 2.97 (d, 2H, J=10.0 Hz), 2.49 (m, 1H), 2.44 (t, 2H, J=6.4 Hz), 2.17 (s, 3H), 2.05–1.99 (m, 2H), 1.83 (d, 2H, J=13.2 Hz), 1.71 (m, 2H), 1.61 (m, 2H); ESMS m/e: 538.3 (M+H)$^+$.

EXAMPLE 56

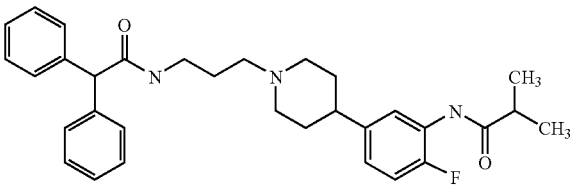

N-[5-(1-{3-[(DIPHENYLACETYL)AMINO]PRO-PYL}-4-PIPERIDINYL)-2-FLUOROPHENYL]-2-METHYLPROPANAMIDE

Example 56 was prepared from diphenylacetyl chloride and N-{5-[1-(3-aminopropyl)-4-piperidinyl]-2-fluorophenyl}-2-methylpropanamide according to the procedures described in Scheme 8: $^1$H NMR (400 MHz, CD$_3$OD,) δ 7.80–7.64 (m, 1H), 7.37–7.09 (m, 12H), 7.08–6.98 (m, 1H), 6.98–6.88 (br, 1H), 4.90 (s, 1H), 3.47–3.33 (m, 2H), 3.33–3.18 (m, 2H), 3.01–2.81 (m, 4H), 2.81–2.69 (m, 1H), 2.69–2.54 (m, 1H), 2.10–1.66 (m, 6H), 1.10 (d, 6H, J=6.4 Hz); ESMS m/e: 516.4 (M+H)$^+$. Anal. Calc. For (HCl salt)

$C_{32}H_{39}ClFN_3O_2 \cdot 0.16CHCl_3$: C, 67.68; H, 6.92; N, 7.36. Found: C, 67.43; H, 6.85; N, 7.17.

EXAMPLE 57

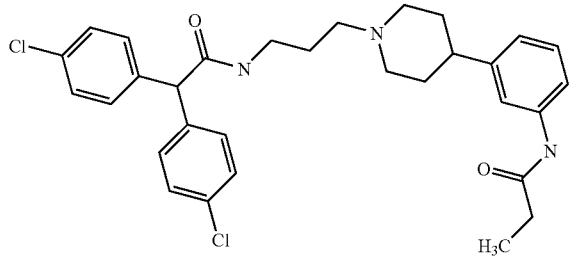

N-{3-[1-(3-{[2,2-BIS(4-CHLOROPHENYL) ACETYL]AMINO}PROPYL)-4-PIPERIDINYL] PHENYL}PROPANAMIDE

Example 57 was prepared from bis(4-chlorophenyl)acetic acid and N-{3-[1-(3-aminopropyl)-4-piperidinyl] phenyl}propanamide according to the procedures described in Scheme 10: ESMS m/e: 552.2 (M+H)$^+$.

EXAMPLE 58

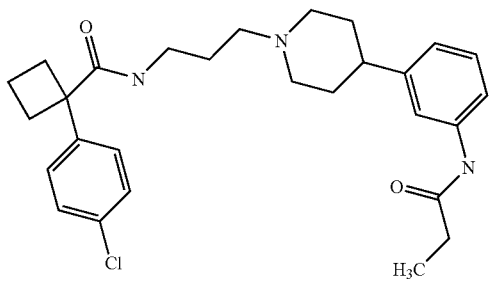

1-(4-CHLOROPHENYL)-N-(3-{4-[3-(PROPIONY-LAMINO)PHENYL]-1-PIPERIDINYL}PROPYL) CYCLOBUTANECARBOXAMIDE

Example 58 was prepared from 1-(4-chlorophenyl)cyclobutanecarboxylic acid and N-{3-[1-(3-aminopropyl)-4-piperidinyl]phenyl}propanamide according to the procedures described in Scheme 10: ESMS m/e: 482.3 (M+H)$^+$.

EXAMPLE 59

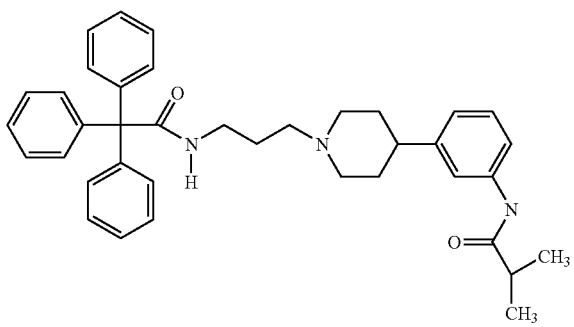

2-METHYL-N-[3-(1-{3-[(TRIPHENYLACETYL) AMINO]PROPYL}-4-PIPERIDINYL)PHENYL] PROPANAMIDE

Example 59 was prepared from triphenylacetic acid and N-{3-[1-(3-aminopropyl)-4-piperidinyl]phenyl}-2-methyl-propanamide according to the procedures described in Scheme 9: $^1$H NMR (400 MHz, CDCl$_3$) δ 7.40 (d, 2H, J=10.8 Hz), 7.32–7.17 (m, 17H), 6.87 (d, 1H, J=7.7 Hz), 6.32–6.26 (m, 1H), 3.41 (q, 2H, J=6.0 Hz), 2.83 (d, 2H, J=10.5 Hz), 2.48 (quintet, 1H, J=6.7 Hz), 2.43–2.33 (m, 1H), 2.26 (t, 2H, J=6.7 Hz), 1.89 (t, 2H, J=11.5 Hz), 1.73–1.62 (m, 4H), 1.56–1.44 (m, 2H), 1.22 (d, 6H, J=6.7 Hz); ESMS m/e: 574.3 (M+H)$^+$; Anal. Calc. for $C_{38}H_{43}N_3O_2 \cdot 0.730$ CHCl$_3$: C, 70.38; H, 6.67; N, 6.36. Found: C, 70.42; H, 6.57; N, 6.47.

EXAMPLE 60

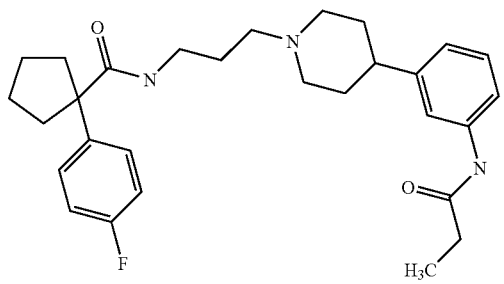

1-(4-FLUOROPHENYL)-N-(3-{4-[3-(PROPIONY-LAMINO)PHENYL]-1-PIPERIDINYL}PROPYL) CYCLOPENTANECARBOXAMIDE

Example 60 was prepared from 1-(4-fluorophenyl)cyclopentanecarboxylic acid and N-{3-[1-(3-aminopropyl)-4-piperidinyl]phenyl}propanamide according to the procedures described in Scheme 10: ESMS m/e: 480.4 (M+H)$^+$.

EXAMPLE 61

101108

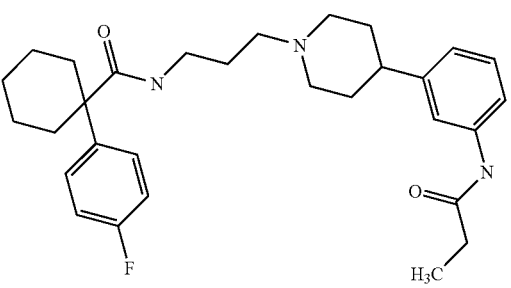

1-(4-FLUOROPHENYL)-N-(3-{4-[3-(PROPIONY-LAMINO)PHENYL]-1-PIPERIDINYL}PROPYL) CYCLOHEXANECARBOXAMIDE

Example 61 was prepared from 1-(4-fluorophenyl)cyclohexanecarboxylic acid and N-{3-[1-(3-aminopropyl)-4-piperidinyl]phenyl}propanamide according to the procedures described in Scheme 10: ESMS m/e: 494.4 (M+H)$^+$.

EXAMPLE 62

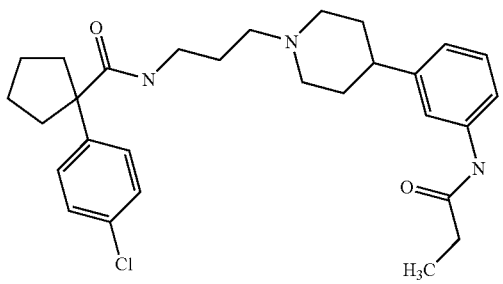

1-(4-CHLOROPHENYL)-N-(3-{4-[3-(PROPIONY-LAMINO)PHENYL]-1-PIPERIDINYL}PROPYL) CYCLOPENTANECARBOXAMIDE

Example 62 was prepared from 1-(4-chlorophenyl)cyclopentanecarboxylic acid and N-{3-[1-(3-aminopropyl)-4-piperidinyl]phenyl}propanamide according to the procedures described in Scheme 10: ESMS m/e: 496.4 (M+H)$^+$.

EXAMPLE 63

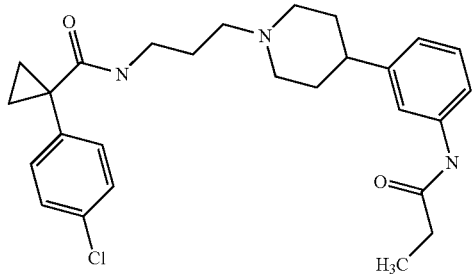

1-(4-CHLOROPHENYL)-N-(3-{4-[3-(PROPIONY-LAMINO)PHENYL]-1-PIPERIDINYL}PROPYL) CYCLOPROPANECARBOXAMIDE

Example 63 was prepared from 1-(4-chlorophenyl)cyclopropanecarboxylic acid and N-{3-[1-(3-aminopropyl)-4-piperidinyl]phenyl}propanamide according to the procedures described in Scheme 10: ESMS m/e: 468.3 (M+H)$^+$.

EXAMPLE 64

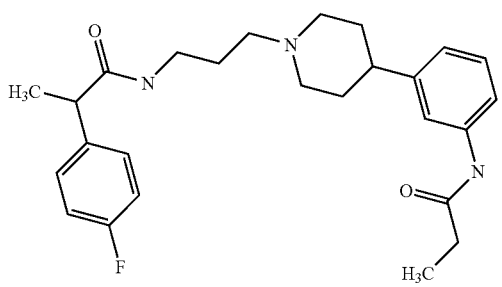

2-(4-FLUOROPHENYL)-N-(3-{4-[3-(PROPIONY-LAMINO)PHENYL]-1-PIPERIDINYL}PROPYL) PROPANAMIDE

Example 64 was prepared from 2-(4-fluorophenyl)propanoic acid and N-{3-[1-(3-aminopropyl)-4-piperidinyl]phenyl}propanamide according to the procedures described in Scheme 10: ESMS m/e: 440.4 (M+H)$^+$.

EXAMPLE 65

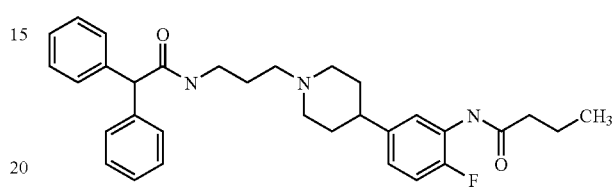

N-[5-(1-{3-[(DIPHENYLACETYL)AMINO]PROPYL}-4-PIPERIDINYL)-2-FLUOROPHENYL] BUTANAMIDE

Example 65 was prepared from diphenylacetyl chloride and N-{5-[1-(3-aminopropyl)-4-piperidinyl]-2-fluorophenyl}butanamide according to the procedures described in Scheme 8: $^1$H NMR (400 MHz, CDCl$_3$) δ 8.33–8.18 (m, 1H), 7.49–7.10 (m, 12H), 7.10–6.93 (m, 1H), 6.90–6.76 (br, 1H), 4.87 (s, 1H), 3.44–3.28 (m, 2H), 3.06–2.89 (m, 2H), 2.56–2.40 (m, 3H), 2.40–2.31 (m, 2H), 2.13–1.93 m, 2H), 1.86–1.52 (m, 8H), 1.01 (t, 3H, J=7.6 Hz) ESMS m/e: 516.6 (M+H)$^+$; Anal. Calc. For (HCl salt) C$_{32}$H$_{39}$ClFN$_3$O$_2$.0.25CHCl$_3$.1.00H$_2$O: C, 64.49; H, 6.93; N, 6.99. Found: C, 64.23; H, 7.21; N, 6.99.

EXAMPLE 66

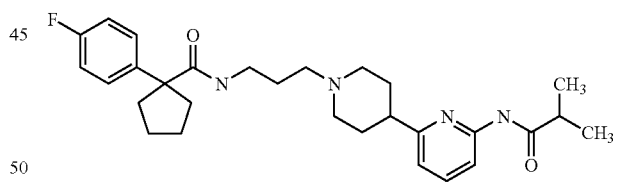

1-(4-FLUOROPHENYL)-N-(3-{4-[6-(ISOBU-TYRYLAMINO)-2-pyridinyl]-1-piperidinyl}propyl) cyclopentanecarboxamide Example 66 was prepared from 1-(4-fluorophenyl)cyclopentanecarboxylic acid and N-{6-[1-(3-aminopropyl)-4-piperidinyl]-2-pyridinyl}-2-methylpropanamide according to the procedures described in Scheme 10: $^1$H NMR (400 MHz; CDCl$_3$) δ 8.06 (d, 1H, J=8.4 Hz), 7.79 (s, 1H), 7.64 (t, 1H, J=7.6 Hz), 7.38–7.34 (m, 2H), 7.01–6.97 (m, 2H), 6.88 (d, 1H, J=7.2 Hz), 6.53 (br s, 1H), 3.27 (dd, 2H, J=6.0, 12.4 Hz), 2.94 (d, 2H, J=14.0 Hz), 2.54–2.48 (m, 4H), 2.32 (t, 2H, J=6.4 Hz), 1.99–1.60 (m, 14H), 1.25 (d, 6H, J=7.2 Hz); ESMS m/e: 495.3 (M+H)$^+$.

EXAMPLE 67

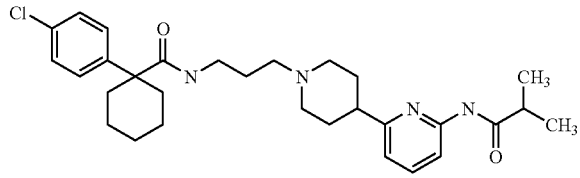

1-(4-CHLOROPHENYL)-N-(3-{4-[6-(ISOBU-TYRYLAMINO)-2-PYRIDINYL]-1-PIPERIDINYL}PROPYL)CYCLOHEXANECARBOXAMIDE

Example 67 was prepared from 1-(4-chlorophenyl)cyclohexanecarboxylic acid and N-{6-[1-(3-aminopropyl)-4-piperidinyl]-2-pyridinyl}-2-methylpropanamide according to the procedures described in Scheme 10: $^1$H NMR (400 MHz, CDCl$_3$) δ 8.06 (d, 1H, J=8.4 Hz), 7.78 (br s, 1H), 7.65 (t, 1H, J=8.0 Hz), 7.40–7.38 (m, 2H), 7.30–7.27 (m, 2H), 6.88 (d, 2H, J=7.6 Hz), 3.29 (dd, 2H, J=6.0, 11.6 Hz), 2.96 (m, 2H), 2.56–2.49 (m, 2H), 2.36–2.30 (m, 4H), 2.00–1.75 (m, 8H), 1.64–1.59 (m, 8H), 1.25 (d, 6H, J=6.8 Hz); ESMS m/e: 525.3 (M+H)$^+$.

EXAMPLE 68

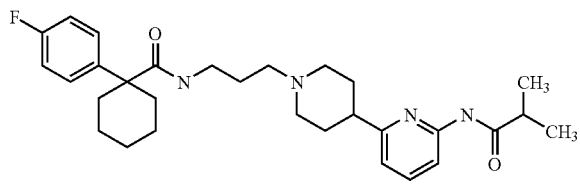

1-(4-FLUOROPHENYL)-N-(3-{4-[6-(ISOBU-TYRYLAMINO)-2-PYRIDINYL]-1-PIPERIDINYL}PROPYL)CYCLOHEXANECARBOXAMIDE

Example 68 was prepared from 1-(4-fluorophenyl)cyclohexanecarboxylic acid and N-{6-[1-(3-aminopropyl)-4-piperidinyl]-2-pyridinyl}-2-methylpropanamide according to the procedures described in Scheme 10: $^1$H NMR (400 MHz, CDCl$_3$) δ 8.07 (d, 1H, J=8.0 Hz), 7.79 (br s, 1H), 7.66 (t, 1H, J=8.0 Hz), 7.45–7.41 (m, 2H), 7.04–7.00 (m, 2H), 6.89 (d, 1H, J=7.6 Hz), 6.85 (br s, 1H), 3.30 (dd, 2H, J=6.0, 12.0 Hz), 2.97 (d, 2H, J=11.6 Hz), 2.57–2.50 (m, 2H), 2.37–2.32 (m, 4H), 2.01–1.77 (m, 8H), 1.65–1.60 (m, 8H), 1.27 (d, 6H, J=7.2 Hz); ESMS m/e: 509.3 (M+H)$^+$.

EXAMPLE 69

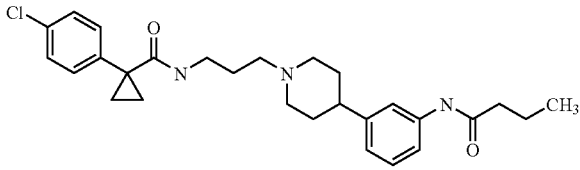

N-(3-{4-[3-(butyrylamino)phenyl]-1-piperidinyl}propyl)-1-(4-chlorophenyl)cyclopropanecarboxamide Example 69 was prepared from 1-(4-chlorophenyl)cyclopropanecarboxylic acid and N-{3-[1-(3-aminopropyl)-4-piperidinyl]phenyl}butanamide according to the procedures described in Scheme 10: $^1$H NMR (400 MHz, CDCl$_3$) δ 7.53 (s, 1H), 7.45 (s, 1H), 7.36–7.34 (m, 5H), 7.24 (t, 1H, J=8.0 Hz), 6.94 (d, 1H, J=7.6 Hz), 5.69 (br s, 1H), 3.25 (dd, 2H, J=6.8, 12.8 Hz), 2.87 (d, 2H, J=11.6 Hz), 2.44 (m, 1H), 2.35 (t, 2H, J=7.2 Hz), 2.29 (t, 2H, J=6.8 Hz), 1.95 (t, 2H, J=11.2 Hz), 1.80–1.74 (m, 4H), 1.63–1.59 (m, 6H), 1.03–1.00 (m, 5H); ESMS m/e: 482.3 (M+H)$^+$.

EXAMPLE 70

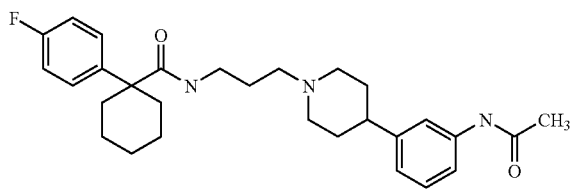

N-(3-{4-[3-(ACETYLAMINO)PHENYL]-1-PIPERIDINYL}PROPYL)-1-(4-FLUOROPHENYL)CYCLOHEXANECARBOXAMIDE

Example 70 was prepared from 1-(4-fluorophenyl)cyclohexanecarboxylic acid and N-{3-[1-(3-aminopropyl)-4-piperidinyl]phenyl}acetamide according to the procedures described in Scheme 10: $^1$H NMR (400 MHz, CDCl$_3$) δ 7.47 (m, 2H), 7.43–7.39 (m, 2H), 7.30–7.27 (m, 2H), 7.04–7.00 (m, 2H), 6.96 (d, 1H, J=7.2 Hz), 6.77 (br s, 1H), 3.30 (dd, 2H, J=5.6, 11.6 Hz), 2.95 (d, 2H, J=11.6 Hz), 2.49 (m, 1H), 2.34 (t, 4H, J=6.4 Hz), 2.19 (s, 3H), 1.99–1.80 (m, 6H), 1.73–1.60 (m, 10H); ESMS m/e: 480.3 (M+H)$^+$.

EXAMPLE 71

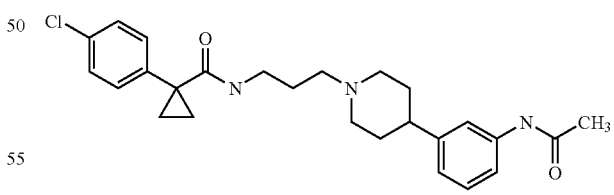

N-(3-{4-[3-(ACETYLAMINO)PHENYL]-1-PIPERIDINYL}PROPYL)-1-(4-CHLOROPHENYL)CYCLOPROPANECARBOXAMIDE

Example 71 was prepared from 1-(4-chlorophenyl)cyclopropanecarboxylic acid and N-{3-[1-(3-aminopropyl)-4-piperidinyl]phenyl}acetamide according to the procedures described in Scheme 10: $^1$H NMR (400 MHz, CDCl$_3$) δ 7.51

(s, 1H), 7.39–7.34 (m, 6H), 7.26 (t, 1H, J=7.2 Hz), 6.96 (d, 1H, J=7.6 Hz), 5.68 (br s, 1H), 3.26 (dd, 2H, J=6.8, 12.8 Hz), 2.88 (d, 2H, J=13.2 Hz), 2.45 (m, 1H), 2.30 (t, 2H, J=7.2 Hz), 2.19 (s, 3H), 1.96 (t, 2H, J=11.6 Hz), 1.78 (d, 2H, J=12.8 Hz), 1.65–1.58 (m, 6H), 1.02 (dd, 2H, J=3.6, 6.8 Hz); ESMS m/e: 454.2 (M+H)+.

EXAMPLE 72

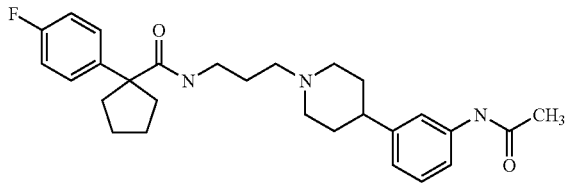

N-(3-{4-[3-(ACETYLAMINO)PHENYL]-1-PIPERIDINYL}PROPYL)-1-(4-FLUOROPHE-NYL)CYCLOPENTANECARBOXAMIDE

Example 72 was prepared from 1-(4-fluorophenyl)cyclopentanecarboxylic acid and N-{3-[1-(3-aminopropyl)-4-piperidinyl]phenyl}acetamide according to the procedures described in Scheme 10: $^1$H NMR (400 MHz, CDCl$_3$) δ 7.44 (s, 1H), 7.38–7.25 (m, 5H), 7.03–6.97 (m, 3H), 6.49 (br s, 1H), 3.29 (dd, 2H, J=5.6, 12.0 Hz), 2.98–2.94 (m, 2H), 2.55–2.49 (m, 3H), 2.33 (t, 2H, J=6.8 Hz), 2.20 (s, 3H), 2.01–1.95 (m, 4H), 1.86–1.62 (m, 10H); ESMS m/e: 466.2 (M+H)+.

EXAMPLE 73

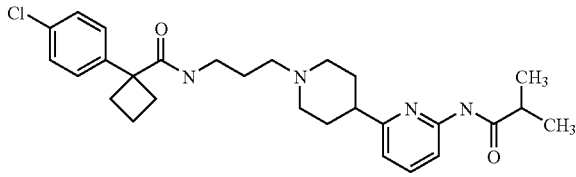

1-(4-CHLOROPHENYL)-N-(3-{4-[6-(ISOBU-TYRYLAMINO)-2-PYRIDINYL]-1-PIPERIDINYL}PROPYL)CYCLOBUTANECAR-BOXAMIDE

Example 73 was prepared from 1-(4-chlorophenyl)cyclobutanecarboxylic acid and N-{3-[1-(3-aminopropyl)-4-piperidinyl]-2-pyridinyl}-2-methylpropanamide according to the procedures described in Scheme 10: $^1$H NMR (400 MHz, CDCl$_3$) δ 8.07 (d, 1H, J=8.0 Hz), 7.78 (br s, 1H), 7.66 (t, 1H, J=7.6 Hz), 7.37–7.32 (m, 4H), 6.90 (d, 1H, J=7.6 Hz), 6.65 (br s, 1H), 3.30 (dd, 2H, J=5.6, 11.6 Hz), 2.98 (d, 2H, J=11.2 Hz), 2.88–2.81 (m, 2H), 2.58–2.43 (m, 4H), 2.36 (t, 2H, J=6.4 Hz), 2.10–1.96 (m, 4H), 1.92–1.78 (m, 4H), 1.64 (m, 2H), 1.25 (d, 6H, J=6.8 Hz); ESMS m/e: 497.2 (M+H)+.

EXAMPLE 74

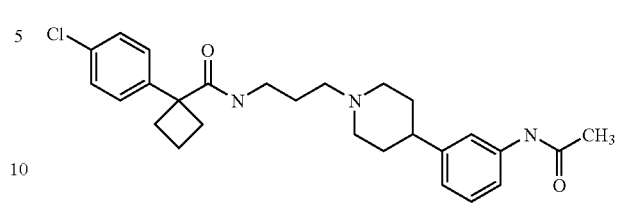

N-(3-{4-[3-(ACETYLAMINO)PHENYL]-1-PIPERIDINYL}PROPYL)-1-(4-CHLOROPHE-NYL)CYCLOBUTANECARBOXAMIDE

Example 74 was prepared from 1-(4-chlorophenyl)cyclobutanecarboxylic acid and N-{3-[1-(3-aminopropyl)-4-piperidinyl]phenyl}acetamide according to the procedures described in Scheme 10: $^1$H NMR (400 MHz, CDCl$_3$) δ 7.55 (s, 1H), 7.36–7.26 (m, 7H), 6.97 (d, 1H, J=7.2 Hz), 6.50 (br s, 1H), 3.30 (dd, 2H, J=6.0, 12.0 Hz), 2.98–2.95 (m, 2H), 2.87–2.80 (m, 2H), 2.53–2.42 (m, 3H), 2.34 (t, 2H, J=6.4 Hz), 2.20 (s, 3H), 2.15–1.82 (m, 6H), 1.74–0.161 (m, 4H); ESMS m/e: 468.2 (M+H)+.

EXAMPLE 75

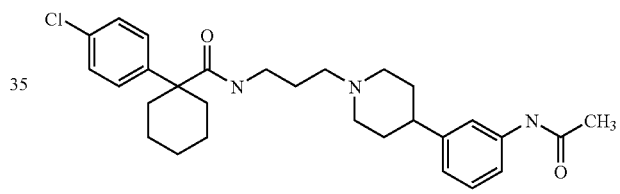

N-(3-{4-[3-(ACETYLAMINO)PHENYL]-1-PIPERIDINYL}PROPYL)-1-(4-CHLOROPHE-NYL)CYCLOHEXANECARBOXAMIDE

Example 75 was prepared from 1-(4-chlorophenyl)cyclohexanecarboxylic acid and N-{3-[1-(3-aminopropyl)-4-piperidinyl]phenyl}acetamide according to the procedures described in Scheme 10: $^1$H NMR (400 MHz, CDCl$_3$) δ 7.47 (s, 1H), 7.44 (s, 1H), 7.40–7.37 (m, 2H), 7.32–7.25 (m, 4H), 6.96 (d, 1H, J=7.2 Hz), 6.81 (br s, 1H), 3.30 (dd, 2H, J=5.6, 11.6 Hz), 2.94 (d, 2H, J=12.4 Hz), 2.49 (m, 1H), 2.34 (t, 4H, J=6.4 Hz), 2.20 (s, 3H), 1.99–1.81 (m, 6H), 1.72–1.55 (m, 10H); ESMS m/e: 496.2 (M+H)+.

EXAMPLE 76

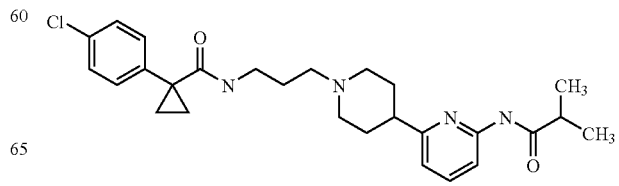

1-(4-CHLOROPHENYL)-N-(3-{4-[6-(ISOBUTYRYLAMINO)-2-PYRIDINYL]-1-PIPERIDINYL}PROPYL)CYCLOPROPANECARBOXAMIDE

Example 76 was prepared from 1-(4-chlorophenyl)cyclopropanecarboxylic acid and N-{6-[1-(3-aminopropyl)-4-piperidinyl]-2-pyridinyl}-2-methylpropanamide according to the procedures described in Scheme 10: $^1$H NMR (400 MHz, CDCl$_3$) δ 8.06 (d, 1H, J=8.0 Hz), 7.83 (s, 1H), 7.64 (t, 1H, J=7.6 Hz), 7.38–7.33 (m, 4H), 6.89 (d, 1H, J=7.6 Hz), 5.68 (br s, 1H), 3.26 (dd, 2H, J=6.0, 12.4 Hz), 2.90 (d, 2H, J=11.6 Hz), 2.58–2.52 (m, 2H), 2.31 (t, 2H, J=6.8 Hz), 1.99 (t, 2H, J=12.0 Hz), 1.85 (d, 2H, J=12.8 Hz), 1.70–1.59 (m, 6H), 1.28 (d, 6H, J=6.8 Hz), 1.01 (dd, 2H, J=3.6, 6.4 Hz); ESMS m/e: 483.3 (M+H)$^+$.

EXAMPLE 77

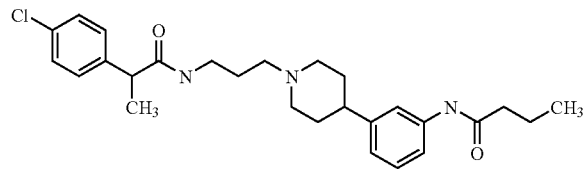

N-{3-[1-(3-{[2-(4-CHLOROPHENYL)PROPANOYL]AMINO}PROPYL)-4-PIPERIDINYL]PHENYL}BUTANAMIDE

Example 77 was prepared from 2-(4-chlorophenyl)propanoic acid and N-{3-[1-(3-aminopropyl)-4-piperidinyl]phenyl}butanamide according to the procedures described in Scheme 10: $^1$H NMR (400 MHz, CDCl$_3$) δ 7.56 (s, 1H), 7.41 (s, 1H), 7.30–7.27 (m, 6H), 6.96 (m, 2H), 3.51 (q, 1H, J=7.2 Hz), 3.50–3.30 (m, 2H), 3.02 (d, 1H, J=10.8 Hz), 2.92 (d, 1H, J=13.6 Hz), 2.50 (m, 1H), 2.41–2.34 (m, 4H), 1.99–1.94 (m, 2H), 1.86–1.58 (m, 8H), 1.51 (d, 3H, J=7.2 Hz), 1.02 (t, 3H, J=7.6 Hz); ESMS m/e: 470.3 (M+H)$^+$.

EXAMPLE 78

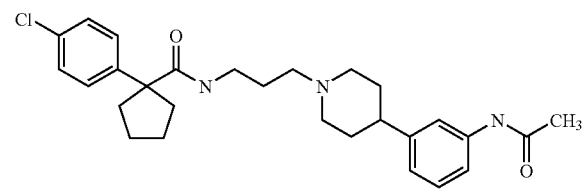

N-(3-{4-[3-(ACETYLAMINO)PHENYL]-1-PIPERIDINYL}PROPYL)-1-(4-CHLOROPHENYL)CYCLOPENTANECARBOXAMIDE

Example 78 was prepared from 1-(4-chlorophenyl)cyclopentanecarboxylic acid and N-{3-[1-(3-aminopropyl)-4-piperidinyl]phenyl}acetamide according to the procedures described in Scheme 10: $^1$H NMR (400 MHz, CDCl$_3$) δ 7.44 (s, 1H), 7.34–7.26 (m, 7H), 6.97 (d, 1H, J=7.6 Hz), 6.54 (br s, 1H), 3.28 (dd, 2H, J=5.6, 12.0 Hz), 2.95 (d, 2H, J=12.0 Hz), 2.54–2.48 (m, 3H), 2.33 (t, 2H, J=6.8 Hz), 2.20 (s, 3H), 2.00–1.95 (m, 4H), 1.84–1.60 (m, 10H); ESMS m/e: 482.2 (M+H)$^+$.

EXAMPLE 79

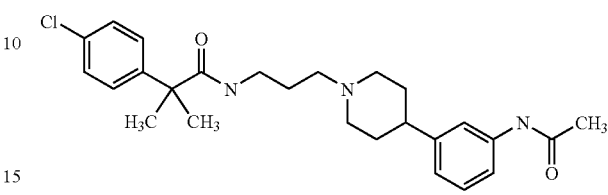

N-(3-{4-[3-(ACETYLAMINO)PHENYL]-1-PIPERIDINYL}PROPYL)-2-(4-CHLOROPHENYL)-2-METHYLPROPANAMIDE

Example 79 was prepared from 2-(4-chlorophenyl)-2-methylpropanoic acid and N-{3-[1-(3-aminopropyl)-4-piperidinyl]phenyl}acetamide according to the procedures described in Scheme 10: $^1$H NMR (400 MHz, CDCl$_3$) δ 7.43 (s, 2H), 7.34–7.25 (m, 6H), 6.95 (d, 1H, J=7.2 Hz), 6.65 (br s, 1H), 3.33 (dd, 2H, J=6.0, 12.0 Hz), 2.92 (d, 2H, J=12.0 Hz), 2.45 (m, 1H), 2.36 (t, 2H, J=6.0 Hz), 2.20 (s, 3H), 1.94 (t, 2H, J=12.4 Hz), 1.78 (d, 2H, J=13.2 Hz), 1.65 (m, 2H), 1.57 (s, 6H), 1.55–1.46 (m, 2H); ESMS m/e: 456.2 (M+H)$^+$.

EXAMPLE 80

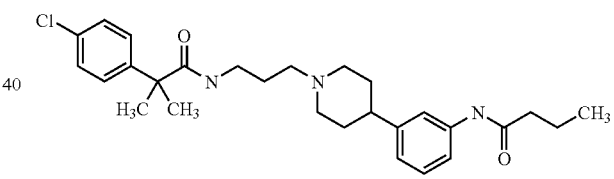

N-{3-[1-(3-{[2-(4-CHLOROPHENYL)-2-METHYLPROPANOYL]AMINO}PROPYL)-4-PIPERIDINYL]PHENYL}BUTANAMIDE

Example 80 was prepared from 2-(4-chlorophenyl)-2-methylpropanoic acid and N-{3-[1-(3-aminopropyl)-4-piperidinyl]phenyl}butanamide according to the procedures described in Scheme 9: ESMS m/e: 484.3 (M+H)$^+$.

EXAMPLE 81

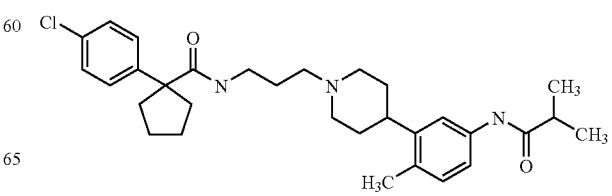

1-(4-CHLOROPHENYL)-N-(3-{4-[5-(ISOBUTYRYLAMINO)-2-METRYLPHENYL]-1-PIPERIDINYL}PROPYL)CYCLOPENTANECARBOXAMIDE

Example 81 was prepared from 1-(4-chlorophenyl)cyclopentanecarboxylic acid and N-{3-[1-(3-aminopropyl)-4-piperidinyl]-4-methylphenyl}-2-methylpropanamide according to the procedures described in Scheme 10: $^1$H NMR (400 MHz, CDCl$_3$) δ 7.44 (d, 1H, J=2.0 Hz), 7.37–7.34 (m, 2H), 7.31–7.25 (m, 4H), 7.09 (d, 1H, J=8.0 Hz), 6.50 (br s, 1H), 3.29 (dd, 2H, J=6.4, 12.0 Hz), 2.92 (d, 2H, J=11.6 Hz), 2.66 (m, 1H), 2.54–2.48 (m, 3H), 2.33–2.29 (m, 5H), 2.03–1.94 (m, 4H), 1.83–1.59 (m, 10H), 1.26 (d, 6H, J=6.8 Hz); ESMS m/e: 524.3 (M+H)$^+$.

EXAMPLE 82

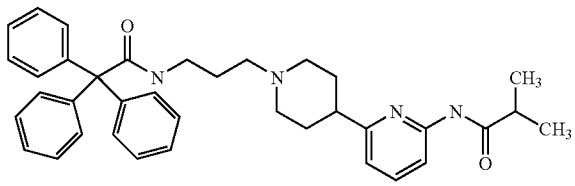

2-METHYL-N-[6-(1-{3-[(TRIPHENYLACETYL)AMINO]PROPYL}-4-PIPERIDINYL)-2-PYRIDINYL]PROPANAMIDE

Example 82 was prepared from triphenylacetic acid and N-{6-[1-(3-aminopropyl)-4-piperidinyl]-2-pyridinyl}-2-methylpropanamide according to the procedures described in Scheme 10: $^1$H NMR (400 MHz, CDCl$_3$) δ 8.05 (d, 1H, J=8.0 Hz), 7.81 (s, 1H), 7.63 (t, 1H, J=7.6 Hz), 7.30–7.24 (m, 15H), 6.84 (d, 1H, J=7.2 Hz), 6.33 (br s, 1H), 3.44 (dd, 2H, J=6.4, 12.4 Hz), 2.89 (d, 2H, J=11.6 Hz), 2.57–2.49 (m, 2H), 2.31 (t, 2H, J=6.8 Hz), 1.95 (t, 2H, J=12.0 Hz), 1.79–1.58 (m, 6H), 1.27 (d, 6H, J=6.8 Hz); ESMS m/e: 575.3 (M+H)$^+$.

EXAMPLE 83

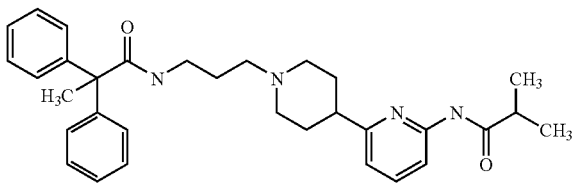

N-(3-{4-[6-(ISOBUTYRYLAMINO)-2-PYRIDINYL]-1-PIPERIDINYL}PROPYL)-2,2-DIPHENYLPROPANAMIDE

Example 83 was prepared from 2,2-diphenylpropanoic acid and N-{6-[1-(3-aminopropyl)-4-piperidinyl]-2-pyridinyl}-2-methylpropanamide according to the procedures described in Scheme 10: $^1$H NMR (400 MHz, CDCl$_3$) δ 8.05 (d, 1H, J=8.0 Hz), 7.80 (s, 1H), 7.63 (t, 1H, J=7.6 Hz), 7.35–7.24 (m, 10H), 6.85 (d, 1H, J=8.0 Hz), 6.26 (t, 1H, J=4.8 Hz), 3.38 (dd, 2H, J=6.4, 12.4 Hz), 2.92–2.89 (m, 2H), 2.55–2.48 (m, 2H), 2.32 (t, 2H, J=6.8 Hz), 2.00 (s, 3H), 1.96 (t, 2H, J=11.2 Hz), 1.79 (d, 2H, J=11.6 Hz), 1.72–1.61 (m, 4H), 1.27 (d, 6H, 6.8 Hz); ESMS m/e: 513.3 (M+H)$^+$.

EXAMPLE 84

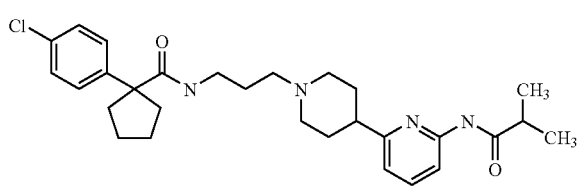

1-(4-CHLOROPHENYL)-N-(3-{4-[6-(ISOBUTYRYLAMINO)-2-PYRIDINYL]-1-PIPERIDINYL}PROPYL)CYCLOPENTANECARBOXAMIDE

Example 84 was prepared from 1-(4-chlorophenyl)cyclopentanecarboxylic acid and N-{6-[1-(3-aminopropyl)-4-piperidinyl]-2-pyridinyl}-2-methylpropanamide according to the procedures described in Scheme 10: $^1$H NMR (400 MHz, CDCl$_3$) δ 8.07 (d, 1H, J=8.4 Hz), 7.81 (s, 1H), 7.66 (t, 1H, J=7.6 Hz), 7.36–7.33 (m, 2H), 7.30–7.27 (m, 2H), 6.90 (d, 1H, J=6.8 Hz), 6.60 (br s, 1H), 3.28 (dd, 2H, J=5.6, 12.0 Hz), 2.95 (d, 2H, J=11.6 Hz), 2.55–2.49 (m, 4H), 2.33 (t, 2H, J=6.4 Hz), 2.00–1.61 (m, 14H), 1.26 (d, 6H, J=6.8 Hz); ESMS m/e: 511.3 (M+H)$^+$.

EXAMPLE 85

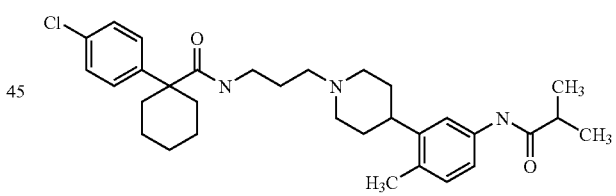

1-(4-CHLOROPHENYL)-N-(3-{4-[5-(ISOBUTYRYLAMINO)-2-METHYLPHENYL]-1-PIPERIDINYL}PROPYL)CYCLOHEXANECARBOXAMIDE

Example 85 was prepared from 1-(4-chlorophenyl)cyclohexanecarboxylic acid and N-{3-[1-(3-aminopropyl)-4-piperidinyl]-4-methylphenyl}-2-methylpropanamide according to the procedures described in Scheme 10: $^1$H NMR (400 MHz, CDCl$_3$) δ 7.46 (d, 1H, J=1.6 Hz), 7.42–7.39 (m, 2H), 7.31–7.21 (m, 4H), 7.08 (d, 1H, J=8.0 Hz), 6.78 (br s, 1H), 3.29 (dd, 2H, J=6.0, 12.0 Hz), 2.93 (d, 2H, J=11.6 Hz), 2.65 (m, 1H), 2.50 (m, 1H), 2.34–2.30 (m, 4H), 2.28 (s, 3H), 2.00–1.88 (m, 4H), 1.74–1.59 (m, 12H), 1.25 (d, 6H, J=6.8 Hz); ESMS m/e: 538.3 (M+H)$^+$.

EXAMPLE 86

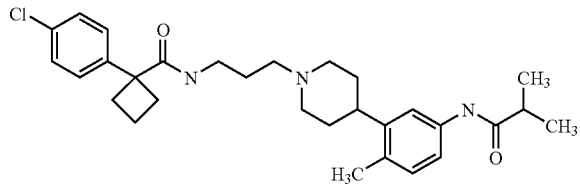

1-(4-CHLOROPHENYL)-N-(3-{4-[5-(ISOBU-TYRYLAMINO)-2-METHYLPHENYL]-1-PIPERIDINYL}PROPYL)CYCLOBUTANECAR-BOXAMIDE

Example 86 was prepared from 1-(4-chlorophenyl)cyclobutanecarboxylic acid and N-{3-[1-(3-aminopropyl)-4-piperidinyl]-4-methylphenyl}-2-methylpropanamide according to the procedures described in Scheme 10: $^1$H NMR (400 MHz, CDCl$_3$) δ 7.46 (d, 1H, J=1.6 Hz), 7.34 (s, 4H), 7.28–7.23 (m, 2H), 7.10 (d, 1H, J=8.4 Hz), 6.45 (br s, 1H), 3.31 (dd, 2H, J=5.6, 11.6 Hz), 2.95 (d, 2H, J=11.6 Hz), 2.88–2.81 (m, 2H), 2.68 (m, 1H), 2.54–2.44 (m, 3H), 2.33 (t, 2H, J=6.4 Hz), 2.29 (s, 3H), 2.11–1.90 (m, 4H), 1.76–1.63 (m, 6H), 1.26 (d, 6H, J=7.2 Hz) ESMS m/e: 510.3 (M+H)$^+$.

EXAMPLE 87

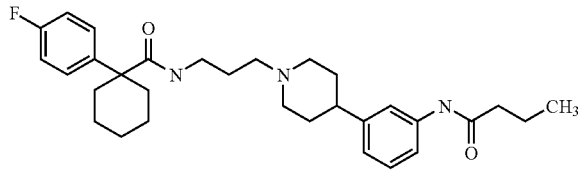

N-(3-{4-[3-(BUTYRYLAMINO)PHENYL]-1-PIPERIDINYL}PROPYL)-1-(4-FLUOROPHE-NYL)CYCLOHEXANECARBOXAMIDE

Example 87 was prepared from 1-(4-fluorophenyl)cyclohexanecarboxylic acid and N-{3-[1-(3-aminopropyl)-4-piperidinyl]phenyl}butanamide according to the procedures described in Scheme 10: $^1$H NMR (400 MHz, CDCl$_3$) δ 7.52 (s, 1H), 7.44 (s, 1H), 7.41–7.37 (m, 2H), 7.29–7.23 (m, 2H), 7.02–6.97 (m, 2H), 6.93 (d, 1H, J=6.8 Hz), 6.80 (br s, 1H), 3.29 (dd, 2H, J=5.6, 11.6 Hz), 2.92 (d, 2H, J=11.6 Hz), 2.46 (m, 1H), 2.36–2.30 (m, 6H), 1.96–1.30 (m, 18H), 1.01 (t, 3H, J=7.6 Hz), ESMS m/e: 508.3 (M+H)$^+$.

EXAMPLE 88

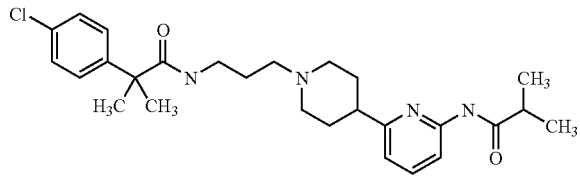

2-(4-CHLOROPHENYL)-N-(3-{4-[6-(ISOBU-TYRYLAMINO)-2-PYRIDINYL]-1-PIPERIDINYL}PROPYL)-2-METHYLPROPANA-MIDE

Example 88 was prepared from 2-(4-chlorophenyl)-2-methylpropanoic acid and N-{6-[1-(3-aminopropyl)-4-piperidinyl]-2-pyridinyl}-2-methylpropanamide according to the procedures described in Scheme 10: $^1$H NMR (400 MHz, CDCl$_3$) δ 8.08 (d, 1H, J=8.4 Hz), 7.82 (s, 1H), 7.67 (t, 1H, J=7.6 Hz), 7.33–7.27 (m, 4H), 6.88 (d$_1$H, J=7.2 Hz), 6.57 (br s, 1H), 3.33 (dd, 2H, J=6.0, 12.0 Hz), 2.94 (d, 2H, J=11.6 Hz), 2.58–2.53 (m, 2H), 2.37 (t, 2H, J=6.4 Hz), 1.97 (t, 2H, J=11.2 Hz), 1.87 (d, 2H, J=13.2 Hz), 1.67–1.58 (m, 4H), 1.57 (s, 6H), 1.28 (d, 6H, J=7.2 Hz); ESMS m/e: 485.3 (M+H)$^+$.

EXAMPLE 89

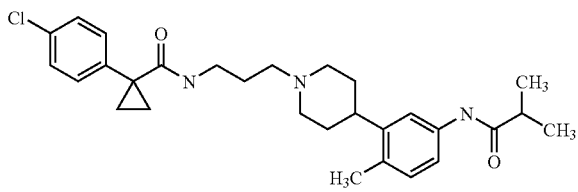

1-(4-CHLOROPHENYL)-N-(3-{4-[5-(ISOBU-TYRYLAMINO)-2-METHYLPHENYL]-1-PIPERIDINYL}PROPYL)CYCLOPROPANECAR-BOXAMIDE

Example 89 was prepared from 1-(4-chlorophenyl)cyclopropanecarboxylic acid and N-{3-[1-(3-aminopropyl)-4-piperidinyl]-4-methylphenyl}-2-methylpropanamide according to the procedures described in Scheme 10: $^1$H NMR (400 MHz, CDCl$_3$) δ 7.40–7.32 (m, 7H), 7.08 (d, 1H, J=8.4 Hz), 5.70 (br s, 1H), 3.27 (dd, 2H, J=6.4, 12.4 Hz), 2.88 (d, 2H, J=11.6 Hz), 2.64 (m, 1H), 2.53 (m, 1H), 2.31 (t, 2H, J=6.8 Hz), 2.28 (s, 3H), 1.99 (dt, 2H, J=2.8, 11.2 Hz), 1.67–1.60 (m, 8H), 1.27 (d, 6H, J=6.8 Hz), 1.03 (dd, 2H, J=4.0, 6.8 Hz); ESMS m/e: 496.3 (M+H)$^+$.

EXAMPLE 90

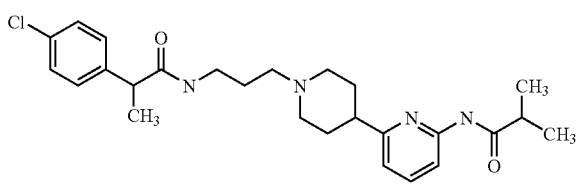

2-(4-CHLOROPHENYL)-N-(3-{4-[6-(ISOBU-TYRYLAMINO)-2-PYRIDINYL]-1-PIPERIDINYL}PROPYL)PROPYLANAMIDE

Example 90 was prepared from 2-(4-chlorophenyl)propanoic acid and N-{6-[1-(3-aminopropyl)-4-piperidinyl]-2-pyridinyl}-2-methylpropanamide according procedures described in Scheme 10: $^1$H NMR (400 MHz, CDCl$_3$) δ 8.06 (d, 1H, J=8.0 Hz), 7.75 (s, 1H), 7.64 (t, 1H, J=7.6 Hz), 7.34–7.27 (m, 4H), 7.22 (br s, 1H), 6.89 (d, 1H, J=7.6 Hz), 3.53 (q, 1H, J=7.2 Hz), 3.36 (m, 1H), 3.29 (m, 1H), 3.05 (d, 1H, J=11.6 Hz), 2.95 (d, 1H, J=10.4 Hz), 2.58 (m, 1H), 2.45–2.40 (m, 3H), 2.02–1.63 (m, 8H), 1.50 (d, 3H, J=7.2 Hz), 1.22 (dd, 6H, J=1.6, 6.8 Hz); ESMS m/e: 471.2 (M+H)$^+$.

EXAMPLE 91

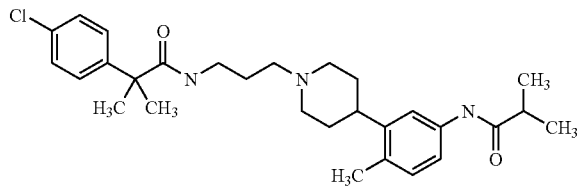

2-(4-CHLOROPHENYL)-N-(3-{4-[5-(ISOBU-TYRYLAMINO)-2-METHYLPHENYL]-1-PIPERIDINYL}PROPYL)-2-METHYLPROPANAMIDE

Example 91 was prepared from 2-(4-chlorophenyl)-2-methylpropanoic acid and N-{3-[1-(3-aminopropyl)-4-piperidinyl]-4-methylphenyl}-2-methylpropanamide according to the procedures described in Scheme 10: $^1$H NMR (400 MHz, CDCl$_3$) δ 7.41–7.27 (m, 7H), 7.09 (d, 1H, J=8.0 Hz), 6.59 (br s, 1H), 3.34 (dd, 2H, J=6.4, 12.0 Hz), 2.93 (d, 2H, J=11.6 Hz), 2.64 (m, 1H), 2.54 (m, 1H), 2.37 (t, 2H, J=6.4 Hz), 2.28 (s, 3H), 1.98 (t, 2H, J=12.4 Hz), 1.71–1.64 (m, 4H), 1.59 (s, 6H), 1.61–1.55 (m, 2H), 1.28 (d, 6H, J=6.8 Hz); ESMS m/e: 498.3 (M+H)$^+$.

EXAMPLE 92

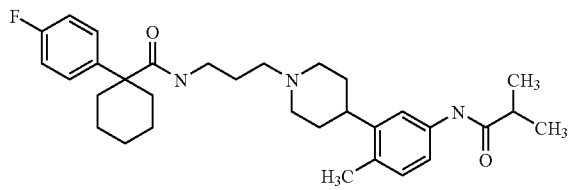

1-(4-FLUOROPHENYL)-N-(3-{4-[5-(ISOBU-TYRYLAMINO)-2-METHYLPHENYL]-1-PIPERIDINYL}PROPYL)CYCLOHEXANECAR-BOXAMIDE

Example 92 was prepared from 1-(4-fluorophenyl)cyclohexanecarboxylic acid and N-{3-[1-(3-aminopropyl)-4-piperidinyl]-4-methylphenyl}-2-methylpropanamide according to the procedures described in Scheme 10: $^1$H NMR (400 MHz, CDCl$_3$) δ 7.46–7.43 (m, 3H), 7.26–7.22 (m, 2H), 7.10 (d, 1H, J=8.4 Hz), 7.06–7.01 (m, 2H), 6.74 (br s, 1H), 3.31 (dd, 2H, J=6.0, 12.0 Hz), 2.96 (d, 2H, J=11.6 Hz), 2.68 (m, 1H), 2.52 (m, 1H), 2.36–2.32 (m, 4H), 2.29 (s, 3H), 2.03–1.90 (m, 4H), 1.74–1.61 (m, 12H), 1.27 (d, 6H, J=6.8 Hz); ESMS m/e: 522.3 (M+H)$^+$.

EXAMPLE 93

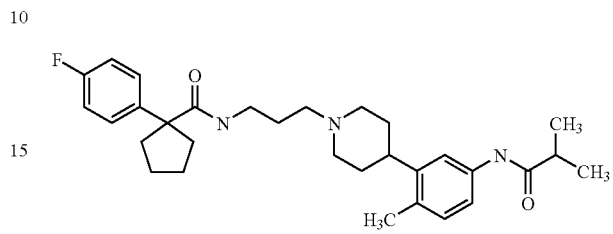

1-(4-FLUOROPHENYL)-N-(3-{4-[5-(ISOBU-TYRYLAMINO)-2-METHYLPHENYL]-1-PIPERIDINYL}PROPYL)CYCLOPENTANECAR-BOXAMIDE

Example 93 was prepared from 1-(4-fluorophenyl)cyclopentanecarboxylic acid and N-{3-[1-(3-aminopropyl)-4-piperidinyl]-4-methylphenyl}-2-methylpropanamide according to the procedures described in Scheme 10: $^1$H NMR (400 MHz, CDCl$_3$) δ 7.43–7.37 (m, 3H), 7.29–7.27 (m, 2H), 7.09 (d, 1H, J=8.4 Hz), 7.04–7.00 (m, 2H), 6.47 (br s, 1H), 3.29 (dd, 2H, J=5.6, 12.0 Hz), 2.94 (d, 2H, J=12.0 Hz), 2.66 (m, 1H), 2.54–2.48 (m, 3H), 2.33–2.30 (m, 2H), 2.29 (s, 3H), 2.03–1.95 (m, 4H), 1.84–1.60 (m, 10H), 1.26 (d, 6H, J=6.8 Hz); ESMS m/e: 508.3 (M+H)$^+$.

EXAMPLE 94

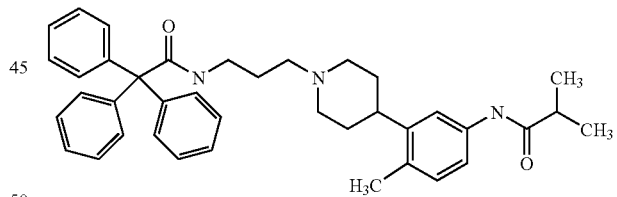

2-METHYL-N-[4-METHYL-3-(1-{3-[(TRIPHENYLACETYL)AMINO]PROPYL}-4-PIPERIDINYL)PHENYL]PROPANAMIDE

Example 94 was prepared from triphenylacetic acid and N-{3-[1-(3-aminopropyl)-4-piperidinyl]-4-methylphenyl}-2-methylpropanamide according to the procedures described in Scheme 10: $^1$H NMR (400 MHz, CDCl$_3$) δ 7.39 (dd, 1H, J=1.6, 8.0 Hz), 7.35–7.27 (m, 15H), 7.22–7.20 (m, 2H), 7.09 (d, 1H, J=8.0 Hz), 6.25 (br s, 1H), 3.45 (dd, 2H, J=6.8, 12.4 Hz), 2.90 (d, 2H, J=10.8 Hz), 2.63 (m, 1H), 2.52 (m, 1H), 2.33–2.29 (m, 2H), 2.28 (s, 3H), 1.97 (t, 2H, J=10.0 Hz), 1.72–1.57 (m, 6H), 1.27 (d, 6H, J=6.8 Hz); ESMS m/e: 588.3 (M+H)$^+$.

EXAMPLE 95

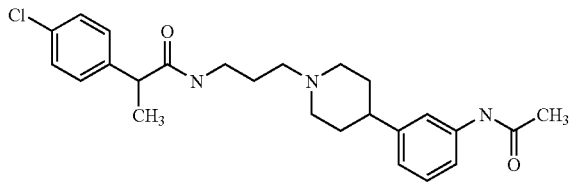

N-(3-{4-[3-(ACETYLAMINO)PHENYL]-1-PIPERIDINYL}PROPYL)-2-(4-CHLOROPHENYL)PROPYLANAMIDE

Example 95 was prepared from 2-(4-chlorophenyl)propanoic acid and N-{3-[1-(3-aminopropyl)-4-piperidinyl]phenyl}acetamide according to the procedures described in Scheme 10: $^1$H NMR (400 MHz, CDCl$_3$) δ 7.48 (s, 1H), 7.36 (s, 1H), 7.31–7.25 (m, 6H), 6.98–6.93 (m, 2H), 3.51–3.48 (m, 1H), 3.35–3.31 (m, 2H), 3.03 (d, 1H, J=11.6 Hz), 2.93 (d, 1H, J=11.2 Hz), 2.50 (m, 1H), 2.42–2.38 (m, 2H), 2.19 (s, 3H), 2.05–1.96 (m, 2H), 1.90–1.80 (m, 2H), 1.70–1.59 (m, 4H), 1.51 (d, 3H, J=7.2 Hz); ESMS m/e: 442.2 (M+H)$^+$.

EXAMPLE 96

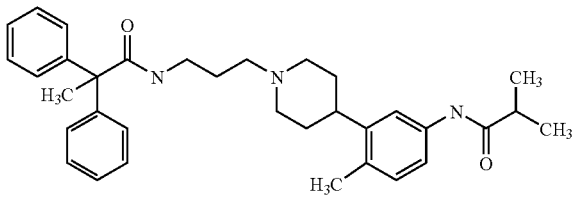

N-(3-{4-[5-(ISOBUTYRYLAMINO)-2-METHYLPHENYL]-1-PIPERIDINYL}PROPYL)-2,2-DIPHENYLPROPANAMIDE

Example 96 was prepared from 2,2-diphenylpropanoic acid and N-{3-[1-(3-aminopropyl)-4-piperidinyl]-4-methylphenyl}-2-methylpropanamide according to the procedures described in Scheme 10: $^1$H NMR (400 MHz, CDCl$_3$) δ 7.37–7.23 (m, 13H), 7.08 (d, 1H, J=8.8 Hz), 6.14 (t, 1H, J=5.6 Hz), 3.37 (dd, 2H, J=6.4, 12.0 Hz), 2.90 (d, 2H, J=11.6 Hz), 2.63 (m, 1H), 2.49 (m, 1H), 2.31 (t, 2H, J=6.8 Hz), 2.27 (s, 3H), 2.02 (s, 3H), 1.99–1.94 (m, 2H), 1.71–1.59 (m, 6H), 1.25 (d, 6H, J=7.2 Hz); ESMS m/e: 526.3 (M+H)$^+$.

EXAMPLE 97

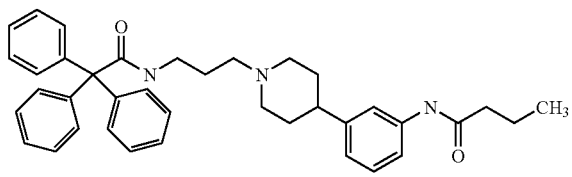

N-[3-(1-{3-[(2,2,2-TRIPHENYLACETYL)AMINO]PROPYL}-4-PIPERIDINYL)PHENYL]BUTANAMIDE

Example 97 was prepared from triphenylacetic acid and N-{3-[1-(3-aminopropyl)-4-piperidinyl]phenyl}butanamide according to the procedures described in Scheme 10: $^1$H NMR (400 MHz, CDCl$_3$) δ 7.39 (d, 2H, J=10.4 Hz), 7.34–7.21 (m, 17H), 6.90 (d, 1H, J=7.6 Hz), 6.31 (t, 1H, J=5.2 Hz), 3.43 (dd, 2H, J=6.4, 12.4 Hz), 2.87 (d, 2H, J=12.0 Hz), 2.41 (m, 1H), 2.31 (m, 4H), 1.92 (t, 2H, J=11.6 Hz), 1.79–1.66 (m, 6H), 1.59–1.52 (m, 2H), 1.01 (t, 3H, J=7.2 Hz); ESMS m/e: 574.4 (M+H)$^+$.

EXAMPLE 98

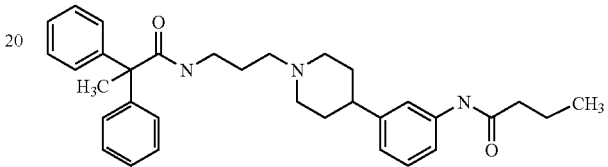

N-[3-(1-{3-[(2,2-DIPHENYLPROPANOYL)AMINO]PROPYL}-4-PIPERIDINYL)PHENYL]BUTANAMIDE

Example 98 was prepared from 2,2-diphenylpropanoic acid and N-{3-[1-(3-aminopropyl)-4-piperidinyl]phenyl}butanamide according to the procedures described in Scheme 10: $^1$H NMR (400 MHz, CDCl$_3$) δ 7.43 (s, 1H), 7.37–7.22 (m, 13H), 6.91 (d, 1H, J=7.2 Hz), 6.24 (br s, 1H), 3.37 (dd, 2H, J=5.6, 11.6 Hz), 2.88 (d, 2H, J=11.6 Hz), 2.42 (m, 1H), 2.32 (m, 4H), 2.01 (s, 3H), 1.93 (t, 2H, J=11.6 Hz), 1.81–1.52 (m, 8H), 1.01 (t, 3H, J=6.8 Hz); ESMS m/e: 512.3 (M+H)$^+$.

EXAMPLE 99

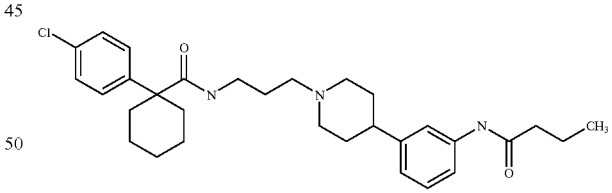

N-(3-{4-[3-(BUTYRYLAMINO)PHENYL]-1-PIPERIDINYL}PROPYL)-1-(4-CHLOROPHENYL)CYCLOHEXANECARBOXAMIDE

Example 99 was prepared from 1-(4-chlorophenyl)cyclohexanecarboxylic acid and N-{3-[1-(3-aminopropyl)-4-piperidinyl]phenyl}butanamide according to the procedures described in Scheme 10: $^1$H NMR (400 MHz, CDCl$_3$) δ 7.59 (s, 1H), 7.52 (s, 1H), 7.38–7.35 (m, 2H), 7.30–7.22 (m, 4H), 6.93 (d, 1H, J=7.6 Hz), 6.87 (br s, 1H), 3.28 (dd, 2H, J=6.0, 12.0 Hz), 2.92 (d, 2H, J=11.6 Hz), 2.45 (m, 1H), 2.36–2.30 (m, 6H), 1.96–1.33 (m, 18H), 1.00 (t, 3H, J=7.6 Hz); ESMS m/e: 524.3 (M+H)$^+$.

EXAMPLE 100

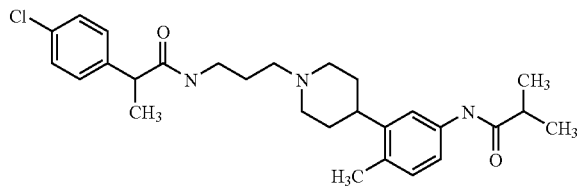

2-(4-CHLOROPHENYL)-N-(3-{4-[5-(ISOBU-TYRYLAMINO)-2-METHYLPHENYL]-1-PIPERIDINYL}PROPYL)PROPANAMIDE

Example 100 was prepared from 2-(4-chlorophenyl)propanoic acid and N-{3-[1-(3-aminopropyl)-4-piperidinyl]-4-methylphenyl}-2-methylpropanamide according to the procedures described in Scheme 10: $^1$H NMR (400 MHz, CDCl$_3$) δ 7.56 (d, 1H, J=2.0 Hz), 7.34–7.28 (m, 5H), 7.21 (dd, 1H, J=2.0. 8.0 Hz), 7.09 (d, 1H, J=8.0 Hz), 6.98 (br s, 1H), 3.55 (q, 1H, J=7.2 Hz), 3.34 (m, 2H), 3.02 (d, 1H, J=11.6 Hz), 2.93 (d, 1H, J=11.6 Hz), 2.68 (m, 1H), 2.51 (m, 1H), 2.39 (dt, 2H, J=6.8, 2.0 Hz), 2.29 (s, 3H), 2.04–1.97 (m, 2H), 1.80–1.60 (m, 6H), 1.52 (d, 3H, J=7.2 Hz), 1.24 (dd, 6H, J=1.6, 6.8 Hz); ESMS m/e: 484.3 (M+H)$^+$.

EXAMPLE 101

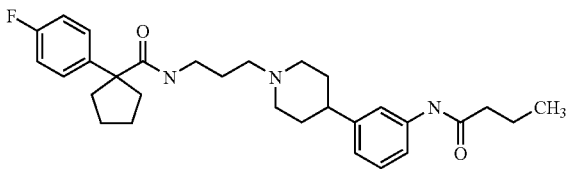

N-(3-{4-[3-(BUTYRYLAMINO)PHENYL]-1-PIPERIDINYL}PROPYL)-1-(4-FLUOROPHE-NYL)CYCLOPENTANECARBOXAMIDE

Example 101 was prepared from 1-(4-fluorophenyl)cyclopentanecarboxylic acid and N-{3-[1-(3-aminopropyl)-4-piperidinyl]phenyl}butanamide according to the procedures described in Scheme 10: $^1$H NMR (400 MHz, CDCl$_3$) δ 7.51 (s, 1H), 7.37–7.24 (m, 6H), 7.02–6.95 (m, 2H), 6.51 (br s, 1H), 3.28 (dd, 2H, J=5.6, 11.6 Hz), 2.93 (d, 2H, J=11.6 Hz), 2.53–2.48 (m, 3H), 2.37–2.30 (m, 4H), 1.98–1.92 (m, 4H), 1.82–1.59 (m, 12H), 1.02 (t, 3H, J=7.6 Hz); ESMS m/e: 494.3 (M+H)$^+$.

EXAMPLE 102

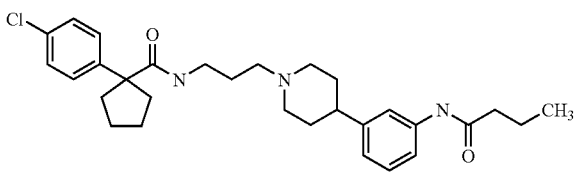

N-(3-{4-[3-(BUTYRYLAMINO)PHENYL]-1-PIPERIDINYL}PROPYL)-1-(4-CHLOROPHE-NYL)CYCLOPENTANECARBOXAMIDE

Example 102 was prepared from 1-(4-chlorophenyl)cyclopentanecarboxylic acid and N-{3-[1-(3-aminopropyl)-4-piperidinyl]phenyl}butanamide according to the procedures described in Scheme 10: $^1$H NMR (400 MHz, CDCl$_3$) δ 7.51 (s, 1H), 7.42 (s, 1H), 7.34–7.24 (m, 6H), 6.95 (d, 1H, J=7.6 Hz), 6.57 (br s, 1H), 3.28 (dd, 2H, J=5.6, 11.6 Hz), 2.92 (d, 2H, J=12.0 Hz), 2.53–2.43 (m, 3H), 2.37–2.29 (m, 4H), 1.99–1.91 (m, 4H), 1.83–1.58 (m, 12H), 1.02 (t, 3H, J=7.6 Hz); ESMS m/e: 510.3 (M+H)$^+$.

EXAMPLE 103

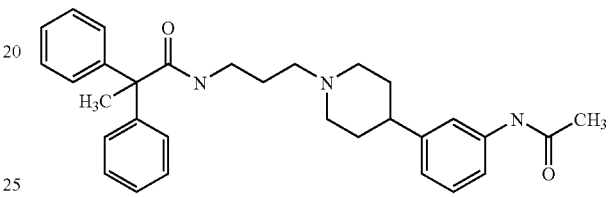

N-(3-{4-[3-(ACETYLAMINO)PHENYL]-1-PIPERIDINYL}PROPYL)-2,2-DIPHENYLPRO-PANAMIDE

Example 103 was prepared from 2,2-diphenylpropanoic acid and N-{3-[1-(3-aminopropyl)-4-piperidinyl]phenyl}acetamide according to the procedures described in Scheme 10: $^1$H NMR (400 MHz, CDCl$_3$) δ 7.37–7.23 (m, 14H), 6.93 (d, 1H, J=7.6 Hz), 6.20 (br s, 1H), 3.37 (dd, 2H, J=6.4, 12.4 Hz), 2.89 (d, 2H, 7.2 Hz), 2.45 (m, 1H), 2.30 (m, 2H), 2.18 (s, 3H), 2.01 (s, 3H), 1.94 (t, 2H, J=11.6 Hz), 1.76–1.53 (m, 6H); ESMS m/e: 484.2 (M+H)$^+$.

EXAMPLE 104

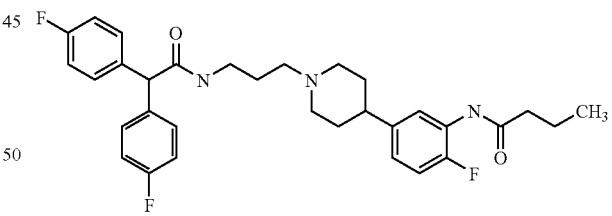

N-{5-[1-(3-{[BIS(4-FLUOROPHENYL)ACETYL]AMINO}PROPYL)-4-PIPERIDINYL]-2-FLUOROPHENYL}BUTANAMIDE

Example 104 was prepared from bis(4-fluorophenyl)acetic acid and N-{5-[1-(3-aminopropyl)-4-piperidinyl]-2-fluorophenyl}butanamide according to the procedures described in Scheme 10: $^1$H NMR (400 MHz, CDCl$_3$) δ 8.33–8.14 (m, 1H), 7.89–7.67 (br, 1H), 7.51–6.60 (m, 10H), 4.98–4.79 (br, 1H), 4.75 (s, 1H), 3.46–3.29 (m, 2H), 3.29–3.08 (m, 2H), 2.79–2.63 (m, 2H), 2.63–2.46 (m, 1H), 2.46–2.21 (m, 4H), 1.97–1.60 (m, 8H), 1.01 (t, 3H, J=7.2 Hz); ESMS m/e: 552.3 (M+H)$^+$.

EXAMPLE 105

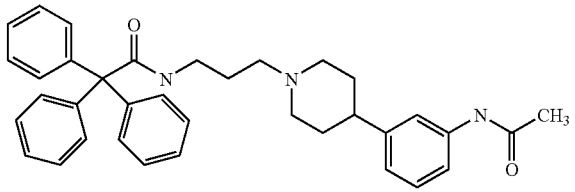

N-(3-{4-[3-(ACETYLAMINO)PHENYL]-1-PIPERIDINYL}PROPYL)-2,2,2-TRIPHENYLACETAMIDE

Example 105 was prepared from triphenylacetic acid and N-{3-[1-(3-aminopropyl)-4-piperidinyl]phenyl}acetamide according to the procedures described in Scheme 10: $^1$H NMR (400 MHz, CDCl$_3$) δ 7.34–7.22 (m, 19H), 6.91 (d, 1H, J=7.6 Hz), 6.30 (t, 1H, J=5.6 Hz), 3.43 (dd, 2H, J=6.4, 12.0 Hz), 2.87 (d, 2H, J=12.0 Hz), 2.42 (m, 1H), 2.30 (t, 2H, J=6.8 Hz), 2.17 (s, 3H), 1.93 (t, 2H, J=11.6 Hz), 1.74–1.66 (m, 4H), 1.60–1.50 (m, 2H); ESMS m/e: 546.2 (M+H)$^+$.

EXAMPLE 106

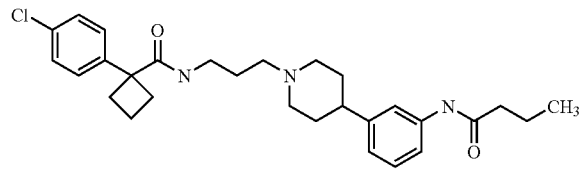

N-(3-{4-[3-(BUTYRYLAMINO)PHENYL]-1-PIPERIDINYL}PROPYL)-1-(4-CHLOROPHENYL)CYCLOBUTANECARBOXAMIDE

Example 106 was prepared from 1-(4-chlorophenyl)cyclobutanecarboxylic acid and N-{3-[1-(3-aminopropyl)-4-piperidinyl]phenyl}butanamide according to the procedures described in Scheme 10: $^1$H NMR (400 MHz, CDCl$_3$) δ 7.53 (s, 2H), 7.32–7.23 (m, 6H), 6.95 (d, 1H, J=7.6 Hz), 6.53 (br s, 1H), 3.29 (dd, 2H, J=6.0, 12.4 Hz), 2.93 (d, 2H, J=10.8 Hz), 2.86–2.79 (m, 2H), 2.48–2.41 (m, 3H), 2.37–2.30 (m, 4H), 2.07 (m, 1H), 1.98–1.61 (m, 11H), 1.01 (t, 3H, J=7.6 Hz); ESMS m/e: 496.3 (M+H)$^+$.

EXAMPLE 107

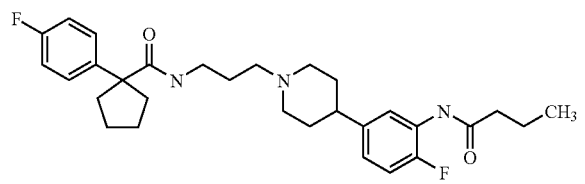

N-(3-{4-[3-(BUTYRYLAMINO)-4-FLUOROPHENYL]-1-PIPERIDINYL}PROPYL)-1-(4-FLUOROPHENYL)CYCLOPENTANECARBOXAMIDE

Example 107 was prepared from 1-(4-fluorophenyl)cyclopentanecarboxylic acid and N-{5-[1-(3-aminopropyl)-4-piperidinyl]-2-fluorophenyl}butanamide according to the procedures described in Scheme 10: $^1$H NMR (400 MHz, CDCl$_3$) δ 8.30–8.13 (m, 1H), 8.09–7.95 (br, 1H), 7.47–7.26 (m, 3H), 7.08–6.87 (m, 3H), 6.75–6.54 (br, 1H), 3.30–3.07 (m, 4H), 2.59–2.44 (m, 3H), 2.44–2.33 (m, 2H), 2.33–2.19 (m, 2H), 1.99–1.69 (m, 16H), 1.02 (t, 3H, J=7.2 Hz); ESMS m/e: 512.3 (M+H)$^+$.

EXAMPLE 108

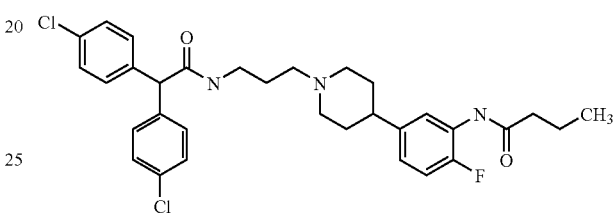

N-{5-[1-(3-{[BIS(4-CHLOROPHENYL)ACETYL]AMINO}PROPYL)-4-PIPERIDINYL]-2-FLUOROPHENYL}BUTANAMIDE

Example 108 was prepared from bis(4-chlorophenyl)acetic acid and N-{5-[1-(3-aminopropyl)-4-piperidinyl]-2-fluorophenyl}butanamide according to the procedures described in Scheme 10: ESMS m/e: 584.2 (M+H)$^+$.

EXAMPLE 109

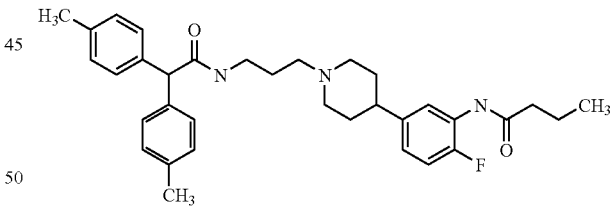

N-{5-[1-(3-{[BIS(4-METHYLPHENYL)ACETYL]AMINO}PROPYL)-4-PIPERIDINYL]-2-FLUOROPHENYL}BUTANAMIDE

Example 109 was prepared from bis(4-methylphenyl)acetic acid and N-{5-[1-(3-aminopropyl)-4-piperidinyl]-2-fluorophenyl}butanamide according to the procedures described in Scheme 10: $^1$H NMR (400 MHz, CDCl$_3$) δ 8.30–8.13 (m, 1H), 8.08–7.92 (br, 1H), 7.43–6.89 (m, 9H), 6.76–6.61 (br, 1H), 4.98–4.79 (br, 1H), 4.70 (s, 1H), 3.39–3.16 (m, 4H), 2.83–2.63 (m, 2H), 2.63–2.47 (m, 1H), 2.45–2.12 (m, 4H), 2.27 (s, 6H), 2.02–1.64 (m, 8H), 1.02 (t, 3H, J=7.2 Hz); ESMS m/e: 544.4 (M+H)$^+$.

EXAMPLE 110

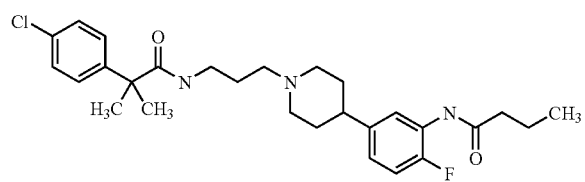

N-{5-[1-(3-{[2-(4-CHLOROPHENYL)-2-METH-YLPROPANOYL]AMINO}PROPYL)-4-PIPERIDI-NYL]-2-FLUOROPHENYL}BUTANAMIDE

Example 110 was prepared from 2-(4-chlorophenyl)-2-methylpropanoic acid and N-{5-[1-(3-aminopropyl)-4-piperidinyl]-2-fluorophenyl}butanamide according to the procedures described in Scheme 10: $^1$H NMR (400 MHz, CDCl$_3$) δ 8.31–8.12 (m, 1H), 7.44–7.15 (m, 5H), 7.12–6.94 (m, 1H), 6.75–6.61 (br, 1H), 6.61–6.46 (br, 1H), 3.35–3.12 (m, 4H), 2.70–2.47 (m, 3H), 2.46–2.35 (m, 2H), 2.35–2.21 (m, 2H), 1.92–1.67 (m, 8H), 1.54 (s, 6H), 1.02 (t, 3H, J=7.2 Hz); ESMS m/e: 502.3 (M+H)$^+$.

EXAMPLE 111

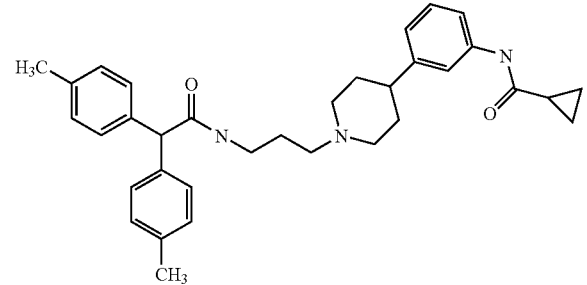

N-{3-[1-(3-{[2,2-BIS(4-METHYLPHENYL)ACETYL]AMINO}PROPYL)-4-PIPERIDINYL]PHENYL}CYCLOPROPANECARBOXAMIDE

Example 111 was prepared from bis(4-methylphenyl)acetic acid and N-{3-[1-(3-aminopropyl)-4-piperidinyl]phenyl}-cyclopropanecarboxamide according to the procedures described in Scheme 10: $^1$H NMR (400 MHz, CDCl$_3$) δ 8.24–8.04 (br, 1H), 8.04–7.95 (br, 1H), 7.59–6.92 (m, 10H), 6.90–6.76 (m, 1H), 4.98–4.82 (br, 1H), 4.72 (s, 1H), 3.42–3.25 (m, 2H), 3.25–3.08 (m, 2H), 2.75–2.56 (m, 2H), 2.56–2.40 (m, 1H), 2.35–2.17 (m, 2H), 2.26 (s, 6H), 1.99–1.68 (m, 6H), 1.57–1.44 (m, 1H), 1.12–0.99 (m, 2H), 0.87–0.70 (m, 2H); ESMS m/e: 524.3 (M+H)$^+$; Anal. Calc. for (HCl salt) C$_{34}$H$_{42}$ClF$_2$N$_3$O$_2$·0.29CHCl$_3$: C, 69.23; H, 7.16; N, 7.06. Found: C, 68.96; H, 7.35; N, 7.31.

EXAMPLE 112

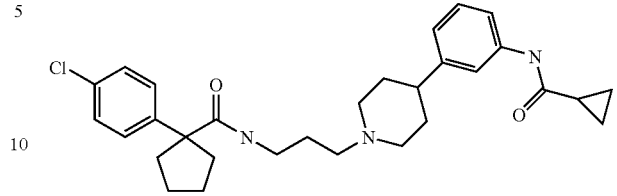

1-(4-CHLOROPHENYL)-N-[3-(4-{3-[(CYCLO-PROPYLCARBONYL)AMINO]PHENYL}-1-PIP-ERIDINYL)PROPYL]CYCLOPENTANECAR-BOXAMIDE

Example 112 was prepared from 1-(4-chlorophenyl)cyclopentanecarboxylic acid and N-{3-[1-(3-aminopropyl)-4-piperidinyl]phenyl}cyclopropanecarboxamide according to the procedures described in Scheme 10: $^1$H NMR (400 MHz, CDCl$_3$) δ 8.03–7.87 (br, 1H), 7.56–7.02 (m, 8H), 6.91–6.65 (br, 1H), 3.30–3.05 (m, 4H), 2.62–2.38 (m, 3H), 2.38–2.21 (m, 2H), 1.98–1.51 (m, 15H), 1.14–1.01 (m, 2H), 0.93–0.70 (m, 2H) ESMS m/e: 508.2 (M+H)$^+$.

EXAMPLE 113

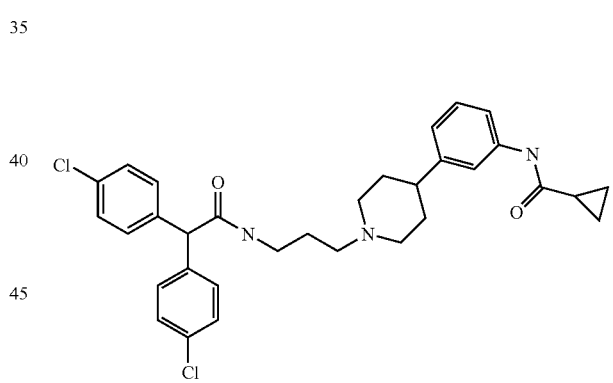

N-{3-[1-(3-{[2,2-BIS(4-CHLOROPHENYL)ACETYL]AMINO}PROPYL)-4-PIPERIDINYL]PHENYL}CYCLOPROPANECARBOXAMIDE

Example 113 was prepared from bis(4-chlorophenyl)acetic acid and N-{3-[1-(3-aminopropyl)-4-piperidinyl]phenyl}cyclopropanecarboxamide according to the procedures described in Scheme 10: $^1$H NMR (400 MHz, CDCl$_3$) δ 7.84–7.80 (br, 1H), 7.80–7.69 (br, 1H), 7.64–7.46 (br, 1H), 7.40–6.90 (m, 9H), 6.85–6.66 (m, 1H), 4.94–4.74 (br, 1H), 4.69 (s, 1H), 3.41–3.25 (m, 2H), 3.25–3.07 (m, 2H), 2.77–2.61 (m, 2H), 2.61–2.45 (m, 1H), 2.45–2.17 (m, 2H), 1.99–1.63 (m, 6H), 1.61–1.39 (m, 1H), 1.14–0.94 (m, 2H), 0.92–0.70 (m, 2H); ESMS m/e: 564.2 (M+H)$^+$.

EXAMPLE 114

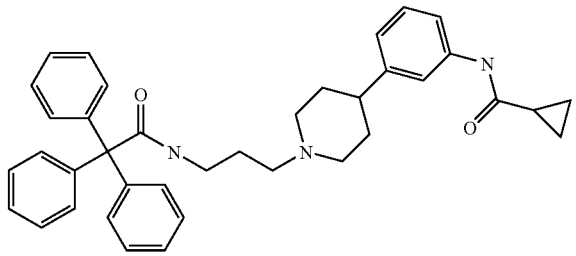

N-[3-(1-{3-[(2,2,2-TRIPHENYLACETYL)AMINO]PROPYL}-4-PIPERIDINYL)PHENYL]CYCLOPROPANECARBOXAMIDE

Example 114 was prepared from triphenylacetic acid and N-{3-[1-(3-aminopropyl)-4-piperidinyl]phenyl}cyclopropanecarboxamide according to the procedures described in Scheme 10: ESMS m/e: 572.3 (M+H)+.

EXAMPLE 115

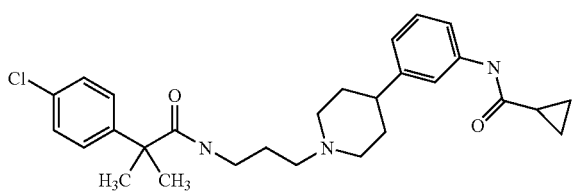

N-{3-[1-(3-{[2-(4-CHLOROPHENYL)-2-METHYLPROPANOYL]AMINO}PROPYL)-4-PIPERIDINYL]PHENYL}CYCLOPROPANECARBOXAMIDE

Example 115 was prepared from 2-(4-chlorophenyl)-2-methylpropanoic acid and N-{3-[1-(3-aminopropyl)-4-piperidinyl]phenyl}cyclopropanecarboxamide according to the procedures described in Scheme 10: $^1$H NMR (400 MHz, CDCl$_3$) δ 7.94–7.81 (br, 1H), 7.53–7.40 (br, 1H), 7.39–7.15 (m, 6H), 6.82 (d, 1H, J=7.2 Hz), 6.68–6.49 (br, 1H), 3.33–3.19 (m, 2H), 3.19–3.06 (m, 2H), 2.63–2.39 (m, 3H), 2.31–2.09 (m, 2H), 1.89–1.62 (m, 7H), 1.54 (s, 6H), 1.13–0.98 (m, 2H), 0.90–0.72 (m, 2H); ESMS m/e: 482.2 (M+H)+.

EXAMPLE 116

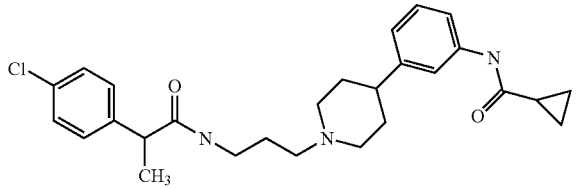

N-{3-[1-(3-{[2-(4-CHLOROPHENYL)PROPANOYL]AMINO}PROPYL)-4-PIPERIDINYL]PHENYL}CYCLOPROPANECARBOXAMIDE

Example 116 was prepared from 2-(4-chlorophenyl)propanoic acid and N-{3-[1-(3-aminopropyl)-4-piperidinyl]phenyl}cyclopropanecarboxamide according to the procedures described in Scheme 9: $^1$H NMR (400 MHz, CDCl$_3$) δ 8.15–7.95 (br, 1H), 7.63–7.44 (br, 1H), 7.39–7.12 (m, 7H), 6.85 (d, 1H, J=6.8 Hz), 3.74–3.55 (m, 1H), 3.45–3.22 (m, 2H), 3.22–3.12 (m, 1H), 3.12–3.00 (m, 1H), 2.66–2.40 (m, 3H), 2.29–2.09 (m, 2H), 1.92–1.63 (m, 6H), 1.64–1.51 (m, 1H), 1.47 (d, 3H, J=6.8 Hz), 1.18–0.98 (m, 2H), 0.91–0.74 (m, 2H); ESMS m/e: 468.2 (M+H)+; Anal. Calc. for (HCl salt) C$_{27}$H$_{35}$Cl$_2$N$_3$O$_2$·0.28CHCl$_3$: C, 60.91; H, 6.61; N, 7.81; Found: C, 60.66; H, 6.90; N, 8.19.

EXAMPLE 117

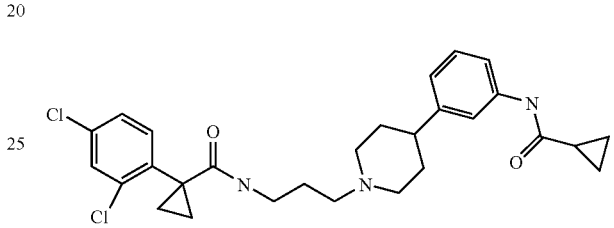

N-[3-(4-{3-[(CYCLOPROPYLCARBONYL)AMINO]PHENYL}-1-PIPERIDINYL)PROPYL]-1-(2,4-DICHLOROPHENYL)CYCLOPROPANECARBOXAMIDE

Example 117 was prepared from 1-(2,4-dichlorophenyl)cyclopropanecarboxylic acid and N-{3-[1-(3-aminopropyl)-4-piperidinyl]phenyl}cyclopropanecarboxamide according to the procedures described in Scheme 10: $^1$H NMR (400 MHz, CDCl$_3$) δ 8.00–7.82 (br, 1H), 7.52–7.04 (m, 6H), 6.86 (d, 1H, J=7.2 Hz), 5.92–5.73 (br, 1H), 3.35–3.12 (m, 4H), 2.74–2.58 (m, 2H), 2.58–2.42 (m, 1H), 2.40–2.20 (m, 2H), 2.01–1.61 (m, 7H), 1.15–0.90 (m, 6H), 0.89–0.71 (m, 2H); ESMS m/e: 514.2 (M+H)+.

EXAMPLE 118

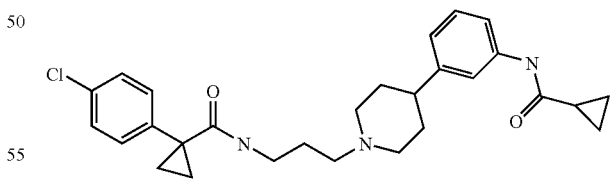

1-(4-CHLOROPHENYL)-N-[3-(4-{3-[(CYCLOPROPYLCARBONYL)AMINO]PHENYL}-1-PIPERIDINYL)PROPYL]CYCLOPROPANECARBOXAMIDE

Example 118 was prepared from 1-(4-chlorophenyl)cyclopropanecarboxylic acid and N-{3-[1-(3-aminopropyl)-4-piperidinyl]phenyl}cyclopropanecarboxamide according to the procedures described in Scheme 10: $^1$H NMR (400 MHz, CDCl$_3$) δ 8.12–7.88 (br, 1H), 7.48–7.14 (m, 7H), 6.85 (d, 1H, J=7.2 Hz), 5.83–5.66 (br, 1H), 3.29–3.09 (m, 4H), 2.66–2.53 (m, 2H), 2.53–2.40 (m, 1H), 2.37–2.17 (m, 2H), 1.95–1.53 (m, 7H), 1.14–0.91 (m, 6H), 0.89–0.71 (m, 2H); ESMS m/e: 480.2 (M+H)$^+$; Anal. Calc. (HCl salt) C$_{28}$H$_{35}$Cl$_2$N$_3$O$_2$.0.38CHCl$_3$: C, 60.64; H, 6.34; N, 7.47. Found: C, 60.38; H, 6.57; N, 7.80.

EXAMPLE 119

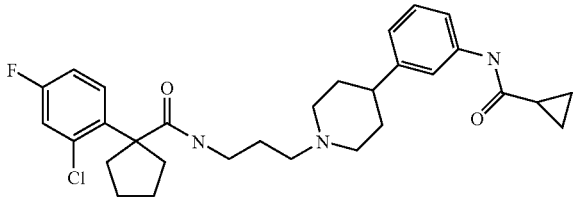

1-(2-CHLORO-4-FLUOROPHENYL)-N-[3-(4-{3-[(CYCLOPROPYLCARBONYL)AMINO]PHENYL}-1-PIPERIDINYL)PROPYL]CYCLOPENTANECARBOXAMIDE

Example 119 was prepared from 1-(2-chloro-4-fluorophenyl)cyclopentanecarboxylic acid and N-{3-[1-(3-aminopropyl-4-piperidinyl]phenyl}cyclopropanecarboxamide according to the procedures described in Scheme 10: ESMS m/e: 526.2 (M+H)$^+$.

EXAMPLE 120

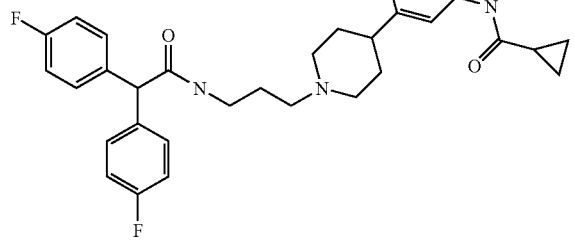

N-{3-[1-(3-{[2,2-BIS(4-FLUOROPHENYL)ACETYL]AMINO}PROPYL)-4-PIPERIDINYL]PHENYL}CYCLOPROPANECARBOXAMIDE

Example 120 was prepared from bis(4-fluorophenyl)acetic acid and N-{3-[1-(3-aminopropyl)-4-piperidinyl]phenyl}cyclopropanecarboxamide according to the procedures described in Scheme 10: $^1$H NMR (400 MHz, CDCl$_3$) δ 7.64–7.55 (s, 1H), 7.55–7.47 (s, 1H), 7.47–7.37 (br, 1H), 7.36–7.17 (m, 6H), 7.05–6.95 (m, 4H), 6.95–6.87 (br, 1H), 4.81 (s, 1H), 3.47–3.35 (m, 2H), 3.07–2.94 (m, 2H), 2.58–2.41 (m, 3H), 2.15–1.99 (m, 2H), 1.90–1.79 (m, 2H), 1.79–1.60 (m, 4H), 1.59–1.44 (m, 1H), 1.13–0.99 (m, 2H), 0.90–0.75 (m, 2H); ESMS m/e: 532.2 (M+H)$^+$.

EXAMPLE 121

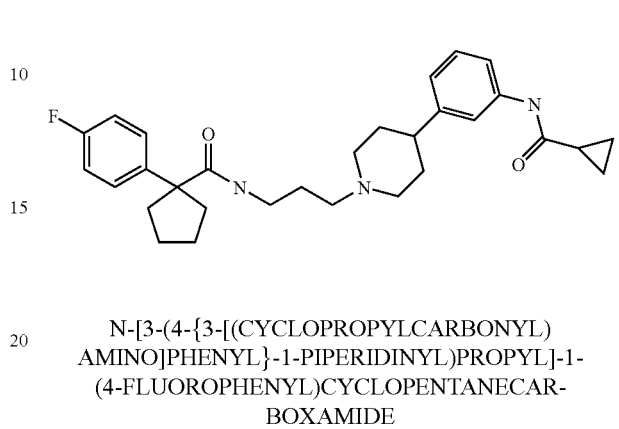

N-[3-(4-{3-[(CYCLOPROPYLCARBONYL)AMINO]PHENYL}-1-PIPERIDINYL)PROPYL]-1-(4-FLUOROPHENYL)CYCLOPENTANECARBOXAMIDE

Example 121 was prepared from 1-(4-fluorophenyl)cyclopentanecarboxylic acid and N-{3-[1-(3-aminopropyl)-4-piperidinyl]phenyl}cyclopropanecarboxamide according to the procedures described in Scheme 10: $^1$H NMR (400 MHz, CDCl$_3$) δ 7.94–7.72 (br, 1H), 7.48–6.84 (m, 7H), 6.75 (d, 1H, J=7.2 Hz), 6.68–6.55 (br, 1H), 3.25–3.05 (m, 4H), 2.58–2.39 (m, 3H), 2.33–2.15 (m, 2H), 2.00–1.48 (m, 15H), 1.13–1.01 (m, 2H), 0.93–0.73 (m, 2H); ESMS m/e: 492.3 (M+H)$^+$.

EXAMPLE 122

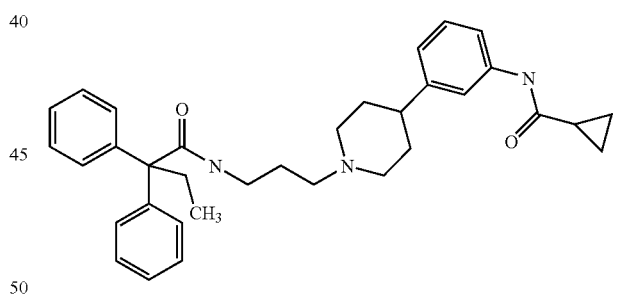

N-[3-(1-{3-[(2,2-DIPHENYLBUTANOYL)AMINO]PROPYL}-4-PIPERIDINYL)PHENYL]CYCLOPROPANECARBOXAMIDE

Example 122 was prepared from 2,2-diphenylbutanoic acid and N-{3-[1-(3-aminopropyl)-4-piperidinyl]phenyl}cyclopropanecarboxamide according to the procedures described in Scheme 10: $^1$H NMR (400 MHz, CDCl$_3$) δ 7.89–7.74 (br, 1H), 7.48–7.05 (m, 13H), 6.89–6.74 (d, 1H, J=7.2 Hz), 6.46–6.25 (br, 1H), 3.30–3.15 (m, 2H), 3.15–3.01 (m, 2H), 2.38–2.25 (m, 3H), 2.25–2.09 (m, 2H), 1.99–1.78 (m, 3H), 1.78–1.60 (m, 5H), 1.60–1.47 (m, 1H), 1.12–1.01 (m, 2H), 0.90–0.71 (m, 2H), 0.75 (t, 3H, J=7.2 Hz); ESMS m/e: 524.3 (M+H)$^+$.

EXAMPLE 123

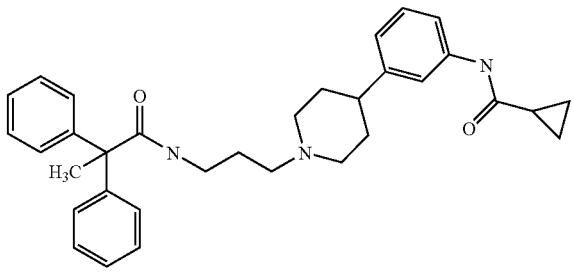

N-[3-(1-{3-[(2,2-DIPHENYLPROPANOYL) AMINO]PROPYL}-4-PIPERIDINYL)PHENYL] CYCLOPROPANECARBOXAMIDE

Example 123 was prepared from 2,2-diphenylpropanoic acid and N-{3-[1-(3-aminopropyl)-4-piperidinyl]phenyl}cyclopropanecarboxamide according to the procedures described in Scheme 10: ESMS m/e: 510.3 (M+H)$^+$.

EXAMPLE 124

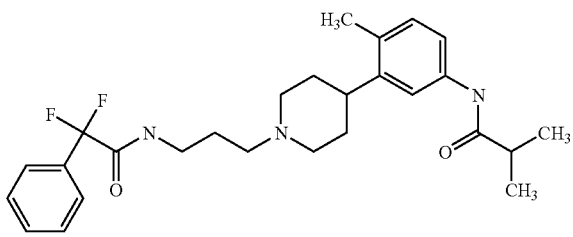

N-{3-[1-(3-{[DIFLUORO(PHENYL)ACETYL]AMINO}PROPYL)-4-PIPERIDINYL]-4-METHYLPHENYL}-2-METHYLPROPANAMIDE

Example 124 was prepared from 2,2-difluoro-2-phenylacetic acid and N-{3-[1-(3-aminopropyl)-4-piperidinyl]-4-methylphenyl}-2-methylpropanamide according to the procedures described in Scheme 9: $^1$H NMR (400 MHz, CDCl$_3$) δ 8.00 (s, 2H), 7.68–7.63 (m, 3H), 7.49–7.39 (m, 3H), 7.23 (d, 1H, J=1.8 Hz), 7.07 (d, 1H, J=8.3 Hz), 3.45 (q, 2H, J=4.9 Hz), 3.11 (d, 2H, J=10.2 Hz), 2.76–2.66 (m, 1H), 2.56 (t, 2H, J=5.0 Hz), 2.44 (septet, 1H, J=6.9 Hz), 2.28 (s, 3H), 2.13–2.05 (m, 2H), 1.82–1.71 (m, 6H), 1.15 (d, 6H, J=6.9 Hz); ESMS m/e: 472.4 (M+H)$^+$.

EXAMPLE 125

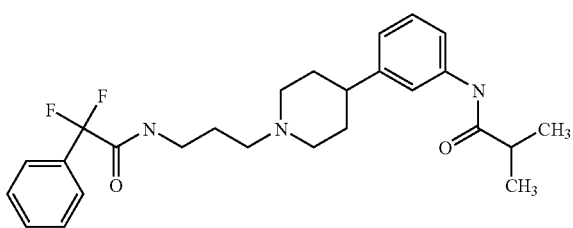

N-{3-[1-(3-{[DIFLUORO(PHENYL)ACETYL]AMINO}PROPYL)-4-PIPERIDINYL]PHENYL}-2-METHYLPROPANAMIDE

Example 125 was prepared from 2,2-difluoro-2-phenylacetic acid and N-{3-[1-(3-aminopropyl)-4-piperidinyl]phenyl}-2-methylpropanamide according to the procedures described in Scheme 10: $^1$H NMR (400 MHz, CDCl$_3$) δ 8.01 (s, 1H), 7.71 (s, 1H), 7.65–7.62 (m, 2H), 7.50 (s, 1H), 7.47–7.40 (m, 3H), 7.35 (d, 1H, J=7.6 Hz), 7.22 (t, 1H, J=7.2 Hz), 6.95 (d, 1H, J=7.8 Hz), 3.45 (q, 2H, J=5.3 Hz), 3.10 (d, 2H, J=10.9 Hz), 2.59–2.45 (m, 4H), 2.11–2.02 (m, 2H), 1.89–1.71 (m, 6H), 1.20 (d, 6H, J=6.9 Hz); ESMS m/e: 458.4 (M+H)$^+$.

EXAMPLE 126

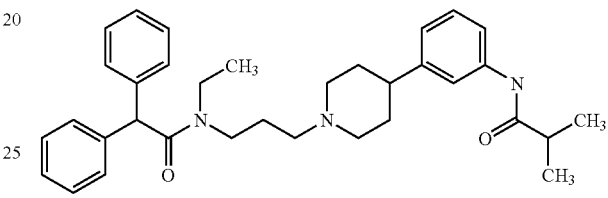

N-[3-(1-{3-[(DIPHENYLACETYL)(ETHYL)AMINO]PROPYL}-4-PIPERIDINYL)PHENYL]-2-METHYLPROPANAMIDE

Example 126 was prepared from diphenylacetyl chloride and N-(3-{1-[3-(ethylamino)propyl]-4-piperidinyl}phenyl)-2-methylpropanamide according to the procedures described in Scheme 8: $^1$H NMR (400 MHz, CDCl$_3$) δ 7.33–7.21 (m, 13H), 6.94 (m, 2H), 4.88 (s, 1H), 3.39 (m, 4H), 2.93 (d, 2H, J=10.9 Hz), 2.52–2.36 (m, 7H), 1.97 (t, 2H, J=10.9 Hz), 1.83–1.58 (m, 6H), 1.24 (d, 6H, J=7.6 Hz); ESMS m/e: 526.4 (M+H)$^+$.

EXAMPLE 127

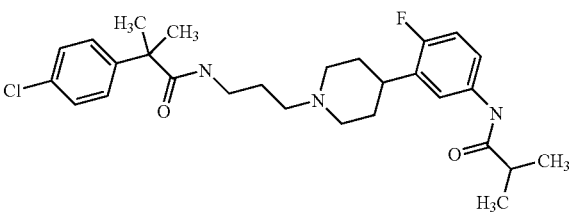

2-(4-CHLOROPHENYL)-N-(3-{4-[2-FLUORO-5-(ISOBUTYRYLAMINO)PHENYL]-1-PIPERIDINYL}PROPYL)-2-METHYLPROPANAMIDE

Example 127 was prepared from 2-(4-chlorophenyl)-2-methylpropanoic acid and N-{3-[1-(3-aminopropyl)-4-piperidinyl]-4-fluorophenyl}-2-methylpropanamide according to the procedures described in Scheme 9: $^1$H NMR (400 MHz, CDCl$_3$) δ 7.95 (s, 1H), 7.73 (s, 1H), 7.68 (s, 1H), 7.43–7.38 (m, 1H), 7.37–7.26 (m, 3H), 6.93–6.83 (m, 2H), 3.96–3.61 (m, 1H), 3.26–3.02 (m, 4H), 2.69–2.59 (m, 1H), 2.51–2.40 (m, 2H), 1.90–1.71 (m, 4H), 1.63–1.47 (m, 4H), 1.18 (d, 6H, J=6.9 Hz), 1.15 (s, 6H); ESMS m/e: 502.1 (M+H)+.

EXAMPLE 128

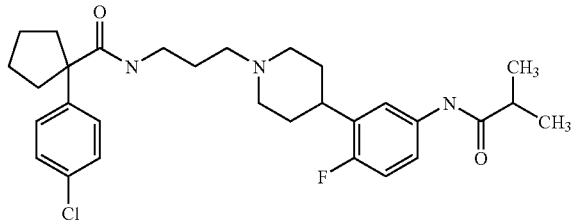

1-(4-CHLOROPHENYL)-N-(3-{4-[2-FLUORO-5-(ISOBUTYRYLAMINO)PHENYL]-1-PIPERIDINYL}PROPYL)CYCLOPENTANECARBOXAMIDE

Example 128 was prepared from 1-(4-chlorophenyl)cyclopentanecarboxylic acid and N-{3-[1-(3-aminopropyl)-4-piperidinyl]-4-fluorophenyl}-2-methylpropanamide according to the procedures described in Scheme 9: $^1$H NMR (400 MHz, CDCl$_3$) δ 7.45 (s, 1H), 7.42–7.38 (m, 1H), 7.27–7.17 (m, 4H), 7.12–7.09 (m, 1H), 6.87 (t, 1H, J=8.6 Hz), 6.49 (t, 1H, J=5.4 Hz), 3.19 (q, 2H, J=5.8 Hz), 2.85–2.79 (m, 2H), 2.73–2.64 (m, 1H), 2.50–2.35 (m, 3H), 2.23 (t, 2H, J=6.6 Hz), 1.92–1.85 (m, 4H), 1.75–1.48 (m, 10H), 1.17 (d, 6H, J=6.7 Hz); ESMS m/e: 528.2 (M+H)+.

EXAMPLE 129

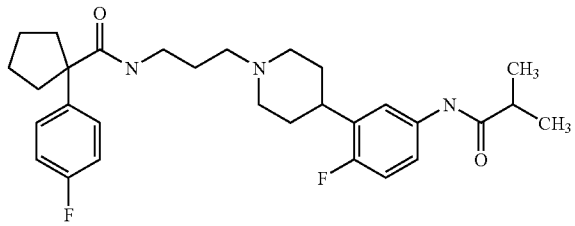

N-(3-{4-[2-FLUORO-5-(ISOBUTYRYLAMINO)PHENYL]-1-PIPERIDINYL}PROPYL)-1-(4-FLUOROPHENYL)CYCLOPENTANECARBOXAMIDE

Example 129 was prepared from 1-(4-fluorophenyl)cyclopentanecarboxylic acid and N-{3-[1-(3-aminopropyl)-4-piperidinyl]-4-fluorophenyl}-2-methylpropanamide according to the procedures described in Scheme 9: $^1$H NMR (400 MHz, CDCl$_3$) δ 7.53 (s, 1H), 7.42–7.38 (m, 1H), 7.31–7.20 (m, 2H), 6.94–6.83 (m, 4H), 6.46–6.40 (m, 1H), 3.19 (q, 2H, J=5.6 Hz), 2.85–2.79 (m, 2H), 2.73–2.64 (m, 1H), 2.49–2.38 (m, 3H), 2.22 (t, 2H, J=6.4 Hz), 1.94–1.84 (m, 5H), 1.75–1.47 (m, 9H), 1.17 (d, 6H, J=6.8 Hz); ESMS m/e: 512.3 (M+H)+.

EXAMPLE 130

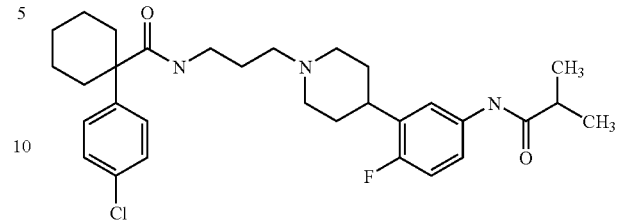

1-(4-CHLOROPHENYL)-N-(3-{4-[2-FLUORO-5-(ISOBUTYRYLAMINO)PHENYL]-1-PIPERIDINYL}PROPYL)CYCLOHEXANECARBOXAMIDE

Example 130 was prepared from 1-(4-chlorophenyl)cyclohexanecarboxylic acid and N-{3-[1-(3-aminopropyl)-4-piperidinyl]-4-fluorophenyl}-2-methylpropanamide according to the procedures described in Scheme 9: $^1$H NMR (400 MHz, CDCl$_3$) δ 7.45–7.40 (m, 1H), 7.34–7.29 (m, 3H), 7.24–7.16 (m, 3H), 6.88 (t, 1H, J=8.7 Hz), 6.77–6.72 (m, 1H), 3.21 (q, 2H, J=5.6 Hz), 2.87–2.81 (m, 2H), 2.74–2.65 (m, 1H), 2.44 (septet, 1H, J=6.7 Hz), 2.28–2.21 (m, 4H), 1.92–1.76 (m, 4H), 1.69–1.69 (m, 4H), 1.56–1.47 (m, 8H), 1.18 (d, 6H, J=6.7 Hz); ESMS m/e: 542.2 (M+H)+; Anal. Calc. for C$_{31}$H$_{41}$ClFN$_3$O$_2$.HCl.0.20 CHCl$_3$: C, 62.20; H, 7.06; N, 6.97. Found: C, 62.24; H, 7.03; N, 6.79.

EXAMPLE 131

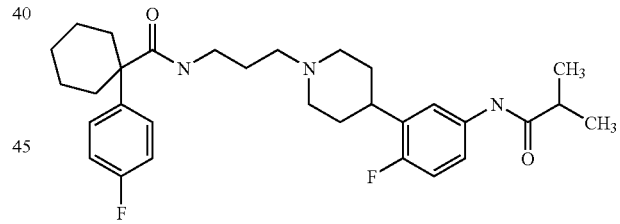

N-(3-{4-[2-FLUORO-5-(ISOBUTYRYLAMINO)PHENYL]-1-PIPERIDINYL}PROPYL)-1-(4-FLUOROPHENYL)CYCLOHEXANECARBOXAMIDE

Example 131 was prepared from 1-(4-fluorophenyl)cyclohexanecarboxylic acid and N-{3-[1-(3-aminopropyl)-4-piperidinyl]-4-fluorophenyl}-2-methylpropanamide according to the procedures described in Scheme 9: $^1$H NMR (400 MHz, CDCl$_3$) δ 7.49 (s, 1H), 7.43 (dd, 1H, J=6.9, 2.5 Hz), 7.36–7.31 (m, 2H), 7.23–7.17 (m, 1H), 6.93 (t, 2H, J=8.4 Hz), 6.87 (t, 1H, J=8.9 Hz), 6.73–6.68 (m, 1H), 3.21 (q, 2H, J=5.7 Hz), 2.87–2.80 (m, 2H), 2.73–2.65 (m, 1H), 2.45 (septet, 1H, J=6.7 Hz), 2.30–2.21 (m, 4H), 1.9–1.77 (m, 5H), 1.70–1.63 (m, 3H), 1.56–1.45 (m, 8H), 1.17 (d, 6H, J=6.7 Hz); ESMS m/e: 526.3 (M+H)+.

EXAMPLE 132

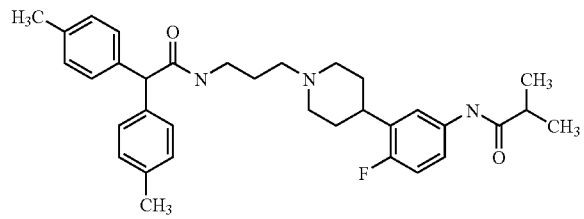

N-{3-[1-(3-{[BIS(4-METHYLPHENYL)ACETYL]AMINO}PROPYL)-4-PIPERIDINYL]-4-FLUOROPHENYL}-2-METHYLPROPANAMIDE

Example 132 was prepared from bis(4-methylphenyl)acetic acid and N-{3-[1-(3-aminopropyl)-4-piperidinyl]-4-fluorophenyl}-2-methylpropanamide according to the procedures described in Scheme 9: $^1$H NMR (400 MHz, CDCl$_3$) δ 7.72 (s, 1H), 7.36–7.31 (m, 1H), 7.28–7.21 (m, 1H), 7.12–7.07 (m, 3H), 7.03–6.99 (m, 5H), 6.86–6.80 (m, 1H), 6.79–6.75 (m, 1H), 4.74 (s, 1H), 3.33–3.25 (m, 2H), 2.85–2.77 (m, 2H), 2.72–2.62 (m, 1H), 2.40 (septet, 1H, J=6.7 Hz), 2.28 (t, 2H, J=6.6 Hz), 2.21 (m, 6H), 1.94–1.84 (m, 2H), 1.65–1.52 (m, 6H), 1.71 (d, 6H, J=6.6 Hz); ESMS m/e: 544.3 (M+H)$^+$; Anal. Calc. for C$_{34}$H$_{42}$FN$_3$O$_2$·HCl·0.10 CHCl$_3$: C, 70.17; H, 7.35; N, 7.10. Found: C, 70.35; H, 6.99; N, 7.10.

EXAMPLE 133

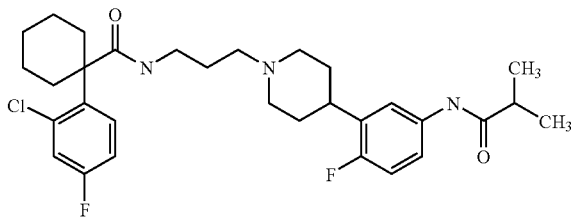

1-(2-CHLORO-4-FLUOROPHENYL)-N-(3-{4-[2-FLUORO-5-(ISOBUTYRYLAMINO)PHENYL]-1-PIPERIDINYL}PROPYL)CYCLOHEXANECARBOXAMIDE

Example 133 was prepared from 1-(2-chloro-4-fluorophenyl)cyclohexanecarboxylic acid and N-{3-[1-(3-aminopropyl)-4-piperidinyl]-4-fluorophenyl}-2-methylpropanamide according to the procedures described in Scheme 9: $^1$H NMR (400 MHz, CDCl$_3$) δ 7.59 (dd, 1H, J=6.4, 8.5 Hz), 7.44–7.38 (m, 2H), 7.35–7.30 (m, 1H), 7.13 (dd, 1H, J=8.5, 3.0 Hz), 7.00–6.91 (m, 2H), 6.05–5.99 (m, 1H), 3.30 (q, 2H, J=5.7 Hz), 2.92–2.86 (m, 2H), 2.80–2.71 (m, 1H), 2.52 (septet, 1H, J=6.7 Hz), 2.34 (t, 2H, J=5.7 Hz), 2.30–2.24 (m, 3H), 2.13–2.05 (m, 2H), 2.00–1.92 (m, 2H), 1.86–1.69 (m, 4H), 1.66–1.43 (m, 7H), 1.71 (d, 6H, J=6.7 Hz); ESMS m/e: 560.1 (M+H)$^+$.

EXAMPLE 134

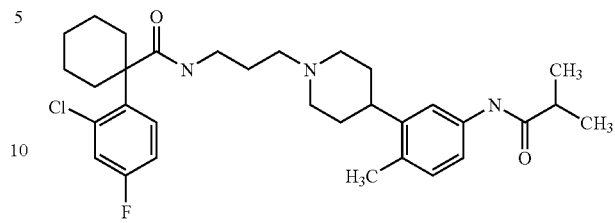

1-(2-CHLORO-4-FLUOROPHENYL)-N-(3-{4-[5-(ISOBUTYRYLAMINO)-2-METHYLPHENYL]-1-PIPERIDINYL}PROPYL)CYCLOHEXANECARBOXAMIDE

Example 134 was prepared from 1-(2-chloro-4-fluorophenyl)cyclohexanecarboxylic acid and N-{3-[1-(3-aminopropyl)-4-piperidinyl]-4-methylphenyl}-2-methylpropanamide according to the procedures described in Scheme 9: $^1$H NMR (400 MHz, CDCl$_3$) δ 7.55 (dd, 1H, J=8.9, 6.3 Hz), 7.32 (s, 1H), 7.23–7.18 (m, 2H), 7.06 (dd, 1H, J=8.5, 3.0 Hz), 7.01–6.92 (m, 2H), 5.99–5.93 (m, 1H), 3.24 (q, 2H, J=5.9 Hz), 2.85–2.79 (m, 3H), 2.59–2.50 (m, 1H), 2.44 (septet, 1H, J=7.0 Hz), 2.41–2.37 (br, 1H), 2.26 (t, 2H, J=5.7 Hz), 2.19 (s, 3H), 2.07–2.01 (m, 2H), 1.81–1.69 (m, 4H), 1.61–1.37 (m, 10H), 1.17 (d, 6H, J=7.0 Hz); ESMS m/e: 556.1 (M+H)$^+$.

EXAMPLE 135

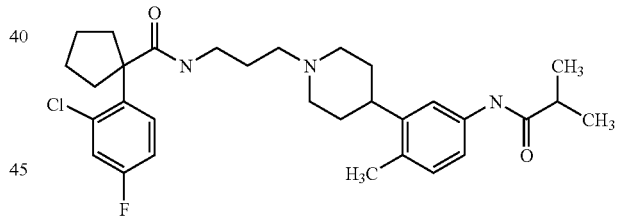

1-(2-CHLORO-4-FLUOROPHENYL)-N-(3-{4-[5-(ISOBUTYRYLAMINO)-2-METHYLPHENYL]-1-PIPERIDINYL}PROPYL)CYCLOPENTANECARBOXAMIDE

Example 135 was prepared from 1-(2-chloro-4-fluorophenyl)cyclopentanecarboxylic acid and N-{3-[1-(3-aminopropyl)-4-piperidinyl]-4-methylphenyl}-2-methylpropanamide according to the procedures described in Scheme 9: $^1$H NMR (400 MHz, CDCl$_3$) δ 7.56 (dd, 1H, J=8.7, 6.3 Hz), 7.32 (s, 1H), 7.22–7.15 (m, 2H), 7.06 (dd, 1H, J=8.7, 3.0 Hz), 7.05–6.95 (m, 2H), 5.90–5.84 (m, 1H), 3.21 (q, 2H, J=5.7 Hz), 2.87–2.80 (m, 2H), 2.59–2.49 (m, 1H), 2.44 (septet, 1H, J=6.5 Hz), 2.41–2.40 (m, 2H), 2.26 (t, 2H, J=5.7 Hz), 2.19 (s, 3H), 2.04–1.96 (m, 2H), 1.93–1.85 (m, 2H), 1.82–1.71 (m, 3H), 1.64–1.48 (m, 7H), 1.17 (d, 6H, J=6.5 Hz); ESMS m/e: 542.2 (M+H)$^+$.

EXAMPLE 136

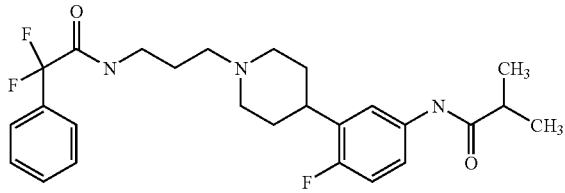

N-{3-[1-(3-{[DIFLUORO(PHENYL)ACETYL]
AMINO}PROPYL)-4-PIPERIDINYL]-4-FLUO-
ROPHENYL}-2-METHYLPROPANAMIDE

Example 136 was prepared from 2,2-difluoro-2-phenylacetic acid and N-{3-[1-(3-aminopropyl)-4-piperidinyl]-4-fluorophenyl}-2-methylpropanamide according to the procedures described in Scheme 9: $^1$H NMR (400 MHz, CDCl$_3$) δ 9.11 (s, 1H), 7.61–7.56 (m, 2H), 7.41–7.34 (m, 4H), 7.21–7.17 (m, 1H), 7.14 (s, 1H), 6.88 (t, 1H, J=9.5 Hz), 3.39 (q, 2H, J=5.7 Hz), 3.08–3.01 (m, 2H), 2.84–2.74 (m, 1H), 2.50 (t, 2H, J=5.1 Hz), 2.38 (septet, 1H, J=7.2 Hz), 2.08–1.99 (m, 2H), 1.81–1.73 (m, 4H), 1.72–1.64 (m, 2H), 1.17 (d, 6H, J=7.2 Hz); ESMS m/e: 476.2 (M+H)$^+$.

EXAMPLE 137

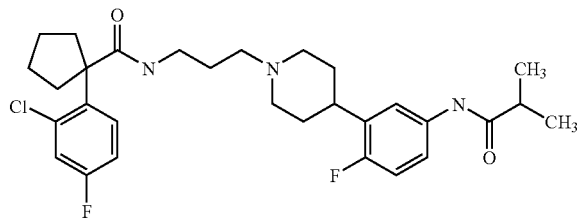

1-(2-CHLORO-4-FLUOROPHENYL)-N-(3-{4-[2-
FLUORO-5-(ISOBUTYRYLAMINO)PHENYL]-1-
PIPERIDINYL}PROPYL)CYCLOPENTANECAR-
BOXAMIDE

Example 137 was prepared from 1-(2-chloro-4-fluorophenyl)cyclopentanecarboxylic acid and N-{3-[1-(3-aminopropyl)-4-piperidinyl]-4-fluorophenyl}-2-methylpropanamide according to the procedures described in Scheme 9: ESMS m/e: 546.1 (M+H)$^+$.

EXAMPLE 138

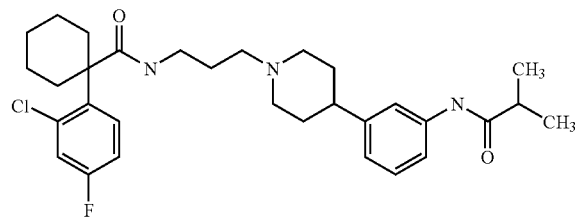

1-(2-CHLORO-4-FLUOROPHENYL)-N-(3-{4-[3-
(ISOBUTYRYLAMINO)PHENYL]-1-
PIPERIDINYL}PROPYL)CYCLOHEXANECAR-
BOXAMIDE

Example 138 was prepared from 1-(2-chloro-4-fluorophenyl)cyclohexanecarboxylic acid and N-{3-[1-(3-aminopropyl)-4-piperidinyl]phenyl}-2-methylpropanamide according to the procedures described in Scheme 9: $^1$H NMR (400 MHz, CDCl$_3$) δ 7.52–7.46 (m, 1H), 7.45–7.43 (m, 1H), 7.30 (s, 1H), 7.22 (s, 1H), 7.17 (t, 1H, J=7.9 Hz), 7.07–7.01 (m, 2H), 6.89–6.84 (m, 1H), 5.99–5.94 (m, 1H), 3.21 (q, 2H, J=5.7 Hz), 2.87–2.80 (m, 2H), 2.59–2.49 (m, 1H), 2.44 (septet, 1H, J=6.5 Hz), 2.41–2.40 (m, 2H), 2.26 (t, 2H, J=5.7 Hz), 2.04–1.96 (m, 2H), 1.93–1.85 (m, 2H), 1.82–1.71 (m, 4H), 1.64–1.50 (m, 8H), 1.17 (d, 6H, J=6.5 Hz); ESMS m/e: 542.1 (M+H)$^+$.

EXAMPLE 139

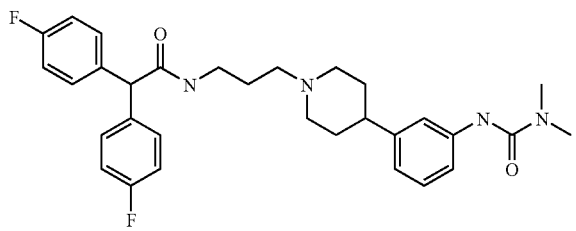

N-{3-[4-(3-{[(DIMETHYLAMINO)CARBONYL]
AMINO}PHENYL)-1-PIPERIDINYL]PROPYL}-2,
2-BIS(4-FLUOROPHENYL)ACETAMIDE

Example 139 was prepared from bis(4-fluorophenyl)acetic acid and N'-{3-[1-(3-aminopropyl)-4-piperidinyl]phenyl}-N,N-dimethylurea according to the procedures described in Scheme 9: ESMS m/e: 535.4 (M+H)$^+$.

EXAMPLE 140

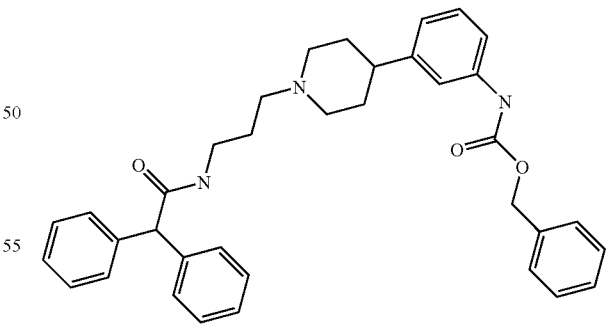

Benzyl 3-(1-{3-[(Diphenylacetyl)Amino]Propyl}-4-
Piperidinyl)Phenylcarbamate

Example 140 was prepared from diphenylacetyl chloride and benzyl 3-[1-(3-aminopropyl)-4-piperidinyl]phenylcarbamate according to the procedures described in Scheme 8: ESMS m/e: 562.5 (M+H)$^+$.

EXAMPLE 141

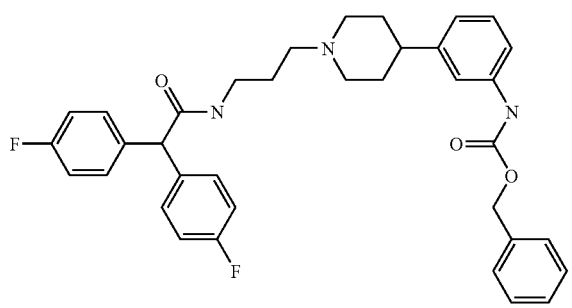

benzyl 3-[1-(3-{[bis(4-fluorophenyl)acetyl]
amino}propyl)-4-piperidinyl]phenylcarbamate Example 141 was prepared from bis(4-fluorophenyl)acetic acid and benzyl 3-[1-(3-aminopropyl)-4-piperidinyl]phenylcarbamate according to the procedures described in Scheme 9: ESMS m/e: 598.5 (M+H)+.

EXAMPLE 142

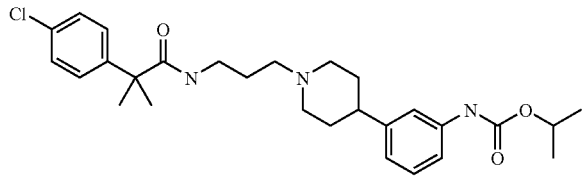

Isopropyl 3-[1-(3-{[2-(4-Chlorophenyl)-2-Methyl-
propanoyl]Amino}Propyl)-4-Piperidinyl]Phenylcarbamate Example 142 was prepared from 2-(4-chlorophenyl)-2-methylpropanoic acid and isopropyl 3-[1-(3-aminopropyl)-4-piperidinyl]phenylcarbamate according to the procedures described in Scheme 9: $^1$H NMR (400 MHz, CDCl$_3$) δ 7.29–7.22 (m, 3H), 7.20–7.11 (m, 3H), 7.09–7.06 (m, 1H), 6.79 (d, 1H, J=7.6 Hz), 6.61 (s, 1H), 6.60–6.50 (m, 1H), 4.94 (septet, 1H, J=6.7 Hz), 4.05 (q, 1H, J=6.8 Hz), 3.24 (q, 2H, J=5.9 Hz), 2.86–2.79 (m, 2H), 2.36 (tt, 1H, J=11.9, 3.2 Hz), 2.27 (t, 2H, J=6.3 Hz), 1.85 (t, 2H, J=11.9 Hz), 1.72–1.66 (m, 2H), 1.60–1.52 (m, 3H), 1.48 (s, 6H), 1.23 (d, 6H, J=6.7 Hz); ESMS m/e: 500.2 (M+H)+.

EXAMPLE 143

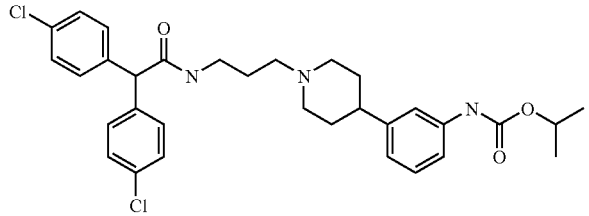

Isopropyl 3-[1-(3-{[bis(4-chlorophenyl)acetyl]
amino}propyl)-4-piperidinyl]phenylcarbamate Example 143 was prepared from bis(4-chlorophenyl)acetic acid and isopropyl 3-[1-(3-aminopropyl)-4-piperidinyl]phenylcarbamate according to the procedures described in Scheme 9: $^1$H NMR (400 MHz, CDCl$_3$) δ 7.46 (s, 1H), 7.37 (s, 1H), 7.23–7.10 (m, 9H), 7.00 (d, 1H, J=7.9 Hz), 6.80 (d, 1H, J=7.4 Hz), 6.60 (s, 1H), 4.88 (septet, 1H, J=6.2 Hz), 4.68 (s, 1H), 4.05 (q, 1H, J=7.3 Hz), 3.32 (q, 2H, J=5.9 Hz), 2.90–2.83 (m, 2H), 2.44–2.32 (m, 3H), 1.94–1.86 (m, 2H), 1.78–1.70 (m, 2H), 1.60 (quintet, 2H, J=6.4 Hz), 1.56–1.43 (m, 1H), 1.22 (d, 6H, J=6.2 Hz); ESMS m/e: 582.2 (M+H)+.

EXAMPLE 144

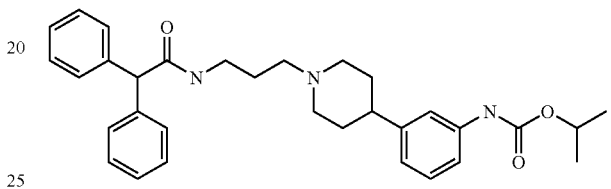

Isopropyl 3-(1-{3-[(Diphenylacetyl)Amino]Propyl}-
4-Piperidinyl)Phenylcarbamate

Example 144 was prepared from diphenylacetyl chloride and isopropyl 3-[1-(3-aminopropyl)-4-piperidinyl]phenylcarbamate according to the procedures described in Scheme 9: $^1$H NMR (400 MHz, CDCl$_3$) δ 7.25–7.12 (m, 12H), 7.09–7.06 (m, 1H), 7.00–6.94 (m, 1H), 6.79 (d, 1H, J=7.6 Hz), 6.60 (s, 1H), 4.92 (septet, 1H, J=6.2 Hz), 4.79 (s, 1H), 4.04 (q, 1H, J=6.4 Hz), 3.30 (q, 2H, J=5.8 Hz), 2.91–2.83 (m, 2H), 2.42–2.30 (m, 3H), 1.91 (t, 2H, J=11.4 Hz), 1.74–1.67 (m, 2H), 1.65–1.51 (m, 3H), 1.21 (d, 6H, J=6.2 Hz); ESMS m/e: 514.2 (M+H)+.

EXAMPLE 145

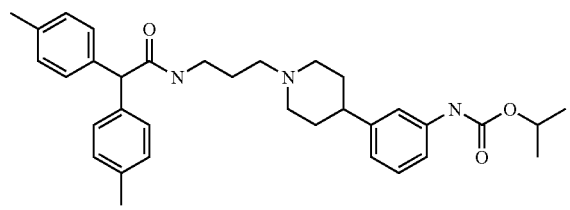

ISOPROPYL 3-[1-(3-{[BIS(4-METHYLPHENYL)
ACETYL]AMINO}PROPYL)-4-PIPERIDINYL]
PHENYLCARBAMATE

Example 145 was prepared from bis(4-methylphenyl) acetic acid and isopropyl 3-[1-(3-aminopropyl)-4-piperidinyl]phenylcarbamate according to the procedures described in Scheme 9: $^1$H NMR (400 MHz, CDCl$_3$) δ 7.24 (s, 1H), 7.18–7.06 (m, 4H), 7.06–7.00 (m, 6H), 6.82–6.78 (m, 2H), 6.62 (s, 1H), 4.92 (septet, 1H, J=6.7 Hz), 4.72 (s, 1H), 4.04 (q, 1H, J=6.8 Hz), 3.32–3.26 (m, 2H), 2.88–2.81 (m, 2H), 2.41–2.27 (m, 3H), 2.21 (s, 6H), 1.92–1.83 (m, 2H), 1.74–1.66 (m, 2H), 1.62–1.46 (m, 3H), 1.21 (d, 6H, J=6.7 Hz); ESMS m/e: 542.3 (M+H)+.

EXAMPLE 146

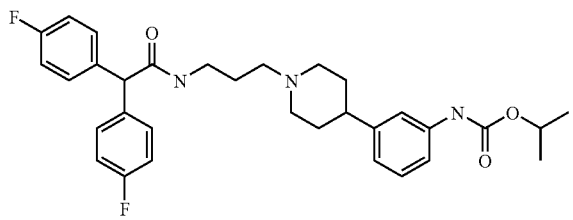

ISOPROPYL 3-[1-(3-{[BIS(4-FLUOROPHENYL) ACETYL]AMINO}PROPYL)-4-PIPERIDINYL] PHENYLCARBAMATE

Example 146 was prepared from bis(4-fluorophenyl)acetic acid and isopropyl 3-[1-(3-aminopropyl)-4-piperidinyl]phenylcarbamate according to the procedures described in Scheme 9: $^1$H NMR (400 MHz, CDCl$_3$) δ 7.43 (s, 2H), 7.30–7.19 (m, 4H), 7.11–7.07 (m, 1H), 7.01–6.96 (m, 5H), 6.88 (d, 1H, J=7.7 Hz), 6.69 (s, 1H), 4.97 (septet, 1H, J=6.3 Hz), 4.79 (s, 1H), 4.11 (q, 1H, J=6.8 Hz), 3.39 (q, 2H, J=5.6 Hz), 2.98–2.92 (m, 2H), 2.52–2.40 (m, 3H), 1.98 (t, 2H, J=11.5 Hz), 1.85–1.78 (m, 2H), 1.72–1.54 (m, 3H), 1.27 (d, 6H, J=6.3 Hz); ESMS m/e: 550.3 (M+H)+; Anal. Calc. for C$_{32}$H$_{37}$F$_2$N$_3$O$_3$.0.87 HCl: C, 66.84; H, 6.61; N, 7.31. Found: C, 66.83; H, 6.48; N, 7.31.

EXAMPLE 147

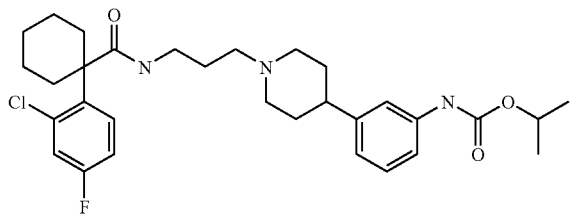

ISOPROPYL 3-{1-[3-({[1-(2-CHLORO-4-FLUOROPHENYL)CYCLOHEXYL]CARBONYL}AMINO)PROPYL]-4-PIPERIDINYL}PHENYLCARBAMATE

Example 147 was prepared from 1-(2-chloro-4-fluorophenyl)cyclohexanecarboxylic acid and isopropyl 3-[1-(3-aminopropyl)-4-piperidinyl]phenylcarbamate according to the procedures described in Scheme 9: ESMS m/e: 558.1 (M+H)+.

EXAMPLE 148

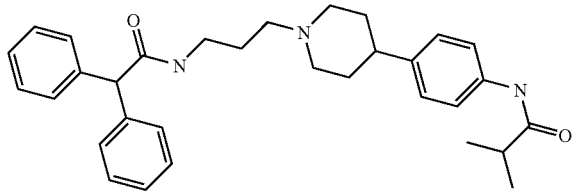

N-[4-(1-{3-[(DIPHENYLACETYL)AMINO]PROPYL}-4-PIPERIDINYL)PHENYL]-2-METHYLPROPANAMIDE

Example 148 was prepared from N-(3-bromopropyl)-2,2-diphenylacetamide and 2-methyl-N-[4-(4-piperidinyl)phenyl]propanamide according to the procedures described in Scheme 14: ESMS m/e: 498.3 (M+H)+.

EXAMPLE 149

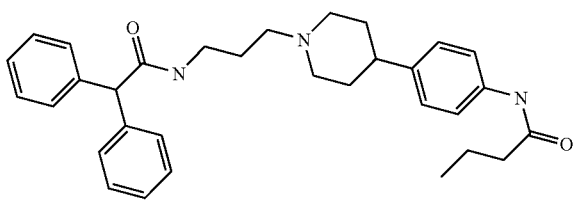

N-[4-(1-{3-[(2,2-DIPHENYLACETYL)AMINO]PROPYL}-4-PIPERIDINYL)PHENYL]BUTANAMIDE

Example 149 was prepared from N-(3-bromopropyl)-2,2-diphenylacetamide and N-[4-(4-piperidinyl)phenyl]butanamide according to the procedures described in Scheme 14: ESMS m/e: 498.3 (M+H)+.

EXAMPLE 150

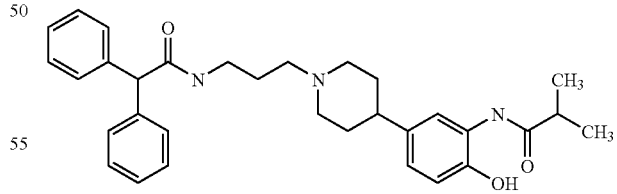

N-[5-(1-{3-[(DIPHENYLACETYL)AMINO]PROPYL}-4-PIPERIDINYL)-2-HYDROXYPHENYL]-2-METHYLPROPANAMIDE

Example 150 was prepared from diphenylacetyl chloride and N-{5-[1-(3-aminopropyl)-4-piperidinyl]-2-hydroxyphenyl}-2-methylpropanamide according to the procedures described in Scheme 8: $^1$H NMR (400 MHz, CDCl$_3$) δ 8.18

(s, 1H), 7.30–7.11 (m, 10H), 7.10–6.9 (m, 2H), 6.74 (d, 1H, J=8.3 Hz), 6.63 (dd, 1H, J=8.3, 2.0 Hz), 4.93 (s, 1H), 3.51 (t, 1H, J=5.4 Hz), 3.36 (quintet, 1H, J=6.5 Hz), 3.24–3.18 (m, 2H), 3.07–3.00 (m, 2H), 2.54–2.45 (m, 3H), 2.37–2.28 (m, 1H), 2.19–2.09 (m, 2H), 1.79–1.54 (m, 4H), 1.25 (d, 6H, J=6.8 Hz); ESMS m/e: 514.3 (M+H)$^+$.

EXAMPLE 151

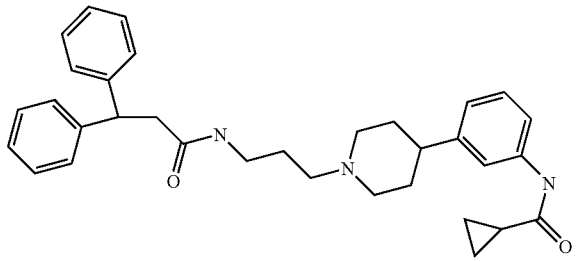

N-[3-(1-{3-[(3,3-DIPHENYLPROPANOYL) AMINO]PROPYL}-4-PIPERIDINYL)PHENYL] CYCLOPROPANECARBOXAMIDE

Example 151 was prepared from 3,3-diphenylpropanoic acid and N-{3-[1-(3-aminopropyl)-4-piperidinyl]phenyl}cyclopropanecarboxamide according to the procedures described in Scheme 9: ESMS m/e: 510.4 (M+H)$^+$.

EXAMPLE 152

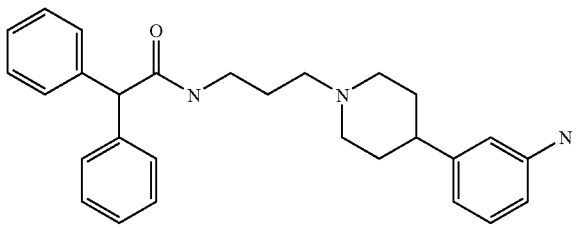

N-{3-[4-(3-AMINOPHENYL)-1-PIPERIDINYL] PROPYL}-2,2-DIPHENYLACETAMIDE

Example 152 was prepared via hydrogenation of benzyl 3-(1-{3-[(diphenylacetyl)amino]propyl}-4-piperidinyl)phenylcarbamate according to the procedures described in Scheme 15: ESMS m/e: 428.3 (M+H)$^+$.

II. Synthetic Methods for General Structures

The examples described in the experimental section are merely illustrative of the methods used to synthesize MCH1 antagonists. Additional compounds of the invention can be obtained by the general synthetic procedures described herein or by incorporating variations into these methods that would be obvious to someone skilled in the art.

It may be necessary to incorporate protection and deprotection strategies into the generalized synthetic methods in order to synthesize additional examples containing potentially reactive substituents such as amino, amido, carboxylic acid, and hydroxyl groups. Methods for protection and deprotection of such groups are well-known in the art, and may be found, for example in Green, T. W. and Wuts, P. G. M. (1991) *Protection Groups in Organic Synthesis, 2$^{nd}$ Edition* John Wiley & Sons, New York.

III. Oral Compositions

As a specific embodiment of an oral composition of a compound of this invention, 100 mg of one of the compounds described herein is formulated with sufficient finely divided lactose to provide a total amount of 580 to 590 mg to fill a size 0 hard gel capsule.

IV. Pharmacological Evaluation of Compounds at Cloned Rat MCH1 Receptor

The pharmacological properties of the compounds of the present invention were evaluated at the cloned rat MCH1 receptor using the protocols described below.

Host Cells

A broad variety of host cells can be used to study heterologously expressed proteins. These cells include but are not restricted to assorted mammalian lines such as: Cos-7, CHO, LM(tk–), HEK293, Peak rapid 293, etc.; insect cell lines such as: Sf9, Sf21, etc.; amphibian cells such as xenopus oocytes; and others.

COS 7 cells are grown on 150 mm plates in DMEM with supplements (Dulbecco's Modified Eagle Medium with 10% bovine calf serum, 4 mM glutamine, 100 units/ml penicillin/100 Fg/ml streptomycin) at 37° C., 5% $CO_2$. Stock plates of COS-7 cells are trypsinized and split 1:6 every 3–4 days.

Human embryonic kidney 293 cells are grown on 150 mm plates in DMEM with supplements (10% bovine calf serum, 4 mM glutamine, 100 units/ml penicillin/100 Fg/ml streptomycin) at 37° C., 5% $CO_2$. Stock plates of 293 cells are trypsinized and split 1:6 every 3–4 days.

Human embryonic kidney Peak rapid 293 (Peakr293) cells are grown on 150 mm plates in DMEM with supplements (10% fetal bovine serum, 10% L-glutamine, 50 Fg/ml gentamycin) at 37° C., 5% $CO_2$. Stock plates of Peak rapid 293 cells are trypsinized and split 1:12 every 3–4 days.

Mouse fibroblast LM(tk–) cells are grown on 150 mm plates in DMEM with supplements (Dulbecco's Modified Eagle Medium with 10% bovine calf serum, 4 mM glutamine, 100 units/ml penicillin/100 Fg/ml streptomycin) at 37° C., 5% $CO_2$. Stock plates of LM(tk–) cells are trypsinized and split 1:10 every 3–4 days.

Chinese hamster ovary (CHO) cells were grown on 150 mm plates in HAM=s F-12 medium with supplements (10% bovine calf serum, 4 mM L-glutamine and 100 units/ml penicillin/100 Fg/ml streptomycin) at 37° C., 5% $CO_2$. Stock plates of CHO cells are trypsinized and split 1:8 every 3–4 days.

Mouse embryonic fibroblast NIH-3T3 cells are grown on 150 mm plates in Dulbecco=s Modified Eagle Medium (DMEM) with supplements (10% bovine calf serum, 4 mM glutamine, 100 units/ml penicillin/100 Fg/ml streptomycin) at 37° C., 5% $CO_2$. Stock plates of NIH-3T3 cells are trypsinized and split 1:15 every 3–4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ medium supplemented with L-Glutamine, also at 27° C., no $CO_2$.

In some cases, cell lines that grow as adherent monolayers can be converted to suspension culture to increase cell yield and provide large batches of uniform assay material for routine receptor screening projects.

Transient Expression

DNA encoding proteins to be studied can be transiently expressed in a variety of mammalian, insect, amphibian and other cell lines by several methods including but not restricted to; calcium phosphate-mediated, DEAE-dextran mediated, Liposomal-mediated, viral-mediated, electroporation-mediated and microinjection delivery. Each of these methods may require optimization of assorted experimental parameters depending on the DNA, cell line, and the type of assay to be subsequently employed.

A typical protocol for the calcium phosphate method as applied to Peak rapid 293 cells is described as follows:

Adherent cells are harvested approximately twenty-four hours before transfection and replated at a density of $3.5 \times 10^6$ cells/dish in a 150 mm tissue culture dish and allowed to incubate over night at 37° C. at 5% $CO_2$. 250 Fl of a mixture of $CaCl_2$ and DNA (15 Fg DNA in 250 mM $CaCl_2$) is added to a 5 ml plastic tube and 500 Fl of 2× HBS (280 mM NaCl, 10 mM KCl, 1.5 mM $Na_2HPO_4$, 12 mM dextrose, 50 mM HEPES) is slowly added with gentle mixing. The mixture is allowed to incubate for 20 minutes at room temperature to allow a DNA precipitate to form. The DNA precipitate mixture is then added to the culture medium in each plate and incubated for 5 hours at 37° C., 5% $CO_2$. After the incubation, 5 ml of culture medium (DMEM, 10% FBS, 10% L-glut and 50 µg/ml gentamycin) is added to each plate. The cells are then incubated for 24 to 48 hours at 37° C., 5% $CO_2$.

A typical protocol for the DEAE-dextran method as applied to Cos-7 cells is described as follows; Cells to be used for transfection are split 24 hours prior to the transfection to provide flasks which are 70–80% confluent at the time of transfection. Briefly, 8 Fg of receptor DNA plus 8 Fg of any additional DNA needed (e.g. $G_\alpha$ protein expression vector, reporter construct, antibiotic resistance marker, mock vector, etc.) are added to 9 ml of complete DMEM plus DEAE-dextran mixture (10 mg/ml in PBS). Cos-7 cells plated into a T225 flask (sub-confluent) are washed once with PBS and the DNA mixture is added to each flask. The cells are allowed to incubate for 30 minutes at 37° C., 5% $CO_2$. Following the incubation, 36 ml of complete DMEM with 80 FM chloroquine is added to each flask and allowed to incubate an additional 3 hours. The medium is then aspirated and 24 ml of complete medium containing 10% DMSO for exactly 2 minutes and then aspirated. The cells are then washed 2 times with PBS and 30 ml of complete DMEM added to each flask. The cells are then allowed to incubate over night. The next day the cells are harvested by trypsinization and reseeded as needed depending upon the type of assay to be performed.

A typical protocol for liposomal-mediated transfection as applied to CHO cells is described as follows; Cells to be used for transfection are split 24 hours prior to the transfection to provide flasks which are 70–80% confluent at the time of transfection. A total of 10 Fg of DNA which may include varying ratios of receptor DNA plus any additional DNA needed (e.g. $G_\alpha$ protein expression vector, reporter construct, antibiotic resistance marker, mock vector, etc.) is used to transfect each 75 $cm^2$ flask of cells. Liposomal mediated transfection is carried out according to the manufacturer=s recommendations (LipofectAMINE, GibcoBRL, Bethesda, Md.). Transfected cells are harvested 24 hours post transfection and used or reseeded according the requirements of the assay to be employed.

A typical protocol for the electroporation method as applied to Cos-7 cells is described as follows; Cells to be used for transfection are split 24 hours prior to the transfection to provide flasks which are subconfluent at the time of transfection. The cells are harvested by trypsinization resuspended in their growth media and counted. $4 \times 10^6$ cells are suspended in 300 Fl of DMEM and placed into an electroporation cuvette. 8 Fg of receptor DNA plus 8 Fg of any additional DNA needed (e.g. $G_\alpha$ protein expression vector, reporter construct, antibiotic resistance marker, mock vector, etc.) is added to the cell suspension, the cuvette is placed into a BioRad Gene Pulser and subjected to an electrical pulse (Gene Pulser settings: 0.25 kV voltage, 950 FF capacitance). Following the pulse, 800 Fl of complete DMEM is added to each cuvette and the suspension transferred to a sterile tube. Complete medium is added to each tube to bring the final cell concentration to $1 \times 10^5$ cells/100 Fl. The cells are then plated as needed depending upon the type of assay to be performed.

A typical protocol for viral mediated expression of heterologous proteins is described as follows for baculovirus infection of insect Sf9 cells. The coding region of DNA encoding the receptor disclosed herein may be subcloned into pBlueBacIII into existing restriction sites or sites engineered into sequences 5' and 3' to the coding region of the polypeptides. To generate baculovirus, 0.5 Fg of viral DNA (BaculoGold) and 3 Fg of DNA construct encoding a polypeptide may be co-transfected into $2 \times 10^6$ *Spodoptera frugiperda* insect Sf9 cells by the calcium phosphate co-precipitation method, as outlined in by Pharmingen (in "Baculovirus Expression Vector System: Procedures and Methods Manual"). The cells then are incubated for 5 days at 27° C. The supernatant of the co-transfection plate may be collected by centrifugation and the recombinant virus plaque purified. The procedure to infect cells with virus, to prepare stocks of virus and to titer the virus stocks are as described in Pharmingen=s manual. Similar principals would in general apply to mammalian cell expression via retro-viruses, Simliki forest virus and double stranded DNA viruses such as adeno-, herpes-, and vacinia-viruses, and the like.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the heterologous DNA. An assortment of resistance genes are available including but not restricted to Neomycin, Kanamycin, and Hygromycin. For the purposes of receptor studies, stable expression of a heterologous receptor protein is carried out in, but not necessarily restricted to, mammalian cells including, CHO, HEK293, LM(tk−), etc.

Cell Membrane Preparation

For binding assays, pellets of transfected cells are suspended in ice-cold buffer (20 mM Tris HCl, 5 mM EDTA, pH 7.4) and homogenized by sonication for 7 sec. The cell lysates are centrifuged at 200×g for 5 min at 4° C. The supernatants are then centrifuged at 40,000×g for 20 min at 4° C. The resulting pellets are washed once in the homogenization buffer and suspended in binding buffer (see methods for radioligand binding). Protein concentrations are determined by the method of Bradford (1976) using bovine serum albumin as the standard. Binding assays are usually performed immediately, however it is possible to prepare membranes in batch and store frozen in liquid nitrogen for future use.

Radioligand Binding Assays

Radioligand binding assays for the rat MCH1 receptor were carried out using plasmid pcDNA3.1-rMCH1-f (ATCC Patent Deposit Designation No. PTA-3505). Plasmid pcDNA3.1-rMCH1-f comprises the regulatory elements necessary for expression of DNA in a mammalian cell operatively linked to DNA encoding the rat MCH1 receptor so as to permit expression thereof. Plasmid pcDNA3.1-rMCH1-f was deposited on Jul. 5, 2001, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Patent Deposit Designation No. PTA-3505.

Binding assays can also be performed as described hereinafter using plasmid pEXJ.HR-TL231 (ATCC Accession No. 203197) Plasmid pEXJ.HR-TL231 encodes the human MCH1 receptor and was deposited on Sep. 17, 1998, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 203197.

Human embryonic kidney Peak rapid 293 cells (Peakr293 cells) were transiently transfected with DNA encoding the MCH1 receptor utilizing the calcium phosphate method and cell membranes were prepared as described above. Binding experiments with membranes from Peakr293 cells transfected with the rat MCH1 receptor were performed with 0.08 nM [$^3$H]Compound A (the synthesis of Compound A is described in detail below) using an incubation buffer consisting of 50 mM Tris pH 7.4, 10 mM $MgCl_2$, 0.16 mM PMSF, 1 mM 1,10 phenantroline and 0.2% BSA. Binding was performed at 25° C. for 90 minutes. Incubations were terminated by rapid vacuum filtration over GF/C glass fiber filters, presoaked in 5% PEI using 50 nM Tris pH 7.4 as wash buffer. In all experiments, nonspecific binding is defined using 10 pM Compound A.

Functional Assays

Cells may be screened for the presence of endogenous mammalian receptor using functional assays. Cells with no or a low level of endogenous receptor present may be transfected with the exogenous receptor for use in functional assays.

A wide spectrum of assays can be employed to screen for receptor activation. These range from traditional measurements of phosphatidyl inositol, cAMP, $Ca^{++}$, and $K^+$, for example; to systems measuring these same second messengers but which have been modified or adapted to be higher throughput, more generic, and more sensitive; to cell based platforms reporting more general cellular events resulting from receptor activation such as metabolic changes, differentiation, and cell division/proliferation, for example; to high level organism assays which monitor complex physiological or behavioral changes thought to be involved with receptor activation including cardiovascular, analgesic, orexigenic, anxiolytic, and sedation effects, for example.

Radioligand Binding Assay Results

The compounds described above were assayed using cloned rat MCH1. The binding affinities of the compounds are shown in Table I.

TABLE I

| Example No. | Ki (MCH1, nM) |
|---|---|
| 1 | 1.3 |
| 2 | 2.4 |
| 3 | 2.5 |
| 4 | 2.5 |
| 5 | 3.1 |
| 6 | 5.6 |
| 7 | 7.9 |
| 8 | 11.7 |
| 9 | 71.6 |
| 10 | 83.0 |
| 11 | 8.4 |
| 12 | 13.9 |
| 13 | 11.8 |
| 14 | 2.7 |
| 15 | 8.9 |
| 16 | 1038 |
| 17 | 1.8 |
| 18 | 31.5 |
| 19 | 23.4 |
| 20 | 90.5 |
| 21 | 0.7 |
| 22 | 136.5 |
| 23 | 13.1 |
| 24 | 4.7 |
| 25 | 2.1 |
| 26 | 18.7 |
| 27 | 1.1 |
| 28 | 0.4 |
| 29 | 2.3 |
| 30 | 5.3 |
| 31 | 8.2 |
| 32 | 0.6 |
| 33 | 495.6 |
| 34 | 2.3 |
| 35 | 0.4 |
| 36 | 11.0 |
| 37 | 19.5 |
| 38 | 28.4 |
| 39 | 32.2 |
| 40 | 7.9 |
| 41 | 39.9 |
| 42 | 34.3 |
| 43 | 13.7 |
| 44 | 19.7 |
| 45 | 4.0 |
| 46 | 44.5 |
| 47 | 25.6 |
| 48 | 2.8 |
| 49 | 14.8 |
| 50 | 1.9 |
| 51 | 11.8 |
| 52 | 4.1 |
| 53 | 1.1 |
| 54 | 2.2 |
| 55 | 0.3 |
| 56 | 4.5 |
| 57 | 0.5 |
| 58 | 45.9 |
| 59 | 4.3 |
| 60 | 41.3 |
| 61 | 63.3 |
| 62 | 31.7 |
| 63 | 150.0 |
| 64 | 70.7 |
| 65 | 4.9 |
| 66 | 24.4 |
| 67 | 9.9 |
| 68 | 16.9 |
| 69 | 39.9 |
| 70 | 26.7 |
| 71 | 54.5 |
| 72 | 52.3 |
| 73 | 32.4 |
| 74 | 34.3 |
| 75 | 4.7 |
| 76 | 48.0 |

TABLE I-continued

| Example No. | Ki (MCH1, nM) |
|---|---|
| 77 | 30.7 |
| 78 | 6.7 |
| 79 | 5.9 |
| 80 | 7.7 |
| 81 | 3.2 |
| 82 | 8.6 |
| 83 | 10.3 |
| 84 | 12.6 |
| 85 | 4.6 |
| 86 | 3.2 |
| 87 | 6.4 |
| 88 | 23.0 |
| 89 | 10.8 |
| 90 | 52.2 |
| 91 | 2.9 |
| 92 | 2.6 |
| 93 | 4.9 |
| 94 | 3.1 |
| 95 | 23.5 |
| 96 | 2.6 |
| 97 | 3.6 |
| 98 | 4.3 |
| 99 | 2.9 |
| 100 | 5.0 |
| 101 | 11.2 |
| 102 | 7.9 |
| 103 | 8.0 |
| 104 | 0.9 |
| 105 | 2.8 |
| 106 | 19.0 |
| 107 | 101.2 |
| 108 | 1.9 |
| 109 | 4.7 |
| 110 | 50.4 |
| 111 | 1.2 |
| 112 | 3.2 |
| 113 | 0.8 |
| 114 | 4.0 |
| 115 | 6.9 |
| 116 | 18.9 |
| 117 | 17.9 |
| 118 | 13.9 |
| 119 | 18.6 |
| 120 | 0.4 |
| 121 | 10.2 |
| 122 | 4.8 |
| 123 | 2.8 |
| 124 | 39.9 |
| 125 | 124.5 |
| 126 | 3.0 |
| 127 | 175.0 |
| 128 | 2.9 |
| 129 | 4.5 |
| 130 | 2.6 |
| 131 | 4.0 |
| 132 | 0.6 |
| 133 | 5.9 |
| 134 | 2.4 |
| 135 | 5.2 |
| 136 | 48.7 |
| 137 | 11.8 |
| 138 | 10.2 |
| 139 | 33.4 |
| 140 | 180.0 |
| 141 | 8.8 |
| 142 | 77.4 |
| 143 | 6.2 |
| 144 | 33.2 |
| 145 | 26.9 |
| 146 | 6.2 |
| 147 | 42.0 |
| 148 | 144.0 |
| 149 | 467.0 |
| 150 | NA |
| 151 | 62.0 |
| 152 | 115.0 |

V. Synthesis of Radiolabeled Compound A

Described below is the synthesis of Compound A. Compound A is the radiolabeled compound that was used in the radioligand binding assays described above.

N-[3-(1,2,3,6-TETRAHYDRO-4-PYRIDINYL)PHENYL]ACETAMIDE

The reaction of saturated of aqueous $Na_2CO_3$ solution (25 mL), tert-butyl 4-{[(trifluoromethyl)sulfonyl]oxy}-1,2,3,6-tetrahydro-1-pyridine-carboxylate (20 mmol), 3-acetamidophenylboronic acid (30 mmol) and tetrakis-triphenylphosphine palladium (0) (1.15 g) in dimethoxyethane (40 mL) at reflux temperature overnight gave tert-butyl 4-[3-(acetylamino)phenyl]-3,6-dihydro-1(2H)-pyridinecarboxylate. Deprotection of the BOC group using HCl in dioxane followed by basification (pH 11–12) gave the desired product.

TERT-BUTYL N-(3-BROMOPROPYL)CARBAMATE was prepared from 3-bromopropylamine hydrobromide and $BOC_2O$ in the presence of base in dichloromethane.

N-{3-[1-(3-AMINOPROPYL)-1,2,3,6-TETRAHYDRO-4-PYRIDINYL]PHENYL}ACETAMIDE

The reaction of tert-butyl N-(3-bromopropyl)carbamate and N-[3-(1,2,3,6-tetrahydro-4-pyridinyl)phenyl]acetamide in refluxing dioxane with catalytic $Bu_4NI$ and base to give tert-butyl 3-(4-[3-(acetylamino)phenyl]-3,6-dihydro-1(2H)-pyridinyl)propylcarbamate. Deprotection of the BOC group using HCl in dioxane followed by basification (pH 11–12) gave the desired product.

METHYL (4S)-3-({[3-(4-[3-(ACETYLAMINO)PHENYL]-3,6-DIHYDRO-1(2H)-PYRIDINYL)PROPYL]AMINO}CARBONYL)-4-(3,4-DIFLUOROPHENYL)-6-(METHOXYMETHYL)-2-OXO-1,2,3,4-TETRAHYDRO-5-PYRIMIDINECARBOXYLATE

Prepared from the reaction of 5-methyl 1-(4-nitrophenyl) (6S)-6-(3,4-difluorophenyl)-4-(methoxymethyl)-2-oxo-3,6-dihydro-1,5(2H)-pyrimidinedicarboxylate (describe in PCT Publication No. WO 00/37026, published Jun. 29, 2000) and N-{3-[1-(3-aminopropyl)-1,2,3,6-tetrahydro-4-pyridinyl]phenyl}acetamide: $^1H$ NMR δ 8.90 (t, 1H, J=3.6 Hz), 7.75 (s, 1H), 7.50–7.00 (m, 8H), 6.68 (s, 1H), 6.03 (br s, 1H), 4.67 (s, 2H), 3.71 (s, 3H), 3.47 (s, 3H), 3.38 (ABm, 2H), 3.16 (m, 2H), 2.71 (t, 2H, J=5.4 Hz), 2.56 (m, 4H), 2.35–1.90 (br, 2H), 2.17 (s, 3H), 1.82 (p, 2H, J=7.2 Hz); ESMS, 612.25 $(M+H)^+$.

TRITIATED METHYL (4S)-3-{[(3-{4-[3-(ACETY-LAMINO)PHENYL]-1-PIPERIDINYL}PROPYL)AMINO]CARBONYL}-4-(3,4-DIFLUOROPHE-NYL)-6-(METHOXYMETHYL)-2-OXO-1,2,3,4-TETRAHYDRO-5-PYRIMIDINECARBOXYLATE ([$^3$H] COMPOUND A)

This radiochemical synthesis was carried out by Amersham Pharmacia Biotech, Cardiff, Wales. A methanolic solution of methyl (4S)-3-({[3-(4-[3-(acetylamino)phenyl]-3,6-dihydro-1(2H)-pyridinyl)propyl]amino}carbonyl)-4-(3,4-difluorophenyl)-6-(methoxymethyl)-2-oxo-1,2,3,4-tetrahydro-5-pyrimidinecarboxylate was exposed to tritium gas at 1 atmosphere pressure in the presence of 5% palladium on carbon with stirring overnight to give the tritiated methyl (4S)-3-{[(3-{4-[3-(acetylamino)phenyl]-1-piperidinyl}propyl)amino]carbonyl}-4-(3,4-difluorophenyl)-6-(methoxymethyl)-2-oxo-1,2,3,4-tetrahydro-5-pyrimidinecarboxylate ((+)-isomer). After purification by reverse phase HPLC (Hypersil ODS, 4.6×100 mm, methanol:H$_2$O:Et$_3$N 10:90:1 to 100:0:1 in 15 min at 1.0 mL/min, with radiochemical and UV detection), this product was used as a radioligand in the MCH1 binding assays. The same procedure was carried out with H$_2$ gas in place of $^3$H$_2$ to afford the non-radioactive version of Compound A.

VI. In-Vivo Methods

The following in vivo methods were performed to predict the efficacy of MCH1 antagonists for the treatment of obesity (3-day body weight and sweetened condensed milk), depression (forced swim test), anxiety (social interaction test), and urinary disorders (DIRC and CSTI).

Effects of MCH1 Antagonists on Body Weight (3 Day)

Male Long Evans rats (Charles River) weighing 180–200 grams were housed in groups of four on a 12-hour light/dark cycle with free access to food and water. Test compounds were administered twice daily via i.p. injection, 1 hour before the dark cycle and 2 hours after lights on, for three days. All rats were weighed daily after each morning injection. Overall results were expressed as body weight (grams) gained per day (mean±SEM) and were analyzed by two-way ANOVA. Data for each time point were analyzed by one-way ANOVA followed by post hoc Newman-Keuls test. The data were analyzed using the GraphPad Prism (v2.01) (GraphPad Software, Inc., San Diego, Calif.). All data were presented as means±S.E.M.

Effects of MCH1 Antagonists on Consumption of Sweetened Condensed Milk

Male C57BL/6 mice (Charles River) weighing 17–19 grams at the start of experiments were housed in groups of four or five on a 12 hour light/dark cycle with free access to food and water. For 7 days, mice were weighed, placed in individual cages and allowed to drink sweetened condensed milk (Nestle, diluted 1:3 with water) for 1 hour, 2–4 hours into the light cycle. The amount of milk consumed was determined by weighing the milk bottle before and after each drinking bout. On the test day, mice received i.p. injections of Test Compound (3, 10 or 30 mg/kg in 0.01% lactic acid), vehicle (0.01% lactic acid) of d-fenfluramine (10 mg/kg in 0.01% lactic acid) 30 min. prior to exposure to milk. The amount of milk consumed on the test day (in mls milk/kg body weight) was compared to the baseline consumption for each mouse determined on the previous 2 days. Data for each time point were analyzed by one-way ANOVA.

Forced Swim Test (FST) in the Rat

Animals

Male Sprague-Dawley rats (Taconic Farms, N.Y.) were used in all experiments. Rats were housed 5 per cage and maintained on a 12:12-h light-dark cycle. Rats were handled for 1 minutes each day for 4 days prior to behavioral testing.

Drug Administration

Animals were randomly assigned to receive a single i.p. administration of vehicle (2.5% EtOH/2.5% Tween-80), imipramine (positive control; 60 mg/kg), or Test Compound 60 minutes before the start of the 5 minute test period. All injections were given using 1 cc tuberculin syringe with 26⅜ gauge needles (Becton-Dickinson, VWR Scientific, Bridgeport, N.J.). The volume of injection was 1 ml/kg.

Experimental Design

The procedure used in this study was similar to that previously described (Porsolt, et al., 1978), except the water depth was 31 cm in this procedure. The greater depth in this test prevents the rats from supporting themselves by touching the bottom of the cylinder with their feet. Swim sessions were conducted by placing rats in individual plexiglass cylinders (46 cm tall×20 cm in diameter) containing 23–25° C. water 31 cm deep. Swim tests were conducted always between 900 and 1700 hours and consisted of an initial 15-min conditioning test followed 24 h later by a 5-minute test. Drug treatments were administered 60 minutes before the 5-minute test period. Following all swim sessions, rats were removed from the cylinders, dried with paper towels and placed in a heated cage for 15 minutes and returned to their home cages. All test sessions were videotaped using a color video camera and recorded for scoring later.

Behavioral Scoring

The rat's behavior was rated at 5-second intervals during the 5-minute test by a single individual, who was blind to the treatment condition. Scored behaviors were:

1. Immobility—rat remains floating in the water without struggling and was only making those movements necessary to keep its head above water;
2. Climbing—rat was making active movements with its forepaws in and out of the water, usually directed against the walls;
3. Swimming—rat was making active swimming motions, more than necessary to merely maintain its head above water, e.g. moving around in the cylinder; and
4. Diving—entire body of the rat was submerged.

Data Analysis

The forced swim test data (immobility, swimming, climbing, diving) were subjected to a randomized, one-way ANOVA and post hoc tests conducted using the Newman-Keuls test. The data were analyzed using the GraphPad Prism (v2.01) (GraphPad Software, Inc., San Diego, Calif.). All data were presented as means±S.E.M. All data were presented as means±S.E.M.

Forced Swim Test (FST) in the Mouse

Animals

DBA/2 mice (Taconic Farms, N.Y.) were used in all experiments. Animals were housed 5 per cage in a controlled environment under a 12:12 hour light:dark cycle. Animals were handled 1 min each day for 4 days prior to the experiment. This procedure included a mock gavage with a 1.5 inch feeding tube.

Drug Administration

Animals were randomly assigned to receive a single administration of vehicle (5% EtOH/5% Tween-80), Test Compound, or imipramine (60 mg/kg) by oral gavage 1 hour before the swim test.

Experimental Design

The procedure for the forced swim test in the mouse was similar to that described above for the rat, with some modifications. The cylinder used for the test was a 1-liter beaker (10.5 cm diameter×15 cm height) fill to 800 ml (10 cm depth) of 23–25° C. water. Only one 5-minute swim test was conducted for each mouse, between 1300 and 1700 hours. Drug treatments were administered 30–60 minutes before the 5-minute test period. Following all swim sessions, mice were removed from the cylinders, dried with paper towels and placed in a heated cage for 15 minutes. All test sessions were videotaped using a Sony color video camera and recorder for scoring later.

Behavioral Scoring

The behavior during minutes 2–5 of the test was played back on a TV monitor and scored by the investigator. The total time spent immobile (animal floating with only minimal movements to remain afloat) and mobile (swimming and movements beyond those required to remain afloat) were recorded.

Data Analysis

The forced swim test data (time exhibiting immobility, mobility; seconds) were subjected to a randomized, one-way ANOVA and post hoc tests conducted using the Newman-Keuls test. The data were analyzed using the GraphPad Prism (v2.01) (GraphPad Software, Inc., San Diego, Calif.). All data were presented as means±S.E.M.

Social Interaction Test (SIT)

Rats are allowed to acclimate to the animal care facility for 5 days and are housed singly for 5 days prior to testing. Animals are handled for 5 minutes per day. The design and procedure for the Social Interaction Test is carried out as previously described by Kennett, et al. (1997). On the test day, weight matched pairs of rats (±5%), unfamiliar to each other, are given identical treatments and returned to their home cages. Animals are randomly divided into 5 treatment groups, with 5 pairs per group, and are given one of the following i.p. treatments: Test Compound (10, 30 or 100 mg/kg), vehicle (1 ml/kg) or chlordiazepoxide (5 mg/kg). Dosing is 1 hour prior to testing. Rats are subsequently placed in a white perspex test box or arena (54×37×26 cm), whose floor is divided up into 24 equal squares, for 15 minutes. An air conditioner is used to generate background noise and to keep the room at approximately 74° F. All sessions are videotaped using a JVC camcorder (model GR-SZ1, Elmwood Park, N.J.) with either TDK (HG ultimate brand) or Sony 30 minute videocassettes. All sessions are conducted between 1300–1630 hours. Active social interaction, defined as grooming, sniffing, biting, boxing, wrestling, following and crawling over or under, is scored using a stopwatch (Sportsline model no. 226, 1/100 sec. discriminability). The number of episodes of rearing (animal completely raises up its body on its hind limbs), grooming (licking, biting, scratching of body), and face washing (i.e. hands are moved repeatedly over face), and number of squares crossed are scored. Passive social interaction (animals are lying beside or on top of each other) is not scored. All behaviors are assessed later by an observer who is blind as to the treatment of each pair. At the end of each test, the box is thoroughly wiped with moistened paper towels.

Animals

Male albino Sprague-Dawley rats (Taconic Farms, N.Y.) are housed in pairs under a 12 hr light dark cycle (lights on at 0700 hrs.) with free access to food and water.

Drug Administration

Test Compound is dissolved in either 100% DMSO or 5% lactic acid, v/v (Sigma Chemical Co., St. Louis, Mo.). Chlordiazepoxide (Sigma Chemical Co., St. Louis, Mo.) is dissolved in double distilled water. The vehicle consists of 50% DMSO (v/v) or 100% dimethylacetamide (DMA). All drug solutions are made up 10 minutes prior to injection and the solutions are discarded at the end of the test day. The volume of drug solution administered is 1 ml/kg.

Data Analysis

The social interaction data (time interacting, rearing and squares crossed) are subjected to a randomized, one-way ANOVA and post hoc tests conducted using the Student-Newman-Keuls test. The data are subjected to a test of normality (Shapiro-Wilk test). The data are analyzed using the GBSTAT program, version 6.5 (Dynamics Microsystems, Inc., Silver Spring, Md., 1997).

In Vivo Models of the Micturition Reflex

The effects of compounds on the micturition reflex were assessed in the "distension-induced rhythmic contraction" (DIRC), as described in previous publications (e.g. Maggi et al, 1987; Morikawa et al, 1992), and Continuous Slow Transvesicular Infusion (CSTI) models in rats.

DIRC Model

Female Sprague Dawley rats weighing approximately 300 g were anesthetized with subcutaneous urethane (1.2 g/kg). The trachea was cannulated with PE240 tubing to provide a clear airway throughout the experiment. A midline abdominal incision was made and the left and right ureters were isolated. The ureters were ligated distally (to prevent escape of fluids from the bladder) and cannulated proximally with PE10 tubing. The incision was closed using 4-0 silk sutures, leaving the PE10 lines routed to the exterior for the elimination of urine. The bladder was canulated via the transurethral route using PE50 tubing inserted 2.5 cm beyond the urethral opening. This cannula was secured to the tail using tape and connected to a pressure transducer. To prevent leakage from the bladder, the cannula was tied tightly to the exterior urethral opening using 4-0 silk.

To initiate the micturition reflex, the bladder was first emptied by applying pressure to the lower abdomen, and then filled with normal saline in 100 increments (maximum=2 ml) until spontaneous bladder contractions occurred (typically 20–40 mmHg at a rate of one contraction every 2 to 3 minutes. Once a regular rhythm was established, vehicle (saline) or Test Compounds were administered i.v. or i.p. to explore their effects on bladder activity. The 5-$HT_{1A}$ antagonist WAY-100635 was given as a positive control. Data were expressed as contraction interval (in seconds) before drug application (basal), or after the application of vehicle or test article.

Continuous Slow Transvesicular Infusion (CSTI) Rat Model

Male Sprague Dawley rats weighing approximately 300 g were used for the study. Rats were anaesthetized with pentobarbitone sodium (50 mg/kg, i.p). Through a median abdominal incision, bladder was exposed and a polyethylene cannula (PE 50) was introduced into the bladder through a small cut on the dome of the bladder and the cannula was secured with a purse string suture. The other end of the cannula was exteriorized subcutaneously at the dorsal neck area. Similarly, another cannula (PE 50) was introduced into the stomach through a paramedian abdominal incision with the free end exteriorized subcutaneously to the neck region. The surgical wounds were closed with silk 4-0 suture and the animal was allowed to recover with appropriate post surgical care. On the following day, the animal was placed in a rat restrainer. The open end of the bladder-cannula was connected to a pressure transducer as well as infusion pump through a three-way stopcock. The bladder voiding cycles were initiated by continuous infusion of normal saline at the rate of 100 μl/min. The repetitive voiding contractions were recorded on a Power Lab on-line data acquisition software. After recording the basal voiding pattern for an hour, the test drug or vehicle was administered directly into stomach through the intragastric catheter and the voiding cycles were monitored for 5 hours. Micturition pressure and frequency were calculated before and after the treatment (at every 30 min interval) for each animal. Bladder capacity was calculated from the micturition frequency, based on the constant infusion of 100 ul/min. The effect of the test drug was expressed as a percentage of basal, pre-drug bladder capacity. WAY 100635 was used as positive control for comparison.

In Vivo Results

TABLE 2

Effect of MCH1 antagonist (Example No.) in the following in vivo models: 3-day Body Weight (3D BW), mouse Sweetened Condensed Milk (mSwCM), mouse Forced Swim Test (mFST), rat Forced Swim Test (rFST), DIRC model, or CSTI model.

| Example No. | 3D BW | mSwCM | mFST | RFST | DIRC | CSTI |
|---|---|---|---|---|---|---|
| 1 | Not tested | Not tested | No effect | Not tested | Not tested | F |
| 3 | Not tested | Not tested | Not tested | Not tested | Not tested | F |
| 4 | Not tested | Not tested | C | Not tested | Not tested | F |
| 6 | Not tested | Not tested | C | Not tested | Not tested | F |
| 8 | Not tested | Not tested | C | Not tested | Not tested | F |
| 24 | Not tested | Not tested | Not tested | Not tested | Not tested | F |
| 29 | Not tested | Not tested | Not tested | Not tested | Not tested | F |
| 32 | Not tested | Not tested | Not tested | Not tested | Not tested | F |
| 35 | Not tested | Not tested | C | Not tested | Not tested | F |

A = Produced a significant reduction in weight gain relative to vehicle-treated controls
B = Produced a significant decrease in consumption of milk relative to vehicle-treated controls
C = Produced a significant decrease in immobility relative to vehicle-treated animals when administered orally.
D = Produced a significant decrease in immobility or a significant increase in swimming activity relative to vehicle-treated animals
E = Produced a significant increase in contraction interval relative to pre-drug interval
F = Produced an increase in bladder capacity in rats relative to baseline capacity.

REFERENCES

American Psychiatric Association (1994a), Diagnostic and Statistical Manual of Mental Disorders. 4th ed. Washington, D.C.: American Psychiatric Association.

American Psychiatric Association (1994b), American DSM-IV Sourcebook. Washington, D.C.: American Psychiatric Association.

Auburger, G., et al., (1992) Assignment of the second (cuban) locus of autosomal dominant cerebellar ataxia to chromosome 12q23-24.1, between flanking markers D12S58 and PLA2. *Cytogenet. Cell. Genet.* 61:252–256.

Bahjaoui-Bouhaddi, M., et al., (1994) Insulin treatment stimulates the rat melanin-concentrating hormone-producing neurons. *Neuropeptides* 24:251–258.

Baker, B. I. (1991) Melanin-concentrating hormone: a general vertebrate neuropeptide. *Int. Rev. Cytol.* 126:1–47.

Baker, B. I. (1994) Melanin-concentrating hormone update: functional consideration. *TEM* 5:120–126.

Bassett, A. S., et al., (1988) Partial trisomy chromosome 5 cosegregating with schizophrenia. *Lancet* 1:799–801.

Bednarek, M. A., et al. "Synthesis and biological evaluation in vitro of a selective, high potency peptide agonist of human melanin-concentrating hormone action at human melanin-concentrating hormone receptor 1" *J Biol Chem* 277(16): 13821–13826 (2002).

Bittencourt, J. C., et al., (1992) The melanin-concentrating hormone system of the rat brain: An immuno- and hybridization histochemical characterization. *J. Comp. Neurol.* 319:218–245.

Bobes, J. (1998) J Clin Psychiatry; 59[suppl 17]:12–16.

Borowsky, B., et al., *Nature Medicine* (in press).

Bradford, M. M. (1976) A rapid and sensitive method for the quantitation of microgram quantities of protein utilizing the principle or protein-dye binding. *Anal. Biochem.* 72: 248–254.

Burgaud, J. L., et al., (1997) Melanin-concentrating hormone binding sites in human SVK14 keratinocytes. *Biochem. Biophys. Res. Commun.* 241(3):622–629.

Chambers, J., et al., "Melanin-concentrating hormone is the cognate ligand for the orphan G-protein-coupled receptor SLC-1" *Nature* 400(6741): 261–6 (1999).

Chen, Y., et al, "Targeted disruption of the melanin-concentrating hormone receptor-1 results in hyperphagia and resistance to diet-induced obesity" *Endocrinology* 143 (7): 2469–2477 (2002).

Craddock, N., et al., (1993) The gene for Darier=s disease maps to chromosome 12q23-q24.1. *Hum. Mol. Genet.* 2:1941–1943.

Dondoni, A., et al., (1995) T. *Synthesis,* 181.

Drozdz, R. and Eberle, A. N. (1995) Binding sites for melanin-concentrating hormone (MCH) in brain synaptosomes and membranes from peripheral tissues identified with highly tritiated MCH. *J. Recept. Signal. Transduct. Res.* 15(1–4):487–502.

Drozdz, R., et al., (1995) Melanin-concentrating hormone binding to mouse melanoma cells in vitro. *FEBS* 359: 199–202.

Drozdz, R., et al., (1998) Characterization of the receptor for melanin-concentrating hormone on melanoma cells by photocrosslinking. *Ann. NY Acad. Sci.* 839(1):210–213.

Gale Group (2001) Gale Encyclopedia of Psychology, 2nd ed. Gale Group.

Gilliam, T. C., et al., (1989) Deletion mapping of DNA markers to a region of chromosome 5 that cosegregates with schizophrenia. *Genomics* 5:940–944.

Goodman W K, Price L H, Rasmussen S A et al. (1989), The Yale-Brown Obsessive Compulsive Scale. Arch Gen Psychiatry 46:1006–1011.

Gonzalez, M. I., et al., (1997) Stimulatory effect of melanin-concentrating hormone on luteinizing hormone release. *Neuroendocrinology* 66(4):254–262.

Gonzalez, M. I., et al., (1996) Behavioral effects of α-melanocyte-stimulating hormone (α-MSH) and melanin-concentrating hormone (MCH) after central administration in female rats. *Peptides* 17:171–177.

Grillon, S., et al., (1997) Exploring the expression of the melanin-concentrating hormone messenger RNA in the rat lateral hypothalamus after goldthioglucose injection. *Neuropeptides* 31(2):131–136.

Herve, C. and Fellmann, D. (1997) Changes in rat melanin-concentrating hormone and dynorphin messenger ribonucleic acids induced by food deprivation. *Neuropeptides* 31(3):237–242.

Hervieu, G., et al., (1996) Development and stage-dependent expression of melanin-concentrating hormone in mammalian germ cells. *Biology of Reproduction* 54:1161–1172.

Kauwachi, H., et al., (1983) Characterization of melanin-concentrating hormone in chum salmon pituitaries. *Nature* 305:321–333.

Knigge, K. M., et al., (1996) Melanotropic peptides in the mammalian brain: The melanin-concentrating hormone. *Peptides* 17:1063–1073.

Knigge, K. M. and Wagner, J. E. (1997) Melanin-concentrating hormone (MCH) involvement in pentylenetetrazole (PTZ)-induced seizure in rat and guinea pig. *Peptides* 18(7): 1095–1097.

Lakaye, B., et al., "Cloning of the rat brain cDNA encoding for the SLC-1 G protein-coupled receptor reveals the presence of an intron in the gene" *Biochem Biophys Acta* 1401(2): 216–220 (1998).

Ludwig, D. S., et al., (1998) Melanin-concentrating hormone: a functional melanocortin antagonist in the hypothalamus. *Am. J. Physiol. Endocrinol. Metab.* 274(4): E627–E633.

MacKenzie, F. J., et al., (1984) Evidence that the dopaminergic incerto-hypothalamic tract has a stimulatory effect on ovulation and gonadotropin release. *Neuroendocrinology* 39:289–295.

Maggi, C. A., et al., "Spinal and supraspinal components of GABAergic inhibition of the micturition reflex in rats." *J Pharmacol Exp Ther* 240: 998–1005 (1987).

Marsh, D. J., et al, "Melanin-concentrating hormone 1 receptor-deficient mice are lean, hyperactive, and hyperphagic and have altered metabolism" *Proc Natl Acad Sci USA* 99(5): 3240–3245 (2002).

Martin, R., et al., (1997) *J. Tetrahedron Letters*, 38, 1633.

McBride, R. B., et al., (1994) The actions of melanin-concentrating hormone (MCH) on passive avoidance in rats: A preliminary study. *Peptides* 15:757–759.

Medical Economics Company (2002), Physicians' Desk Reference, 56th ed., Montvale, N.J.: Medical Economics Company, Inc., pp. 1609–1615, 2751–2756, 3495–3504.

Melki, J., et al., (1990) Gene for chronic proximal spinal muscular atrophies maps to chromosome 5q. *Nature* (London) 344:767–768.

Miller, C. L., et al., (1993) α-MSH and MCH are functional antagonists in a CNS auditory paradigm. *Peptides* 14:1–10.

Morikawa, K., et al., "Inhibitory effect of inaperisone hydrochloride (inaperisone), a new centrally acting muscle relaxant, on the micturition reflex." *Eur J Pharmacol* 213: 409–415 (1992).

Nahon, J-L. (1994) The melanin-concentrating hormone: from the peptide to the gene. *Critical Rev. in Neurobiol* 221:221–262.

Parkes, D. G. (1996) Diuretic and natriuretic actions of melanin concentrating hormone in conscious sheep. *J. Neuroendocrinol.* 8:57–63.

Pedeutour, F., et al., (1994) Assignment of the human pro-melanin-concentrating hormone gene (PMCH) to chromosome 12q23-24 and two variant genes (PMCHL1 and PMCHL2) to chromosome 5p14 and 5q12-q13. *Genomics* 19:31–37.

Porsolt, R. D., et al., "Behavioural despair in rats: a new model sensitive to antidepressant treatments" *Eur J Pharmacol* 47(4): 379–391 (1978).

Presse, F., et al. (1992) Rat melanin-concentrating hormone messenger ribonucleic acid expression: marked changes during development and after stress and glucocorticoid stimuli. *Endocrinology* 131:1241–1250.

Qu, D., et al. (1996) A role for melanin-concentrating hormone in the central regulation of feeding behaviour. *Nature* 380:243–247.

Rossi, M., et al., (1997) Melanin-concentrating hormone acutely stimulates feeding, but chronic administration has no effect on body weight. *Endocrinology* 138:351–355.

Sahu, A. (1998) Evidence suggesting that galanin (GAL), melanin-concentrating hormone (MCH), neurotensin (NT), proopiomelanocortin (POMC) and neuropeptide Y (NPY) are targets of leptin signaling in the hypothalamus. *Endocrinology* 139(2):795–798.

Sakurai, T., et al., (1998) Orexins and orexin receptors: A family of hypothalamic neuropeptides and G protein-coupled receptors that regulate feeding behavior. *Cell* 92:573–585.

Sanchez, M., et al., (1997) Melanin-concentrating hormone (MCH) antagonizes the effects of α-MSH and neuropeptide E-I on grooming and locomotor activities in the rat. *Peptides* 18:393–396.

Saito, Y., et al., "Molecular characterization of the melanin-concentrating-hormone receptor" *Nature* 400(6741): 265–269 (1999).

Schneier F R, Heckelman L R, Garfinkel R, et al. (1994) J Clin Psychiatry 55:322–331.

Sherrington, R., et al., (1988) Localization of a susceptibility locus for schizophrenia on chromosome 5. *Nature* (*London*) 336:164–167.

Srebnik, M., et al., (1988) *J. Org. Chem.*, 53, 2916–2920.

Takekawa, S., et al., "T-226296: a novel, orally active and selective melanin-concentrating hormone receptor antagonist" *Eur J Pharmacol* 438(3): 129–35 (2002)

Twells, R., et al., (1992) Chromosomal assignment of the locus causing olivo-ponto-cerebellar atrophy (SCA2) in a cuban founder population. *Cytogenet. Cell. Genet.* 61:262–265.

Westbrook, C. A., et al., (1992) Report of the second international workshop on human chromosome 5 mapping. *Cytogenet. Cell. Genet.* 61:225–231.

What is claimed is:

1. A compound having the structure:

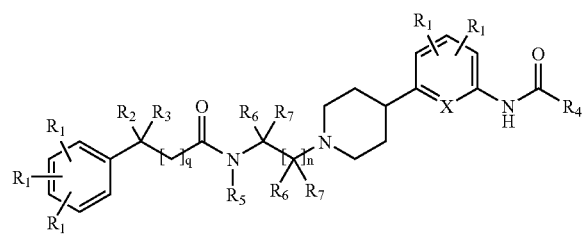

wherein each $R_1$ is independently hydrogen; —F; —Cl; —Br; —I; —CN; —$NO_2$; straight chained or branched $C_1$–$C_7$ alkyl, monofluoroalkyl or polyfluoroalkyl; straight chained or branched $C_2$–$C_7$ alkenyl; $C_3$–$C_7$ cycloalkyl or $C_5$–$C_7$ cycloalkenyl; aryl; heteroaryl; —N($R_5$)$_2$; —(CH$_2$)$_m$OR$_5$; —COR$_5$; —CO$_2$R$_5$; —OCOR$_5$; —CON($R_5$)$_2$; —N($R_5$)COR$_5$; —N($R_5$)CON($R_5$)$_2$; —OCON($R_5$)$_2$ or —N($R_5$)CO$_2$R$_5$;

wherein $R_2$ and $R_3$ are independently hydrogen; —F; —Cl; —Br; —I; —CN; —(CH$_2$)$_m$OR$_5$; —(CH$_2$)$_m$SR$_5$; straight chained or branched $C_1$–$C_7$ alkyl, monofluoroalkyl, polyfluoroalkyl; aryl or heteroaryl, wherein the aryl or heteroaryl may be substituted with one or more $R_1$; or wherein $R_2$ and $R_3$ together can be —(CH$_2$)$_p$—;

wherein $R_4$ is straight chained or branched $C_1$–$C_7$ alkyl, monofluoroalkyl or polyfluoroalkyl, $C_3$–$C_6$ cycloalkyl, —N($R_5$)$_2$ or —(CH$_2$)$_m$OR$_5$;

wherein each $R_5$ is independently hydrogen; aryl; heteroaryl or straight chained or branched $C_1$–$C_7$ alkyl, wherein the alkyl may be substituted with aryl or heteroaryl;

wherein each $R_6$ is independently hydrogen; straight chained or branched $C_1$–$C_7$ alkyl;

wherein each $R_7$ is independently hydrogen; phenyl or straight chained or branched $C_1$–$C_7$ alkyl, wherein the alkyl may be substituted with phenyl;

wherein each m is independently an integer from 0 to 5 inclusive;

wherein n is an integer from 1 to 5 inclusive;

wherein p is an integer from 2 to 7 inclusive;

wherein q is an integer from 0 to 2 inclusive;

wherein X is CH or N;

or a pharmaceutically acceptable salt thereof.

2. The compound of claim 1, wherein each $R_1$ is independently hydrogen; straight chained or branched $C_1$–$C_7$ alkyl; —F; —Cl; —Br; —I; —CN; —NO$_2$; straight chained or branched $C_1$–$C_4$ alkyl or polyfluoroalkyl; —(CH$_2$)$_m$OR$_5$; —COR$_5$; —CO$_2$R$_5$; —OCOR$_5$; —CON($R_5$)$_2$; —N($R_5$)COR$_5$ or —N($R_5$)CON($R_5$)$_2$;

wherein $R_2$ and $R_3$ are independently hydrogen; —F; —Cl; —Br; —I; —CN; —(CH$_2$)$_m$SR$_5$; straight chained or branched $C_1$–$C_7$ alkyl; aryl or heteroaryl, wherein the aryl or heteroaryl may be substituted with one or more $R_1$; or wherein $R_2$ and $R_3$ together can be —(CH$_2$)$_p$—;

wherein $R_4$ is straight chained or branched $C_1$–$C_7$ alkyl; $C_3$–$C_6$ cycloalkyl; —N($R_5$)$_2$ or —(CH$_2$)$_m$OR$_5$;

wherein each $R_5$ is independently hydrogen or straight chained or branched $C_1$–$C_3$ alkyl, wherein the alkyl may be substituted with phenyl;

wherein m is 0 to 3;

wherein n is 1 to 3;

wherein p is an integer from 2 to 5 inclusive;

wherein q is 0; and wherein X is CH.

3. The compound of claim 2, wherein the compound has the following structure:

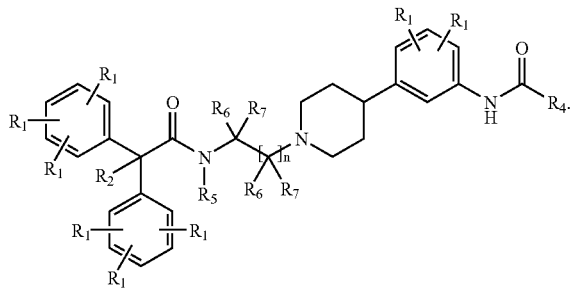

4. The compound of claim 3, wherein the compound has the following structure:

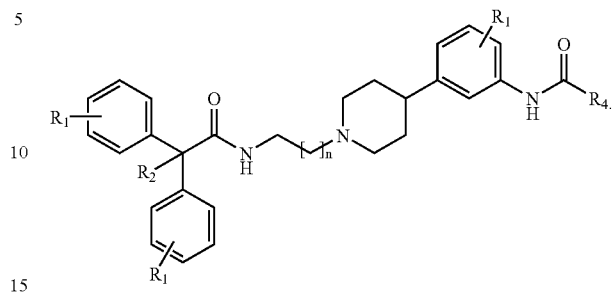

5. The compound of claim 4, wherein $R_1$ is hydrogen; —F; —Cl; —Br; —I or straight chained or branched $C_1$–$C_7$ alkyl; and wherein $R_2$ is hydrogen or straight chained or branched $C_1$–$C_7$ alkyl.

6. The compound of claim 5, wherein $R_4$ is straight chained or branched $C_1$–$C_7$ alkyl.

7. The compound of claim 6, wherein the compound has the structure:

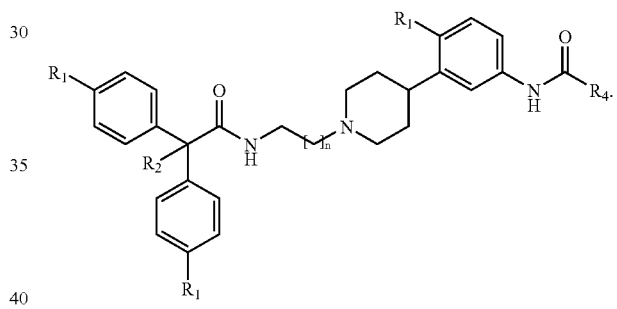

8. The compound of claim 7, wherein the compound is selected from the group consisting of:

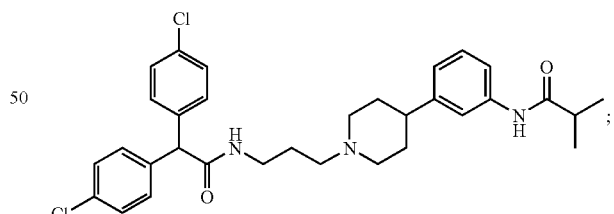

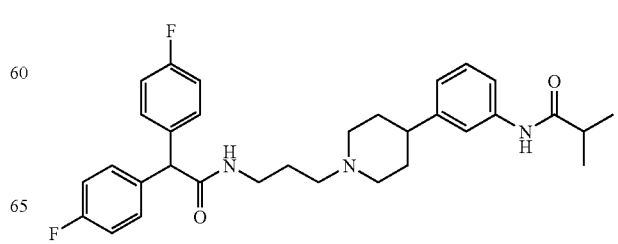

-continued or

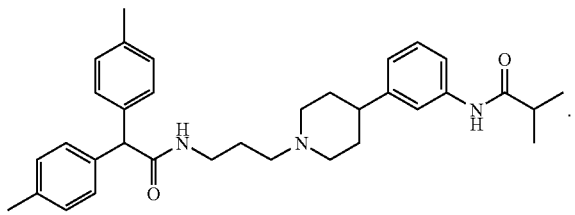

9. The compound of claim 7, wherein the compound is selected from the group consisting of:

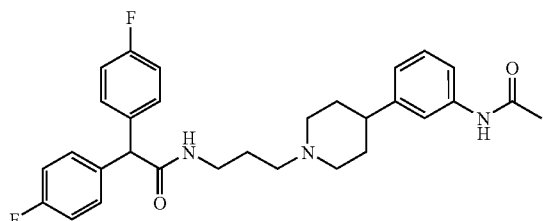

or

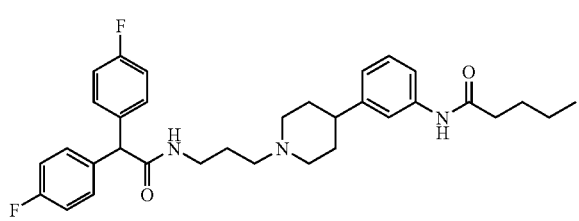

10. The compound of claim 7, wherein the compound is selected from the group consisting of:

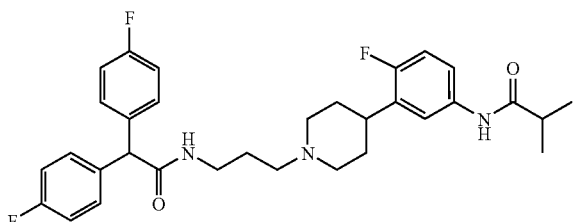

or

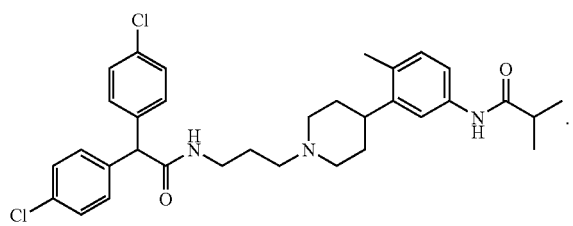

11. The compound of claim 4, wherein $R_4$ is $C_3$–$C_6$ cycloalkyl.

12. The compound of claim 11, wherein the compound is selected from the group consisting of:

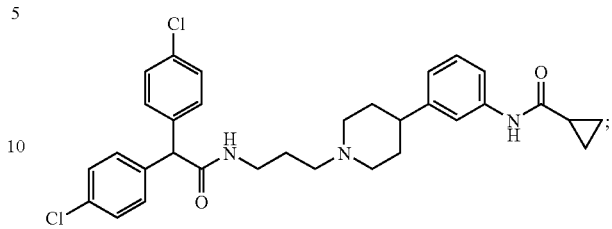

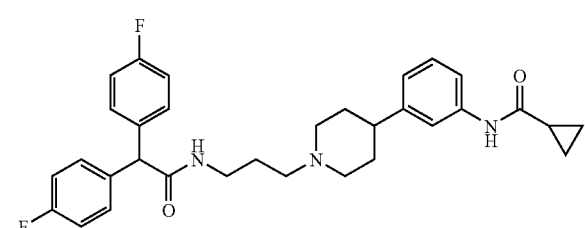

or

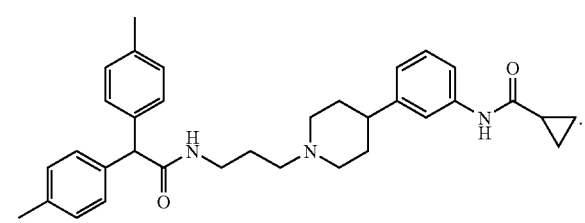

13. The compound of claim 2, wherein $R_2$ and $R_3$ are independently hydrogen; —F; —Br or straight chained or branched $C_1$–$C_7$ alkyl.

14. The compound of claim 13, wherein $R_2$ and $R_3$ are independently hydrogen or straight chained or branched $C_1$–$C_7$ alkyl.

15. The compound of claim 14, wherein the compound has the structure:

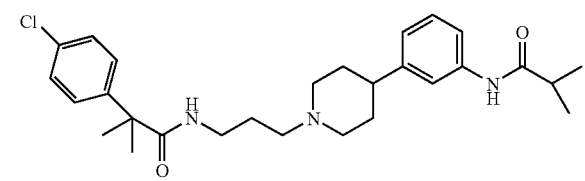

or

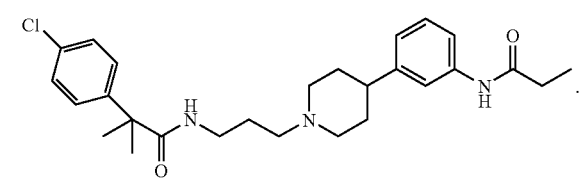

16. The compound of claim 13, wherein $R_2$ and $R_3$ are independently hydrogen; —F or —Br.

17. The compound of claim 16, wherein the compound has the structure:

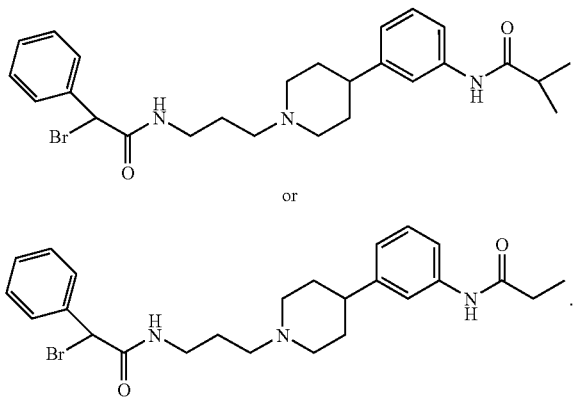

or

18. The compound of claim 1, wherein the compound is enantiomerically pure.

19. The compound of claim 1, wherein the compound is diastereomerically pure.

20. A pharmaceutical composition that comprises a therapeutically effective amount of the compound of claim 1 and a pharmaceutically acceptable carrier.

21. A pharmaceutical composition made by admixing a therapeutically effective amount of a compound of claim 1 and a pharmaceutically acceptable carrier.

22. A process for making a pharmaceutical composition comprising admixing a therapeutically effective amount of a compound of claim 1 and a pharmaceutically acceptable carrier.

23. A method of treating a subject suffering from a disorder selected from the group consisting of depression, anxiety, urge incontinence or obesity, comprising administering to the subject a therapeutically effective amount of the compound of claim 1.

24. The method of claim 23, wherein the therapeutically effective amount is between about 0.03 and about 300 mg.

25. The method of claim 23, wherein the disorder is depression.

26. The method of claim 23, wherein the disorder is anxiety.

27. The method of claim 23, wherein the disorder is obesity.

* * * * *

UNITED STATES PATENT AND TRADEMARK OFFICE
CERTIFICATE OF CORRECTION

PATENT NO. : 7,105,544 B2
APPLICATION NO. : 10/345063
DATED : September 12, 2006
INVENTOR(S) : Mohammad R. Marzabadi et al.

It is certified that error appears in the above-identified patent and that said Letters Patent is hereby corrected as shown below:

On The Title Page Item (73)

In the Assignee:

Please delete "Synaptic Pharmaceutical Corporation, Paramus, NJ (US)" and substitute -- H. Lund beck A/S --.

Signed and Sealed this

First Day of April, 2008

JON W. DUDAS
*Director of the United States Patent and Trademark Office*